(12) United States Patent
Xu et al.

(10) Patent No.: US 12,195,517 B2
(45) Date of Patent: Jan. 14, 2025

(54) RECOMBINANT VIRAL VECTOR, IMMUNE COMPOSITION CONTAINING SAME, AND USE THEREOF

(71) Applicant: VACDIAGN BIOTECHNOLOGY CO., LTD, Suzhou (CN)

(72) Inventors: Jianqing Xu, Suzhou (CN); Yang Huang, Suzhou (CN); Xiaoyan Zhang, Suzhou (CN); Lu Wang, Suzhou (CN); Mingquan Gao, Suzhou (CN); Jiahao Sun, Suzhou (CN)

(73) Assignee: VACDIAGN BIOTECHNOLOGY CO., LTD, Jiangsu (CN)

( * ) Notice: Subject to any disclaimer, the term of this patent is extended or adjusted under 35 U.S.C. 154(b) by 902 days.

(21) Appl. No.: 17/280,803

(22) PCT Filed: Jun. 12, 2019

(86) PCT No.: PCT/CN2019/090877
§ 371 (c)(1),
(2) Date: Mar. 26, 2021

(87) PCT Pub. No.: WO2020/062930
PCT Pub. Date: Apr. 2, 2020

(65) Prior Publication Data
US 2022/0002750 A1    Jan. 6, 2022

(51) Int. Cl.
| | | |
|---|---|---|
| *C07K 14/73* | (2006.01) | |
| *A61K 39/00* | (2006.01) | |
| *A61K 39/02* | (2006.01) | |
| *A61K 39/12* | (2006.01) | |
| *A61K 39/145* | (2006.01) | |
| *A61K 39/245* | (2006.01) | |

(Continued)

(52) U.S. Cl.
CPC ............ *C07K 14/70514* (2013.01); *A61K 39/001184* (2018.08); *A61K 39/001186* (2018.08); *A61K 39/001188* (2018.08); *A61K 39/107* (2013.01); *A61K 39/12* (2013.01); *A61K 39/145* (2013.01); *A61K 39/245* (2013.01); *A61P 31/04* (2018.01); *A61P 31/16* (2018.01); *A61P 31/20* (2018.01); *A61P 31/22* (2018.01); *A61P 35/00* (2018.01); *C07K 14/005* (2013.01); *C12N 7/00* (2013.01); *C12N 15/86* (2013.01); *A61K 2039/5256* (2013.01); *A61K 2039/53* (2013.01); *A61K 2039/575* (2013.01); *C07K 2319/00* (2013.01); *C12N 2710/16122* (2013.01); *C12N 2710/16134* (2013.01); *C12N 2710/24043* (2013.01); *C12N 2760/16022* (2013.01); *C12N 2760/16034* (2013.01)

(58) Field of Classification Search
CPC ............ C07K 14/70514; C07K 14/005; C07K 2319/00; C07K 2319/40; C07K 14/4748; A61K 39/001184; A61K 39/001186; A61K 39/001188; A61K 39/107; A61K 39/12; A61K 39/145; A61K 39/245; A61K 2039/5256; A61K 2039/53; A61K 2039/575; A61K 2039/6031; A61K 39/39; A61K 2039/55516; A61K 2039/57; A61P 31/04; A61P 31/16; A61P 31/20; A61P 31/22; A61P 35/00; A61P 31/14; C12N 7/00; C12N 15/86; C12N 2710/16122; C12N 2710/16134; C12N 2710/24043; C12N 2760/16022; C12N 2760/16034; C12N 2760/16134; C12N 2770/32334; C12N 2710/24143

See application file for complete search history.

(56) References Cited

U.S. PATENT DOCUMENTS

| | | | |
|---|---|---|---|
| 2005/0221381 A1* | 10/2005 | Klade | ............. C07K 14/005 |
| | | | 435/7.1 |
| 2010/0040614 A1* | 2/2010 | Ahmed | ............. A61P 31/16 |
| | | | 424/173.1 |

(Continued)

FOREIGN PATENT DOCUMENTS

| | | |
|---|---|---|
| CN | 1659436 A | 8/2005 |
| CN | 101579527 A | 11/2009 |

(Continued)

OTHER PUBLICATIONS

Sijmons S, Thys K, Mbong Ngwese M, Van Damme E, Van Loock M, Aerssens J, Van Ranst M., Maes P. Tegument protein pp65 [Human betaherpesvirus 5]. GenBank: AKI22339.1. May 27, 2015. (Year: 2015).*

(Continued)

*Primary Examiner* — Rachel B Gill
(74) *Attorney, Agent, or Firm* — Christensen O'Connor Johnson Kindness PLLC

(57) ABSTRACT

The present invention provides a recombinant viral vector, an immunogenic composition containing the same, and the use thereof. The recombinant viral vector comprises a polynucleotide encoding a fusion peptide of CD4 helper T cell epitopes, the epitope fusion peptide comprising a cytomegalovirus epitope and/or an influenza virus epitope. The epitope fusion peptide and the recombinant viral vector provided by the present invention can improve the level of cellular immune response to a target immunogen, particularly to a weak immunogen, and overcome the immune tolerance of immune system to an antigen, particularly to a tumor antigen or an infection-related antigen. The products of the present invention are suitable for enhancing the efficacy of vaccines.

12 Claims, 19 Drawing Sheets
Specification includes a Sequence Listing.

(51) Int. Cl.
   *A61P 31/04*    (2006.01)
   *A61P 31/16*    (2006.01)
   *A61P 31/20*    (2006.01)
   *A61P 31/22*    (2006.01)
   *A61P 35/00*    (2006.01)
   *C07K 14/005*   (2006.01)
   *C12N 7/00*     (2006.01)
   *C12N 15/86*    (2006.01)

(56) References Cited

U.S. PATENT DOCUMENTS

| | | | |
|---|---|---|---|
| 2010/0285982 A1* | 11/2010 | Golding | A61K 39/12 435/7.1 |
| 2010/0316667 A1* | 12/2010 | Diamond | C07K 14/005 435/235.1 |

FOREIGN PATENT DOCUMENTS

| | | |
|---|---|---|
| CN | 101652385 A | 2/2010 |
| CN | 102600466 A | 7/2012 |
| WO | 2008/157419 A2 | 12/2008 |
| WO | 2011/046996 A2 | 4/2011 |
| WO | 2013/093512 A3 | 6/2013 |
| WO | 2013/093514 A3 | 6/2013 |

OTHER PUBLICATIONS

Chen L, Zanker D, Xiao K, Wu C, Zou Q, Chen W. Immunodominant CD4+ T-cell responses to influenza A virus in healthy individuals focus on matrix 1 and nucleoprotein. J Virol. Oct. 2014;88(20):11760-73. Epub Jul. 30, 2014. (Year: 2014).*

Knowlden ZAG, Richards KA, Moritzky SA, Sant AJ. Peptide Epitope Hot Spots of CD4 T Cell Recognition Within Influenza Hemagglutinin During the Primary Response to Infection. Pathogens. Nov. 5, 2019;8(4):220. (Year: 2019).*

Spiro D, et. al. Hemagglutinin [Influenza A virus (A/Taiwan/5072/1999(H1N1))]. GenBank: ACR15304.1, Dep. May 18, 2009. (Year: 2009).*

Influenza A virus (A/Taiwan/5072/1999(H1N1)) whole genome segments 1-8, complete sequences. GenBank: CY040138.1-CY040145.1, Dep. May 18, 2009. (Year: 2009).*

Nayak, J.L., et al., "Analyses of the Specificity of CD4 T Cells During the Primary Immune Response to Influenza Virus Reveals Dramatic MHC-Linked Asymmetries in Reactivity to Individual Viral Proteins," Viral Immunology 23(2):169-180, Dec. 2010.

Richards, K.A., et al., "The Memory Phase of the CD4 T-Cell Response to Influenza Virus Infection Maintains its Diverse Antigen Specificity," Immunology 133:246-256, Dec. 2011.

International Search Report, mailed Dec. 29, 2018, based on International Application No. PCT/CN2018/108331, filed Sep. 28, 2018, 4 pages.

International Search Report, mailed Sep. 20, 2019, based on International Application No. PCT/CN2019/090877, filed Jun. 12, 2019, 4 pages.

* cited by examiner

1: pVKD1.0-hLMN
2: pVKD1.0-hLMN (Sal I+Bam HI)
3: DNA marker (Takara, DL10000)

1: pVKD1.0-hLMN-CTB
2: pVKD1.0-hLMN-CTB (Sal I+Bam HI)
3: DNA marker (Takara, DL10000)

1: pVKD1.0-CI (Pst I+Bgl II)
2: pVKD1.0-CI
3: DNA marker (Takara, DL2000)
4: DNA marker (Takara, DL10000)

Big band: 4325bp
Small band: 708bp

1: pVKD1.0-CI-LMNB (Bam HI+EcoR V)
2: pVKD1.0-CI-LMNB
3: DNA marker (Takara, DL10000)

Big band: 5006bp
Small band: 2506bp

1: pET-30a(+)-LMN (Nco I+Xho I)
2: pET-30a(+)-LMN
3: M2000
4: M10000

1: M10000
2: pET-30a(+)-CMV10-LMNB (Bam HI+Xho I)
3: pET-30a(+)-CMV10-LMNB

Big band: 5382bp
Small band: 2988bp

1: M10000
2: pET-30a(+)-Influ8-LMNB
3: pET-30a(+)-Influ8-LMNB(BamH I+Xho I)

Big band: 5382bp
Small band: 2961bp

1: M10000

2: pET-30a(+)-Influ13-LMNB (double enzyme digestion)

3: pET-30a(+)-Influ13-LMNB

Big band: 5382bp
Small band: 3207bp

RECOMBINANT VIRAL VECTOR, IMMUNE COMPOSITION CONTAINING SAME, AND USE THEREOF

TECHNICAL FIELD

The present invention belongs to the fields of molecular biology and immunology. In particular, the present invention relates to a recombinant viral vector comprising a polynucleotide encoding a fusion peptide of CD4 helper T cell epitopes, an immunogenic composition comprising the same, and use thereof.

BACKGROUND ART

T helper cells (Th cells) are the T cells that play an important role in the immune system, particularly in the adaptive immune system. They promote the activities of other immune cells by releasing T cell cytokines. These cells help to inhibit or modulate immune responses. They are essential in the conversion of B cell antibody classes, the activation and growth of cytotoxic T cells, and the maximization of bactericidal activity of phagocytic cells, such as macrophages.

Mature Th cells expressing the protein CD4 are known as $CD4^+$ T cells. As helper T cells, such $CD4^+$ T cells are typically subjected to a pre-defined process within the immune system. For example, when antigen presenting cells express an antigen on MHC class II, $CD4^+$ cells would assist these cells by a combination of cell-to-cell interactions (e.g., CD40 (protein) and CD40L) and cytokines.

The importance of helper T cells can be seen with respect to HIV, a virus that primarily infects $CD4^+$ T cells. In the late stage of HIV infection, loss of functional $CD4^+$ T cells leads to a stage of infectious symptoms known as acquired immune deficiency syndrome (AIDS). When HIV virus is found early in blood or other body fluids, a continuous treatment may delay its occurrence. If AIDS occurs, the treatment can also better manage the course of AIDS. Other rare diseases, such as lymphopenia, result in loss or dysfunction of $CD4^+$ T cells. These diseases produce similar symptoms, many of which are fatal.

Antigenic epitope, "epitope" for short, also known as "antigenic determinant", refers to chemical groups on the surface of an antigen that determines the antigen specificity. An antigenic epitope can be recognized by the immune system, especially by antibodies, B cells or T cells. A site of an antibody capable of recognizing an antigenic epitope is referred to as a "paratope" or an "antibody determinant". Although an antigenic epitope usually refers to a part of foreign protein or the like, an epitope that can be recognized by the autoimmune system is also classified as an antigenic epitope.

The epitopes of protein antigen are divided into conformational epitopes and linear epitopes according to their structures and interactions with a paratope. Since a conformational epitope consists of discrete portions in the amino acid sequence of an antigen, the interaction of a paratope with the antigenic epitope is based on the three-dimensional characteristics and shape of the surface or tertiary structure of the antigen. Most antigenic epitopes belong to conformational epitopes. In contrast, a linear epitope consists of a continuous amino acid sequence of an antigen, and the interaction with the antigen is based on its primary structure.

A T cell epitope consists mainly of a short peptide of 8-17 amino acids and exists on antigen-presenting cells (APC), which as an antigen epitope would bind to major histocompatibility complex (MHC) to form a complex and bind to the corresponding T cell epitope receptors, thereby activating T cells and generating a corresponding cellular immune response (Shimonikevitz et al., 1984; Babbitt et al., 1985; Buus et al., 1986; Townsend and Bodmer, 1989). There are two major classes of MHC molecules which bind to an epitope. Among them, major histocompatibility complex class I usually presents a T cell antigenic epitope consisting of a polypeptide of 8 to 11 amino acids in length, while major histocompatibility complex class II presents a relatively longer T cell antigenic epitope consisting of 13-17 amino acids.

Among T cell epitopes, helper T cell epitopes (Th epitopes) refer to a class of T cell epitopes which bind to MHC molecules and form complexes that can be recognized by CD4 helper T cell receptors. Th epitopes bind primarily to the molecules present on the surfaces of antigen-presenting cells (APC) encoded by major histocompatibility complex (MHC) class II genes. The complexes of class II molecule and peptide epitope are then recognized by the specific T cell receptors (TCR) on the surfaces of T helper lymphocytes. In this way, the T cells presenting an antigenic epitope in the context of MHC molecules can be activated and provide the essential signal for B lymphocyte differentiation. Traditionally, the source of T-helper epitope of peptide immunogen has been a carrier protein covalently coupled to a peptide, but the coupling process may involve other issues, such as modification of antigenic determinants during the coupling process and induction of an antibody against the carrier at the expense of an antibody against the peptide (Schutze, M. P., Leclerc, C. Jolivet, M. Audibert, F. Chedid, L. Carrier-induced epitopic suppression, a major issue for future synthetic vaccines. J Immunol. 1985, 135, 2319-2322; DiJohn, D., Torrese, J. R. Murillo, J. Herrington, D. A. et al. Effect of priming with carrier on response to conjugate vaccine. The Lancet. 1989, 2, 1415-1416). In addition, the use of an irrelevant protein in the preparation may involve quality control problems. The choice of a suitable carrier protein, which is important in the design of peptide vaccine, is limited by the factors, such as toxicity and feasibility in a large-scale production. There are other limitations to this method, including the load size of peptide that can be coupled and the dose of carrier that can be safely administered (Audibert, F. a. C., L. 1984. Modern approaches to vaccines. Molecular and chemical basis of virus virulence and immunogenicity., Cold Spring Harbor Laboratory, New York.). Although carrier molecules allow to induce a strong immune response, they are also associated with the adverse effects, such as inhibition of anti-peptide antibody response (Herzenberg, L. A. and Tokuhisa, T. 1980. Carrier-priming leads to hapten-specific suppression. Nature 285: 664; Schutze, M. P., Leclerc, C., Jolivet, M., Audibert, F., and Chedid, L. 1985. Carrier-induced epitopic suppression, a major issue for future synthetic vaccines. J Immunol 135: 2319; Etlinger, H. M., Felix, A. M., Gillessen, D., Heimer, E. P., Just, M., Pink, J. R., Sinigaglia, F., Sturchler, D., Takacs, B., Trzeciak, A., and et al., 1988. Assessment in humans of a synthetic peptide-based vaccine against the sporozoite stage of the human malaria parasite, *Plasmodium falciparum*. J Immunol 140: 626).

In general, an immunogen must contain a helper T cell epitope in addition to an epitope to be recognized by a surface Ig or the receptors present on the cytotoxic T cells. It will be appreciated that these types of epitopes may be very different. For B-cell epitopes, the conformation is important because B-cell receptors bind directly to native immunogens. In contrast, an epitope to be recognized by T cells is independent of the conformational integrity of the epitope, and consists of a short sequence of about 9 amino acids against CTL and a slightly longer sequence (having less length restriction) against helper T cells. The only requirement for these epitopes is that they can be accommodated in the binding clefts of class I or class II molecules, respectively, and the complexes can then bind to T cell receptors. The binding sites of class II molecules are open at both ends, allowing a greater variation in the length of a peptide (Brown, J. H., T. S. Jardetzky, J. C. Gorga, L. J. Stern, R. G. Urban, J. L. Strominger and D. C. Wiley. 1993. Three-dimensional structure of the human class II histocompatibility antigen HLA-DR1. Nature 364: 33) that binds to a reported epitope of as short as 8 amino acid residues (Fahrer, A. M., Geysen, H. M., White, D. O., Jackson, D. C. and Brown, L. E. Analysis of the requirements for class II-restricted T-cell recognition of a single determinant reveals considerable diversity in the T-cell response and degeneracy of peptide binding to HEd J. Immunol. 1995. 155: 2849-2857).

A Th epitope can stimulate and activate helper T cells, and accordingly promote activation of CD8 T cells and B cells, ultimately increasing the immune response. In essence, a Th epitope, in addition to being able to activate an immune response against itself, is also effective in aiding the immune response to other antigens or epitopes associated therewith. Thus, a heterologous strong Th epitope can be fused to a target immunogen, thereby increasing the immunogenicity of the target immunogen. An artificial strong Th epitope called PADRE (pan HLA DR-binding Epitope) has been used in the fusion construction of multiple vaccines to increase the levels of immune responses to the relevant immunogens (del Guercio et al., Vaccine, 1997, 15: 441.; Franke, E. D. et al., Vaccine, 1999, 17:1201; Jeff Alexander et al., J Immunol, 2000, 164(3) 1625-1633; Jeff Alexander et al., Vaccine, 2004, 22: 2362.; La Rosa, Corinna et al., The Journal of infectious diseases, 2012, 205: 1294-304). In addition, as a strong Th epitope derived from tetanus toxin, P2 is also commonly used in coupling with a target immunogen to enhance the immunogenicity (Panina-Bordignon P et al., Eur J Immunol, 1989, 19: 2237-42; La Rosa, Corinna et al., The Journal of infectious diseases, 2012, 205: 1294-304).

In general, however, a Th epitope used to increase the immunogenicity is usually heterologous. In other words, a high level of immune response against the Th epitope itself will not be produced in a vaccine subject. Thus, when a vaccine subject is vaccinated with a strong Th epitope as described above, it is likely that the immune system of vaccine subject is initially exposed to such a Th epitope, the activations against both such a Th epitope and a target immunogen in the recipient immune system are substantially synchronized, and the generation time and numbers of T cells against such a Th epitope are similar to those against the target immunogen. In this way, the effect on assisting the target immunogen will be limited, accordingly. Especially for a weakly immunogenic tumor antigen, the helping effect of such a Th epitope is more difficult to exert. Indeed, the direct use of a strong Th epitope, although being capable of activating a tumor antigen, elicits a lower level of cellular immune response that do not meet the needs of a tumor vaccine (Ghaffari-Nazari H et al., PLoS ONE, 2015, 10(11): e0142563).

Thus, new Th epitope strategies are needed to enhance the immunogenicities of target immunogens, particularly some weak immunogens, such as tumor antigens.

DISCLOSURE OF THE INVENTION

It is an object of the present invention to provide a fusion peptide of CD4 helper T cell epitopes, by which the immunogenicity of a target immunogen is enhanced.

Further, the present invention utilizes strong Th epitopes derived from cytomegalovirus (CMV) and influenza (Flu) virus (influvirus) to obtain an epitope fusion peptide for enhancing the immunogenicity of a target immunogen.

For the purposes of the present invention, the following terms are defined below.

"Epitope fusion peptide" refers to a peptide formed by joining together several epitopes.

"Target immunogen" refers to an immunogen used for achieving a certain immune response, including a substance having an immunological activity, such as an antigen, preferably a protein.

It is another object of the present invention to provide a fusion protein of the epitope fusion peptide and a target immunogen.

To achieve the above objects, the present invention provides a fusion peptide of CD4 helper T cell epitopes, comprising a cytomegalovirus epitope and/or an influenza virus epitope. The present invention also provides a recombinant viral vector comprising a polynucleotide encoding a fusion peptide of CD4 helper T cell epitopes, the fusion peptide of CD4 helper T cell epitopes comprising a cytomegalovirus epitope and/or an influenza virus epitope.

In one embodiment of the present invention, the epitope fusion peptide comprises one or more of cytomegalovirus epitopes selected from those shown in SEQ ID NOs: 1-10, and/or one or more of influenza virus epitopes selected from those shown in SEQ ID NOs: 11-23.

In one embodiment of the present invention, the epitope fusion peptide consists of one or more of cytomegalovirus epitopes selected from those shown in SEQ ID NOs: 1-10, and/or one or more of influenza virus epitopes selected from those shown in SEQ ID NOs: 11-23. Preferably, the epitope fusion peptide consists of 5 or 10 cytomegalovirus epitopes, and/or 8 or 13 influenza virus epitopes, such as the epitope fusion peptide shown in SEQ ID NO: 34 or 44. Most preferably, the epitope fusion peptide consists of 13 influenza virus epitopes, such as the epitope fusion peptide shown in SEQ ID NO: 48 or 60.

Preferably, the epitope fusion peptide induces a humoral or cellular immune response.

Preferably, the recombinant virus vector is a vaccinia virus vector, preferably a replicative vaccinia viral vector, e.g. the vaccinia virus Tiantan strain, e.g. Strain 752-1, or a non-replicative vaccinia viral vector, e.g. the vaccinia virus attenuated vaccine Ankara strain (Modified Vaccinia Ankara, MVA).

The present invention also provides a fusion protein of the epitope fusion peptide and a target immunogen.

The present invention also provides a polynucleotide encoding the epitope fusion peptide and/or the fusion protein.

In one embodiment of the present invention, the target immunogen is any one or more immunogens. Preferably, the target immunogen is a peptide, an antigen, a hapten, a carbohydrate, a protein, a nucleic acid, an allergen, a virus or a part of a virus, a bacterium, a parasite or other whole microorganism.

In one embodiment of the present invention, the antigen is a tumor antigen or an infection-related antigen.

In one embodiment of the present invention, the tumor antigen is one or more tumor antigens selected from lung cancer antigen, testicular cancer antigen, melanoma antigen, liver cancer antigen, breast cancer antigen or prostate cancer antigen.

In one embodiment of the present invention, the tumor antigen is one or more tumor antigens selected from LAGE antigen, MAGE antigen, or NY-ESO-1 antigen. Preferably, the LAGE antigen is LAGE-1, and the MAGE antigen is MAGE-A3. Further preferably, the tumor antigen comprises LAGE-1, MAGE-A3, and NY-ESO-1. Preferably, the amino acid sequence of LAGE-1 is shown in SEQ ID NO: 24, the amino acid sequence of MAGE-A3 is shown in SEQ ID NO: 25, and the amino acid sequence of NY-ESO-1 is shown in SEQ ID NO: 26. Still further preferably, the tumor antigen comprises LAGE-1, MAGE-A3, and NY-ESO-1.

In one embodiment of the present invention, the infection-related antigen is one or more infection-related antigen selected from an HIV antigen, a Flu virus antigen or an HBV antigen.

Preferably, the fusion protein is shown in one of SEQ ID NOs: 55-58 and 62.

Preferably, the gene encoding the fusion protein is shown in SEQ ID NO: 63.

Another object of the present invention is to provide an immunogenic composition comprising a therapeutically effective amount of the epitope fusion peptide, the fusion protein, the polynucleotide and/or the recombinant viral vector according to the present invention, and a pharmaceutically acceptable carrier. Preferably, the immunogenic composition is a vaccine.

It is another object of the present invention to provide a kit comprising the epitope fusion peptide, the fusion protein, the polynucleotide, the recombinant viral vector and/or the immunogenic composition according to the present invention, and instructions for use thereof.

The present invention also provides use of the epitope fusion peptide, the fusion protein, the polynucleotide, the recombinant viral vector and/or the immunogenic composition according to the present invention in the manufacture of a medicament or a vaccine for increasing the immunogenicity of a target immunogen.

The present invention also provides a method for increasing the immunogenicity of a target immunogen using the epitope fusion peptide according to the present invention, comprising fusing a CD4 helper T cell epitope having a stronger immune response in a vaccine subject or population with a target immunogen to form a fusion protein. The method specifically comprises the following steps of:

(1) selecting one or more CD4 helper T cell epitopes, wherein a complex formed by combining the epitopes with MHC molecules can be recognized by CD4 helper T cell receptors, and a T cell immune response has been generated against at least one of the epitopes in a vaccine subject before vaccination;

(2) fusing the epitopes to prepare an epitope fusion peptide, fusing the epitope fusion peptide with a target immunogen to prepare a fusion protein, expressing the fusion protein and preparing it into a vaccine, wherein the expression vector can be in the form of a DNA vaccine vector, a protein vaccine vector, or a virus vaccine vector; and (3) vaccinating the vaccine subject with the above vaccine, and a suitable adjuvant, such as incomplete Freund's adjuvant, complete Freund's adjuvant, or aluminum hydroxide adjuvant and the like can be selected for vaccination.

Further, step (1) in the method further comprises a step of examining the MHC phenotype of the vaccine subject.

Preferably, examining the MHC phenotype of the vaccine subject comprises examining the MHC class II gene subtype of the vaccine subject.

The present invention also provides a method for treating or preventing a condition in a subject in need thereof, comprising administering a therapeutically effective amount of the epitope fusion peptide, the immunogenic composition, the polynucleotide and/or the recombinant viral vector of the present invention. Preferably, the condition is one or more conditions selected from malignant tumors, and bacterial and viral infections. Preferably, the malignant tumor is breast cancer or colon cancer. Preferably, the infection is a chronic infection. Preferably, in the method, the DNA vaccine vector is used for the prime immunization, and a protein vaccine vector is used for the boost immunization. More preferably, the pVKD1.0-CI-LMNB DNA vaccine is used for the prime immunization, and the LMNB-I13 protein is used for the boost immunization.

The epitope fusion peptide provided by the present invention can substantially improve the level of cellular immune response to a target immunogen, particularly to a weak immunogen, and is an effective means for overcoming the immune tolerance of immune system to an antigen, particularly to a tumor antigen or an infection-related antigen, and is suitable for efficiently enhancing the efficacy of vaccines.

BRIEF DESCRIPTION OF DRAWINGS

Hereinafter, the embodiments of the present invention will be described in detail with reference to the accompanying drawings, in which.

BEST MODES FOR CARRYING OUT THE INVENTION

The present invention is described in further detail below with reference to the specific embodiments. The examples are given for the purpose of illustration of the present invention only, and are not intended to limit the scope of the present invention.

Example 1 Construction of DNA Vaccine pVKD1.0-hLMN

The amino acid sequences of LAGE-1, MAGE-A3 and NY-ESO-1 are shown in SEQ ID NOs: 24-26, respectively.

Figure 1:
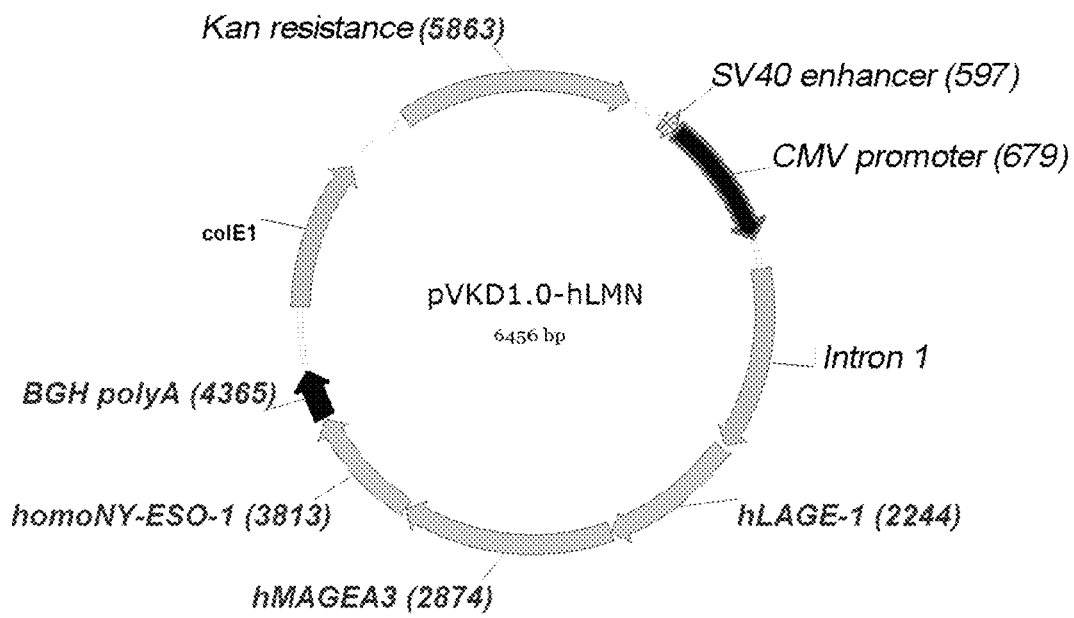
FIGS. 1 and 2 are a plasmid map and a map of double enzyme digestion for identification of the DNA vaccine vector pVKD1.0-hLMN carrying the encoding sequences of LAGE-1, MAGE-A3 and NY-ESO-1 antigens, respectively.
Figure 2:
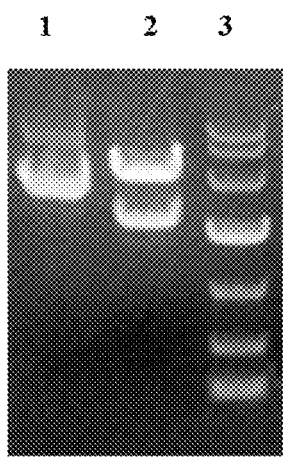

By means of an online codon optimization software, the nucleotide sequences for mammalian codon usage preference as shown in SEQ ID NOs: 27-29 respectively were obtained by optimization based on the above antigen amino acid sequences. The nucleotide sequences were synthesized by Shanghai Generay Biotech Co., Ltd., and then cloned between the multiple cloning sites Sal I and BamH I on the DNA vaccine vector pVKD1.0 (provided by Vacdiagn Biotechnology Co., Ltd., Suzhou Industrial Park) by a method well known in the art to construct the DNA vaccine vector pVKD1.0-hLMN capable of expressing the fusion protein as an antigen (the plasmid map is shown in FIG. 1), which was stored after being sequenced for identification. The vector pVKD1.0-hLMN was identified by the restriction endonucleases Sal I and BamH I (the enzyme digestion system is shown in Table 1), and its enzyme digestion map for verification is shown in FIG. 2.

TABLE 1

| Enzyme digestion system for identification of the plasmid pVKD1.0-hLMN (enzyme digestion at 37° C., 2 h) | |
|---|---|
| Enzyme digestion system | Volume |
| Plasmid pVKD1.0-hLMN | 3 μL, about 1 μg |
| Sal I (Takara, Cat. No. 1080A) | 1 μL |
| BamH I (Takara, Cat. No. 1010A) | 1 μL |
| Enzyme digestion buffer | 1 μL |
| ddH$_2$O | q.s. to 10 μL |

Example 2 Construction of DNA Vaccine pVKD1.0-hLMN-CTB

Figure 3:
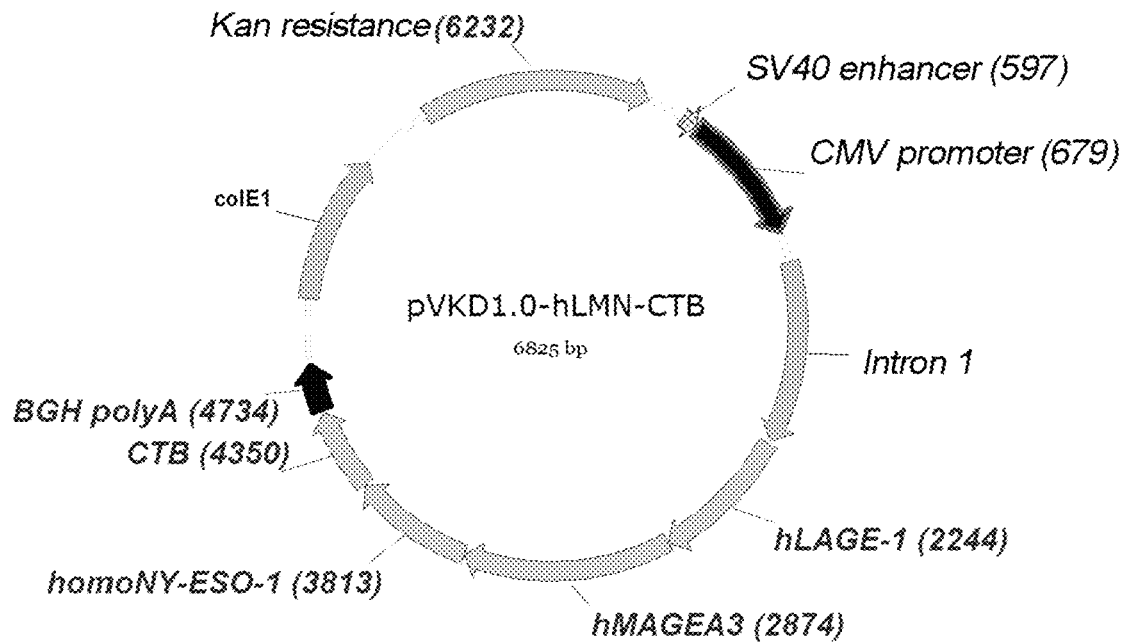
FIGS. 3 and 4 are a plasmid map and a map of double enzyme digestion for identification of the DNA vaccine vector pVKD1.0-hLMN-CTB carrying the encoding sequences of LAGE-1, MAGE-A3 and NY-ESO-1 antigens and cholera toxin subunit B, respectively.
Figure 4:
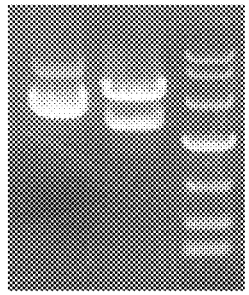

The mammalian codon optimized sequence (SEQ ID NO: 31) of the amino acid sequence (SEQ ID NO: 30) of cholera toxin subunit B (CTB) and its eukaryotic expression vector pVKD1.0-CTB were provided by Vacdiagn Biotechnology Co., Ltd., Suzhou Industrial Park. The primers were designed by using pVKD1.0-CTB as a template (Table 2). The CTB gene fragment was amplified by PCR, and the corresponding fragment was then recovered from the gel. The CTB fragment was inserted into a corresponding position on the linearized vector pVKD1.0-hLMN by a homologous recombination method, to construct the DNA vaccine vector pVKD1.0-hLMN-CTB (the plasmid map is shown in FIG. 3), which was stored after being sequenced for identification. The vector pVKD1.0-hLMN-CTB was identified by the restriction endonucleases Sal I and BamH I (the enzyme digestion system is shown in Table 3), and its enzyme digestion map for verification is shown in FIG. 4.

TABLE 2

| Primers in Example 2 | | |
|---|---|---|
| Primer | | Sequence |
| 1F (SEQ ID NO: 32) | | TCCCTCAGGGCAGAGGCGCATCAAGCTGAAGTTCGGCGTG |
| 1R (SEQ ID NO: 33) | | GAAGGCACAGCAGATCTGGATCCTCAGTTGGCCATGCTGATGGC |

TABLE 3

Enzyme digestion system for identification of plasmid pVKD1.0-hLMN-CTB (enzyme digestion at 37° C., 2 h)

| Enzyme digestion system | Volume |
| --- | --- |
| Plasmid pVKD1.0-hLMN-CTB | 3 μL, about 1 μg |
| Sal I (Takara, Cat. No. 1080A) | 1 μL |
| BamH I (Takara, Cat. No. 1010A) | 1 μL |
| Enzyme digestion buffer | 1 μL |
| ddH$_2$O | q.s. to 10 μL |

Example 3 Construction of DNA Vaccine pVKD1.0-CI-LMNB

Figure 5:
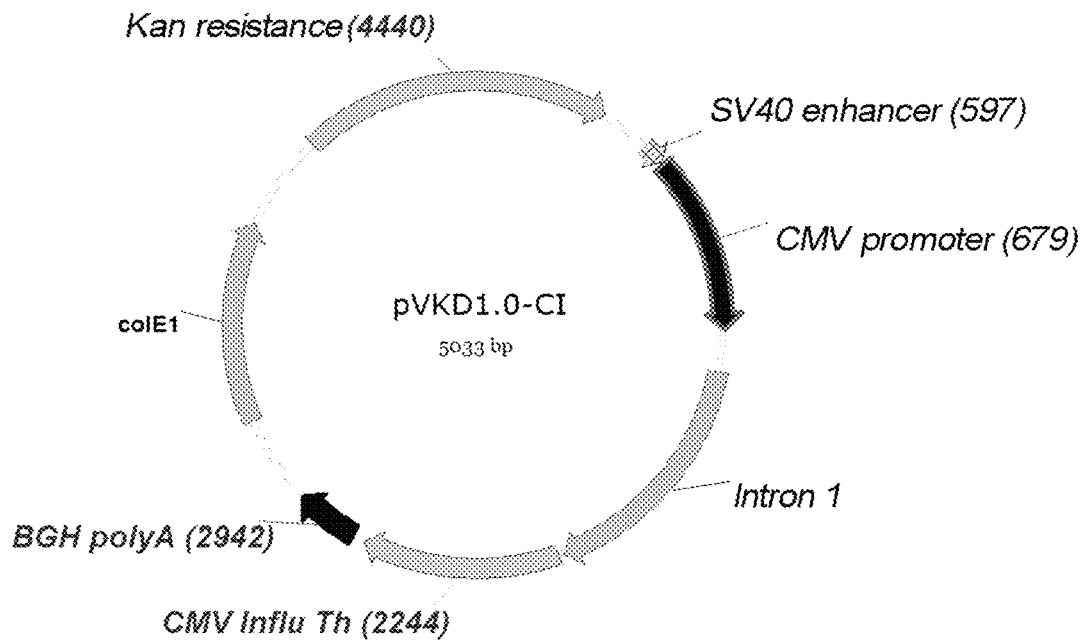
FIGS. 5 and 6 are a plasmid map and a map of double enzyme digestion for identification of the DNA vaccine vector pVKD1.0-CI carrying the encoding sequences of CMV and Flu virus-derived CD4 epitopes, respectively.
Figure 6:
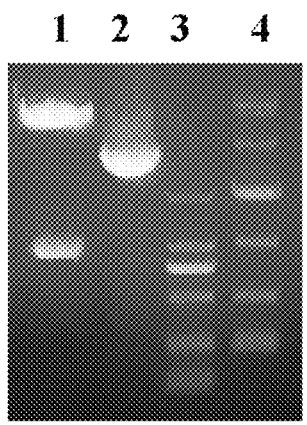

The strong Th epitopes derived from cytomegalovirus (CMV) and influenza (Flu) virus (see Table 4) were obtained from an immune epitope database (IEDB), wherein the strong Th epitopes of CMV include pp65-11, pp65-71, pp65-92, pp65-123, pp65-128, pp65-57, pp65-62, pp65-30, pp65-112 and pp65-104, and the strong Th epitopes of Flu virus include HA203, NP438, NS1-84, M1-181, HA375, NP24, NP95, NP221, HA434, HA440, NP324, M1-127 and M1-210. The selected epitopes in Table 4 cover most subtypes of MHC class II molecules in both human and mouse. The selected epitopes pp65-11, pp65-71, pp65-92, pp65-123, pp65-128, HA203, NP438, NS1-84, M1-181, HA375, NP24, NP95, and NP221 were then linked together in tandem to form an fusion peptide of CMV virus epitopes and Flu virus epitopes having the amino acid sequence shown in SEQ ID NO: 34. The epitope fusion peptide was subjected to mammal codon optimization to give the nucleic acid sequence shown in SEQ ID NO: 35, which was sent to Suzhou Synbio Technologies Co., Ltd for synthesis, and then inserted into the DNA vaccine vector pVKD1.0 (Vacdiagn Biotechnology Co., Ltd., Suzhou Industrial Park) by a molecular biology method well known in the art to form the vector pVKD1.0-CI (the plasmid map is shown in FIG. 5), and stored after being sequenced for identification. The vector pVKD1.0-CI was identified by the restriction endonucleases Pst I and Bgl II (the enzyme digestion system is shown in Table 5) and its enzyme digestion map for verification is shown in FIG. 6.

TABLE 4

Th epitopes in Example 3

| Epitope Name | Source | Amino acid sequence |
| --- | --- | --- |
| pp65-11 | CMV | LLQTGIHVRVSQPSL (SEQ ID NO: 1) |
| pp65-71 | CMV | IIKPGKISHIMLDVA (SEQ ID NO: 2) |
| pp65-92 | CMV | EHPTFTSQYRIQGKL (SEQ ID NO: 3) |
| pp65-123 | CMV | AGILARNLVPMVATV (SEQ ID NO: 4) |
| pp65-128 | CMV | KYQEFFWDANDIYRI (SEQ ID NO: 5) |
| pp65-57 | CMV | KVYLESFCEDVPSGK (SEQ ID NO: 6) |
| pp65-62 | CMV | TLGSDVEEDLTMTRN (SEQ ID NO: 7) |
| pp65-30 | CMV | PLKMLNIPSINVHHY (SEQ ID NO: 8) |
| pp65-112 | CMV | ACTSGVMTRGRLKAE (SEQ ID NO: 9) |
| pp65-104 | CMV | TERKTPRVTGGGAMA (SEQ ID NO: 10) |
| HA203 | Influ | NQRALYHTENAYVSVVS (SEQ ID NO: 11) |
| NP438 | Influ | SDMRAEIIKMMESARPE (SEQ ID NO: 12) |
| NS1-84 | Influ | ALASRYLTDMTIEEMSR (SEQ ID NO: 13) |
| M1-181 | Influ | LASTTAKAMEQMAGSSE (SEQ ID NO: 14) |
| HA375 | Influ | SGYAADQKSTQNAINGITNKVN (SEQ ID NO: 15) |
| NP24 | Influ | EIRASVGKMIDGIGRFYI (SEQ ID NO: 16) |
| NP95 | Influ | PIYRRVDGKWMRELVLY (SEQ ID NO: 17) |
| NP221 | Influ | RMCNILKGKFQTAAQRAM (SEQ ID NO: 18) |
| HA434 | Influ | IWTYNAELLVLLENERT (SEQ ID NO: 19) |
| HA440 | Influ | ELLVLLENERTLDFHDS (SEQ ID NO: 20) |
| NP324 | Influ | HKSQLVWMACNSAAFED (SEQ ID NO: 21) |
| M1-127 | Influ | CMGLIYNRMGAVTTESA (SEQ ID NO: 22) |
| M1-210 | Influ | RQMVQAMRAIGTHPSSSTGLKND (SEQ ID NO: 23) |

TABLE 5

Enzyme digestion system for identification of plasmid pVKD1.0-CI (enzyme digestion at 37° C., 2 h)

| Enzyme digestion system | Volume |
| --- | --- |
| Plasmid pVKD1.0-CI | 3 μL, about 1 μg |
| Pst I (Takara, Cat. No. 1073A) | 1 μL |
| Bgl II (Takara, Cat. No. 1021A) | 1 μL |
| Enzyme digestion buffer | 1 μL |
| ddH$_2$O | q.s. to 10 μL |

Figure 7:
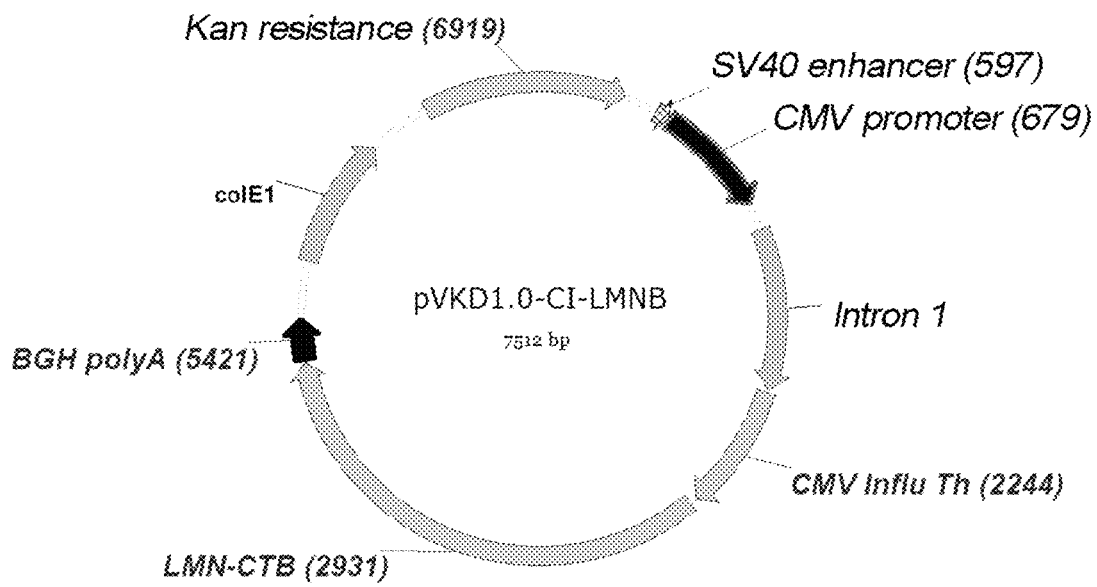
FIGS. 7 and 8 are a plasmid map and a map of double enzyme digestion for identification of the DNA vaccine vector pVKD1.0-CI-LMNB carrying the encoding sequences of LAGE-1, MAGE-A3 and NY-ESO-1 antigens, cholera toxin subunit B, and CMV and Flu virus-derived CD4 epitopes, respectively.
Figure 8:
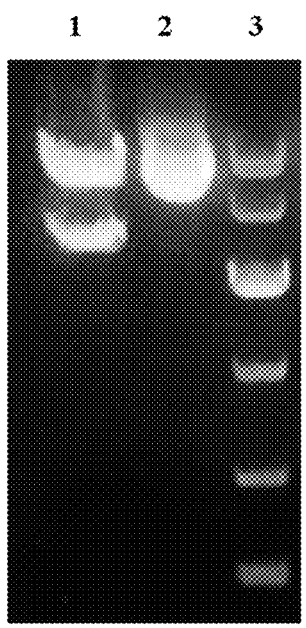

Finally, the primers were designed by using the vector pVKD1.0-hLMN-CTB in Example 2 as a template (Table 6). The target gene fragment hLMN-CTB was amplified by PCR, and then inserted between the restriction sites Not I and Bam HI on the pVKD1.0-CI vector by a molecular biology method well known in the art to construct the DNA vaccine vector pVKD1.0-CI-LMNB (the plasmid map is shown in FIG. 7), which was stored after being sequenced for identification. The vector pVKD1.0-CI-LMNB was identified by the restriction endonucleases Bam HI and EcoR V (the enzyme digestion system is shown in Table 7), and its enzyme digestion map for verification is shown in FIG. 8.

TABLE 6

Primers in Example 3

| Primer | Sequence |
| --- | --- |
| 3F (SEQ ID NO: 36) | GCGCGGCCGCTGTCACCGTCGTCGACATGCAGGCCGAA |
| 3R (SEQ ID NO: 37) | GCGATCCTCAGTTGGCCATGCTGATGGCGGCGATG |

TABLE 7

Enzyme digestion system for identification of plasmid pVKD1.0-CI-LMNB (enzyme digestion at 37° C., 2 h)

| Enzyme digestion system | Volume |
|---|---|
| Plasmid pVKD1.0-CI-LMNB | 3 μL, about 1 μg |
| Bam HI (Takara, Cat. No. 1010A) | 1 μL |
| EcoR V (Takara, Cat. No. 1042A) | 1 μL |
| Enzyme digestion buffer | 1 μL |
| ddH$_2$O | q.s. to 10 μL |

Example 4 Construction of LMN Prokaryotic Expression Vector

Figure 9:
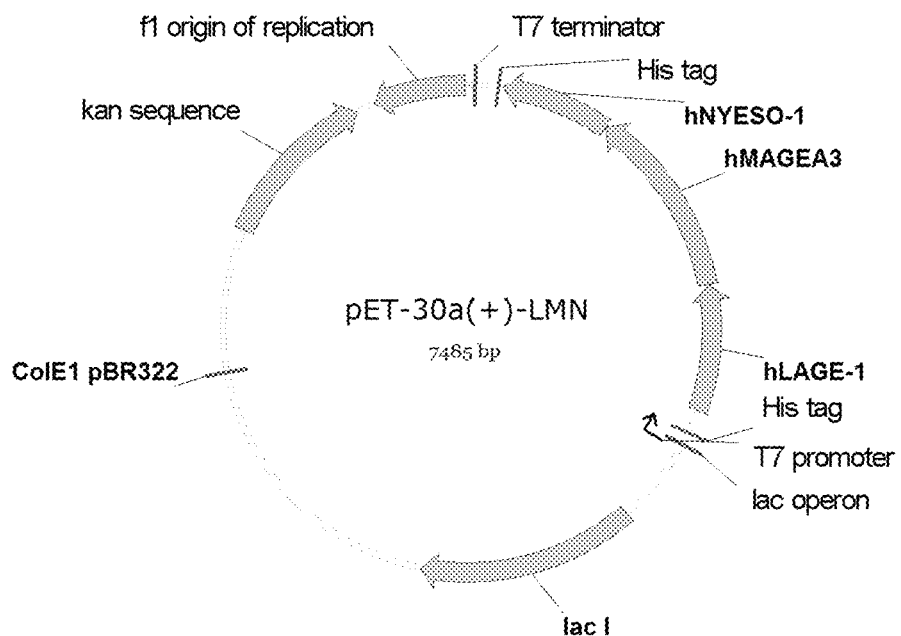
FIGS. 9 and 10 are a plasmid map and a map of double enzyme digestion for identification of the prokaryotic vector pET-30a(+)-LMN carrying the encoding sequences of LAGE-1, MAGE-A3 and NY-ESO-1 antigens, respectively.
Figure 10:
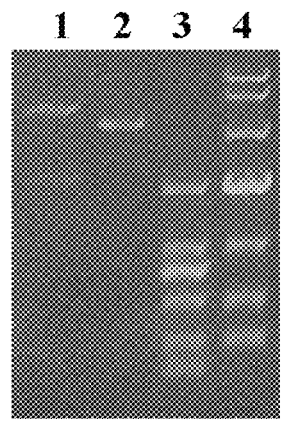

The amino acid sequences of LAGE-1, MAGE-A3 and NY-ESO-1 are shown in SEQ ID NOs: 24-26, respectively. By means of an online codon optimization software, the nucleotide sequences for *E. coli* codon usage preference shown in SEQ ID NOs: 38-40 respectively were obtained through optimization based on the antigen amino acid sequences. The nucleotide sequences were synthesized by Suzhou Synbio Technologies Co., Ltd., and then inserted between the multiple cloning sites Nco I and Xho I on the prokaryotic expression vector pET-30a (+) (Novagen, Cat. No. 69909) by a molecular biology method well known in the art to construct the prokaryotic expression construct pET-30a (+)-LMN (the plasmid map is shown in FIG. 9), which was stored after being sequenced for identification. The vector pET-30a (+)-LMN was identified by the restriction endonucleases Nco I and Xho I (the enzyme digestion system is shown in Table 8), and its enzyme digestion map for verification is shown in FIG. 10.

TABLE 8

Enzyme digestion system for identification of plasmid pET-30a(+)-LMN (enzyme digestion at 37° C., overnight)

| Enzyme digestion system | Volume |
|---|---|
| Plasmid pET-30a(+)-LMN | 3 μL, about 1 μg |
| Nco I (Takara, Cat. No. 1160A) | 1 μL |
| Xho I (Takara, Cat. No. 1094A) | 1 μL |
| Enzyme digestion buffer | 1 μL |
| ddH$_2$O | q.s. to 10 μL |

Example 5 Construction of LMN-CTB Prokaryotic Expression Vector

Figure 11:
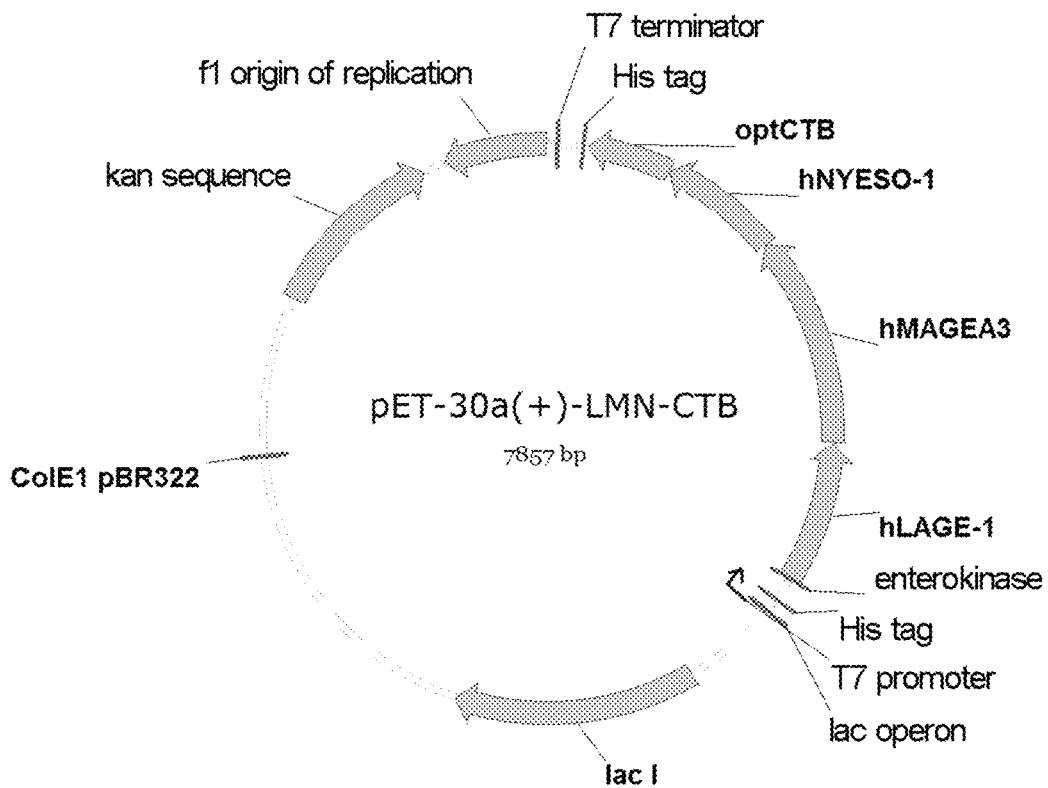
FIGS. 11 and 12 are a plasmid map and a map of double enzyme digestion for identification of the prokaryotic vector pET-30a(+)-LMN-CTB carrying the encoding sequences of LAGE-1, MAGE-A3 and NY-ESO-1 antigens and cholera toxin subunit B, respectively.
Figure 12:
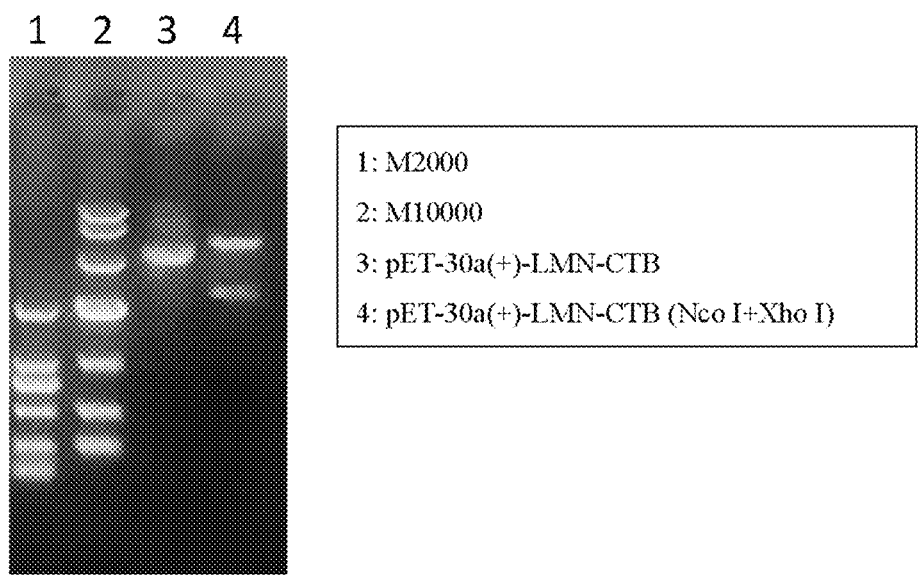

The amino acid sequence of cholera toxin subunit B (CTB) (SEQ ID NO: 30) and its prokaryotic codon optimized nucleic acid sequence (SEQ ID NO: 41) were provided by Vacdiagn Biotechnology Co., Ltd., Suzhou Industrial Park. The primers were designed (Table 9), and a nucleic acid fragment containing the CTB encoding sequence was amplified by a PCR method using the pET-30a(+)-CTB (Vacdiagn Biotechnology Co., Ltd., Suzhou Industrial Park) as a template, and the instructions of Ex Taq Enzyme Reagent (Takara, Cat. No. RR001B) were referred to for the specific method. The nucleic acid fragment was then inserted into the pET-30a(+)-LMN vector by means of homologous recombination to construct the pET-30a(+)-LMN-CTB vector (the plasmid map is shown in FIG. 11), which was stored after being sequenced for identification. The vector pET-30a(+)-LMN-CTB was identified by the restriction endonucleases Nco I and Xho I (the enzyme digestion system is shown in Table 10), and its enzyme digestion map for verification is shown in FIG. 12.

TABLE 9

Primers in Example 5

| Primer | Sequence |
|---|---|
| 5F (SEQ ID NO: 42) | GGTGGTGGTGGTGCTCGAGTTAGTTAGCCATAGAGA |
| 5R (SEQ ID NO: 43) | TCTGCGTGAAGGTGAAGAAGCTCAGGCTGAAGGTCGTGG |

TABLE 10

Enzyme digestion system for identification in Example 5 (enzyme digestion at 37° C., overnight)

| Enzyme digestion system | Volume |
|---|---|
| Plasmid pET-30a(+)-LMN-CTB | 3 μL, about 1 μg |
| Nco I (Takara, Cat. No. 1160A) | 1 μL |
| Xho I (Takara, Cat. No. 1094A) | 1 μL |
| Enzyme digestion buffer | 1 μL |
| ddH$_2$O | q.s. to 10 μL |

Figure 13:
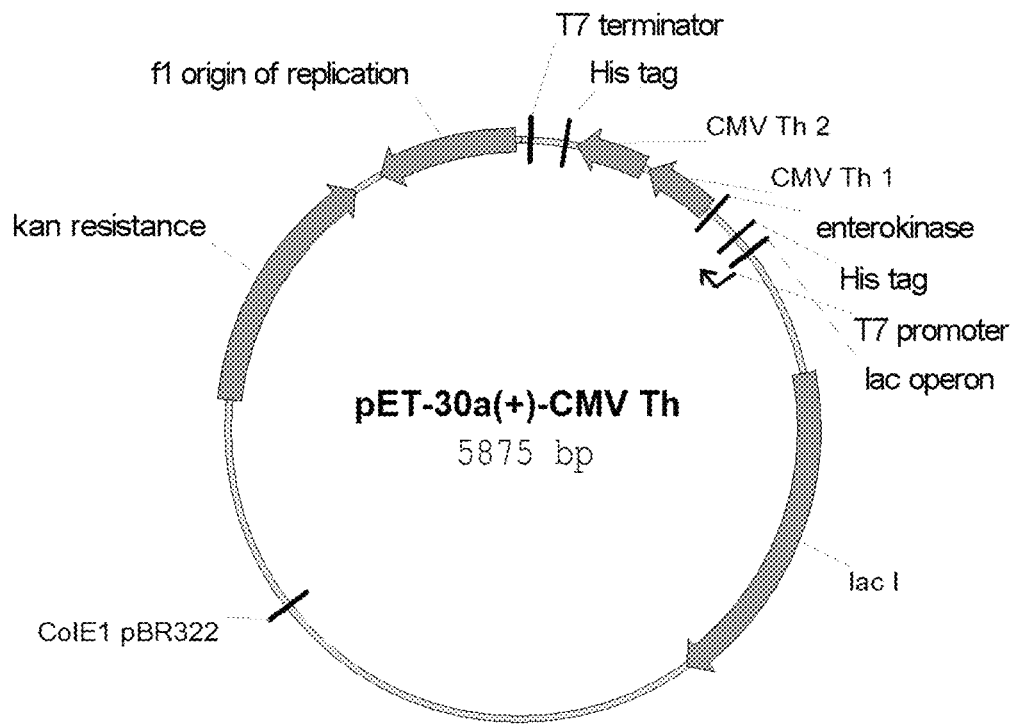
FIGS. 13 and 14 are a plasmid map and a map of double enzyme digestion for identification of the prokaryotic vector pET-30a(+)-CMV Th carrying the encoding sequence of a CMV-derived epitope, respectively.
Figure 14:
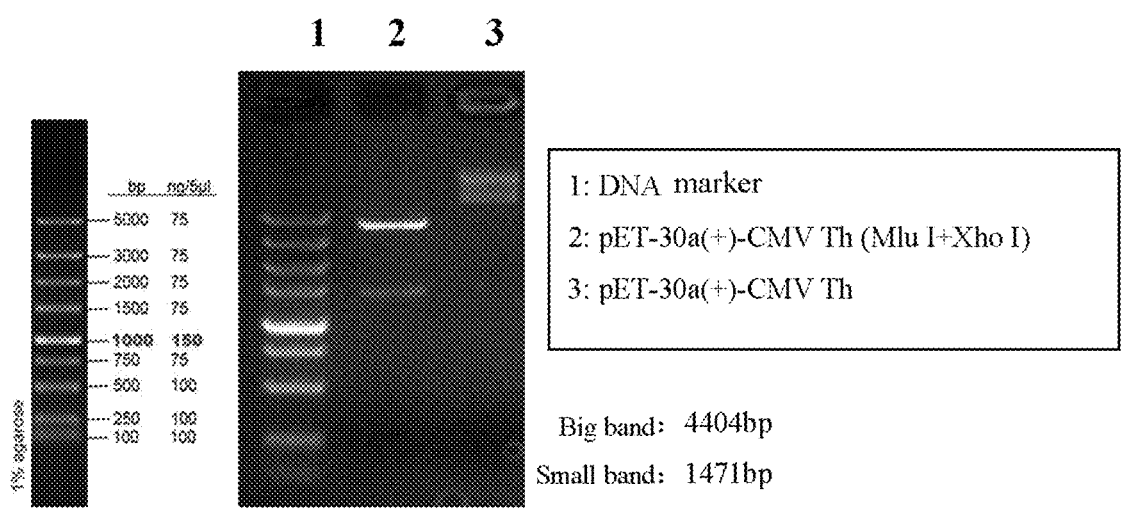

Example 6 Construction of Prokaryotic Expression Vector Containing Fusion Protein of LMN-CTB and CMV Th Epitopes Ten (10) CMV-derived Th epitopes pp65-11, pp65-71, pp65-92, pp65-123, pp65-128, pp65-57, pp65-62, pp65-30, pp65-112 and pp65-104 were selected from Table 4, and linked together in tandem to form the amino acid sequence shown in SEQ ID NO: 44, wherein the sequence segment "EFELRRQ" in SEQ ID NO: 44 is formed due to the introduction of enzyme restriction site, which belongs to a common technique for fusion and construction. By means of an online codon optimization software, the nucleotide sequence for *E. coli* codon usage preference (SEQ ID NO: 45) was obtained through optimization based on the amino acid sequence of Th epitopes. The nucleotide sequence was synthesized by Shanghai Generay Biotech Co., Ltd., and then inserted between the multiple cloning sites Nco I and Xho I on the prokaryotic expression vector pET-30a (+) (Novagen, Cat. No. 69909) by a molecular biology method well known in the art to construct the prokaryotic expression construct pET-30a (+)-CMV Th (the plasmid map is shown in FIG. 13) capable of expressing the fusion protein as an antigen, which was stored after being sequenced for identification. The vector pET-30a (+)-CMV Th was identified by the restriction endonucleases Mlu I and Xho I (the enzyme digestion system is shown in Table 11), and its enzyme digestion map for verification is shown in FIG. 14.

As shown in FIG. 13, CMV Th1 contains 5 CMV Th epitopes consisting of pp65-11, pp65-71, pp65-92, pp65-123 and pp65-128 in tandem, and CMV Th2 contains 5 CMV Th epitopes consisting of pp65-57, pp65-62, pp65-30, pp65-112 and pp65-104. Three restriction enzyme sites such as EcoR I, Sac I and Sal I were introduced between CMV Th1 and CMV Th2.

TABLE 11

Enzyme digestion system for identification of plasmid pET-30a(+)-CMV Th (enzyme digestion at 37° C., overnight)

| Enzyme digestion system | Volume |
| --- | --- |
| Plasmid pET-30a(+)-CMV Th | 3 μL, about 1 μg |
| Mlu I (Takara, Cat. No. 1071A) | 1 μL |
| Xho I (Takara, Cat. No. 1094A) | 1 μL |
| Enzyme digestion buffer | 1 μL |
| ddH$_2$O | q.s. to 10 μL |

Figure 15:
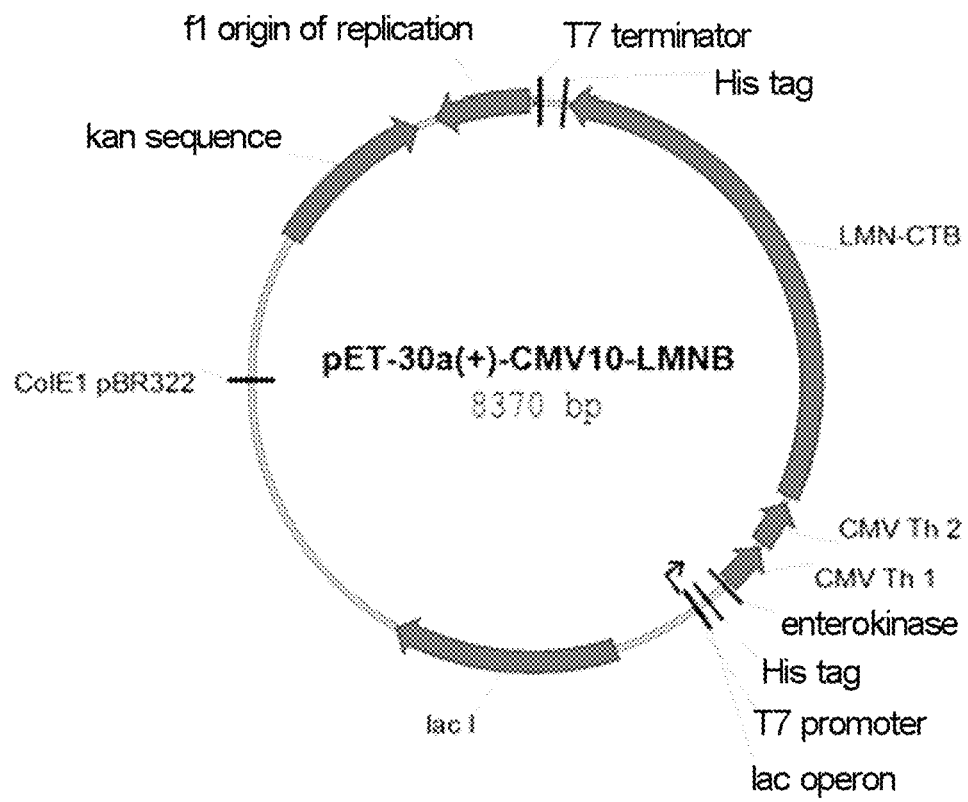
FIGS. 15 and 16 are a plasmid map and a map of double enzyme digestion for identification of the prokaryotic vector pET-30a(+)-CMV10-LMNB carrying the encoding sequences of a CMV-derived epitope, LAGE-1, MAGE-A3 and NY-ESO-1 antigens, and cholera toxin subunit B, respectively.
Figure 16:
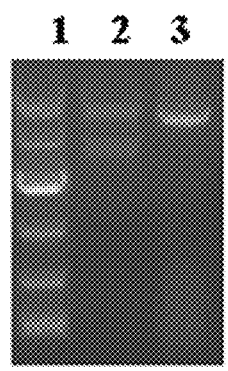

The primers were designed (Table 12), and a nucleic acid fragment containing the LMN-CTB encoding sequence was amplified by a PCR method using pET-30a(+)-LMN-CTB in Example 5 as a template, and the instructions of Ex Taq Enzyme Reagent (Takara, Cat. No. RR001B) were referred to for the specific method. The nucleic acid fragment was then inserted between Not I and Xho I on the pET-30a(+)-CMV Th vector in Example 6 by a molecular biology method well known in the art to construct the pET-30a(+)-CMV10-LMNB vector (the plasmid map is shown in FIG. 15), which was stored after being sequenced for identification. The vector pET-30a(+)-CMV10-LMNB was identified by the restriction endonucleases BamH I and Xho I (the enzyme digestion system is shown in Table 13) and its enzyme digestion map for verification is shown in FIG. 16. As shown in FIG. 15, pET-30a(+)-CMV10-LMNB contains CMV Th1 and CMV Th2 fragments, i.e. all 10 CMV Th epitopes in Table 4. These epitopes are pp65-11, pp65-71, pp65-92, pp65-123, pp65-128, pp65-57, pp65-62, pp65-30, pp65-112, and pp65-104.

TABLE 12

Primer design in Example 6

| Primer | Sequence |
| --- | --- |
| 6F (SEQ ID NO: 46) | GCGCGGCCGCGACGACAAGGCCATGGCT |
| 6R (SEQ ID NO: 47) | GCCTCGAGGTTAGCCATAGAGATAGC |

TABLE 13

Enzyme digestion system for identification of pET-30a(+)-CMV10-LMNB (enzyme digestion at 37° C., overnight)

| Enzyme digestion system | Volume |
| --- | --- |
| Plasmid pET-30a(+)-CMV10-LMNB | 3 μL, about 1 μg |
| BamH I (Takara, Cat. No. 1010A) | 1 μL |
| Xho I (Takara, Cat. No. 1094A) | 1 μL |
| Enzyme digestion buffer | 1 μL |
| ddH$_2$O | q.s. to 10 μL |

Example 7 Construction of Prokaryotic Expression Vector Containing Fusion Protein of LMN-CTB and Influ Th Epitopes Thirteen (13) Th epitopes derived from Flu virus, HA203, NP438, NS1-84, M1-181, HA375, NP24, NP95, NP221, HA434, HA440, NP324, M1-127 and M1-210 were selected from Table 4, and linked together in tandem to form the amino acid sequence shown in SEQ ID NO: 48.

Figure 17:
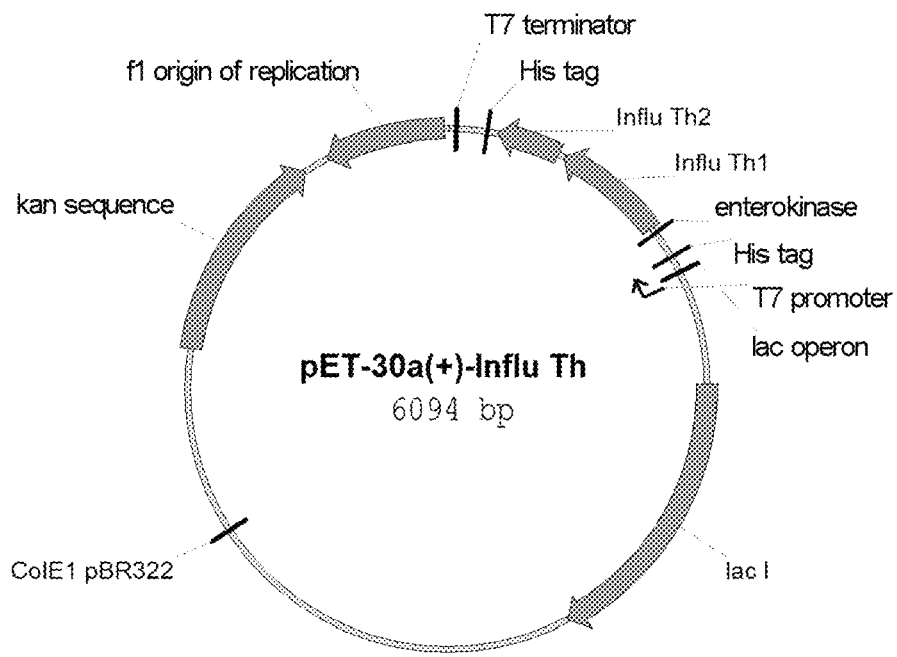
FIGS. 17 and 18 are a plasmid map and a map of double enzyme digestion for identification of the prokaryotic vector pET-30a(+)-CMV Th carrying the encoding sequences of a Flu virus-derived epitope, respectively.
Figure 18:
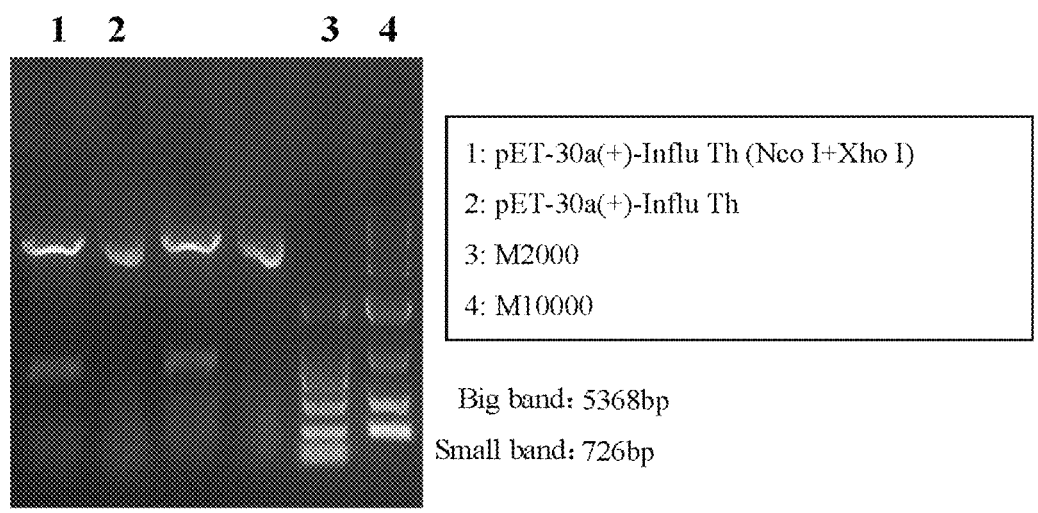

By means of an online codon optimization software, the nucleotide sequence for *E. coli* codon usage preference (SEQ ID NO: 49) was obtained through optimization based on the amino acid sequence containing Flu virus Th epitopes. The nucleotide sequence was synthesized by Shanghai Generay Biotech Co., Ltd., and then inserted between the multiple cloning sites Nco I and Xho I on the prokaryotic expression vector pET-30a (+) (Novagen, Cat. No. 69909) by a molecular biology method well known in the art to construct the prokaryotic expression construct pET-30a (+)-Influ Th (the plasmid map is shown in FIG. 17) capable of expressing the fusion protein as an antigen, which was stored after being sequenced for identification. The vector pET-30a (+)-Influ Th was identified by the restriction endonucleases Nco I and Xho I (the enzyme digestion system is shown in Table 14), and its enzyme digestion map for verification is shown in FIG. 18.

As shown in FIG. 17, Influ Th1 contains 8 Flu virus Th epitopes consisting of HA203, NP438, NS1-84, M1-181, HA375, NP24, NP95 and NP221 in tandem, and Influ Th2 contains 5 Flu virus Th epitopes consisting of HA434, HA440, NP324, M1-127 and M1-210. Three restriction sites such as EcoR I, Sac I and Sal I were introduced between Influ Th1 and Influ Th2.

TABLE 14

Enzyme digestion system for identification in Example 7 (enzyme digestion at 37° C., overnight)

| Enzyme digestion system | Volume |
| --- | --- |
| Plasmid pET-30a(+)-Influ Th | 3 μL, about 1 μg |
| Nco I (Takara, Cat. No. 1160A) | 1 μL |
| Xho I (Takara, Cat. No. 1094A) | 1 μL |
| Enzyme digestion buffer | 1 μL |
| ddH$_2$O | q.s. to 10 μL |

Figure 19:
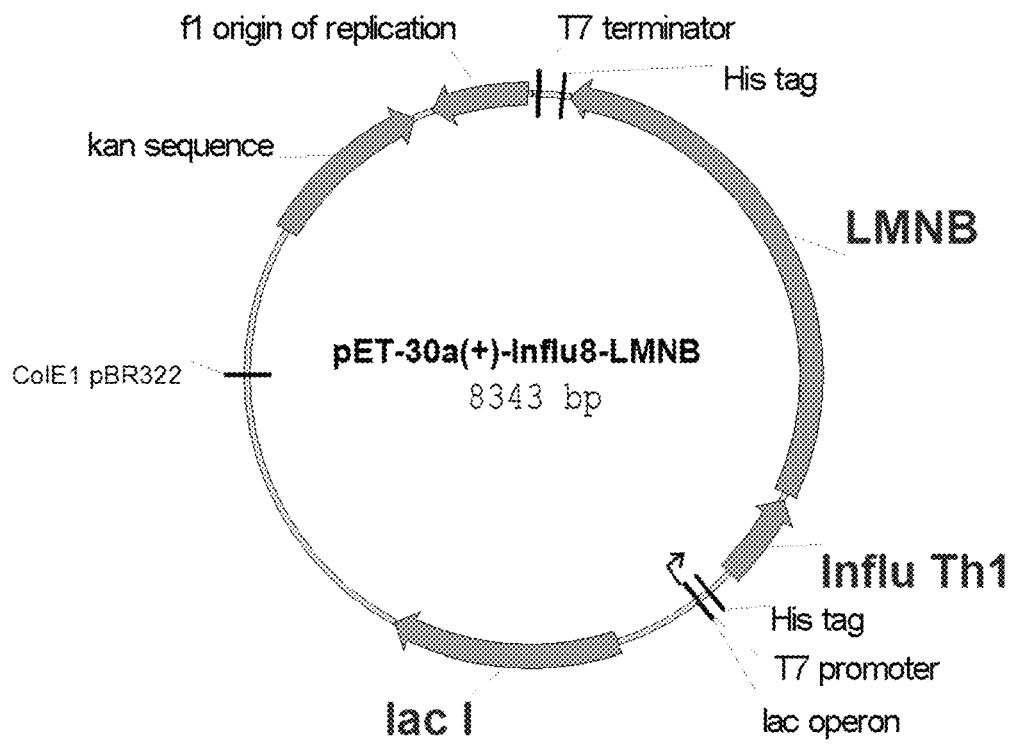
FIGS. 19 and 20 are a plasmid map and a map of double enzyme digestion for identification of the prokaryotic vector pET-30a(+)-Influ8-LMNB carrying the encoding sequences of a Flu virus-derived epitope, LAGE-1, MAGE-A3 and NY-ESO-1 antigens, and cholera toxin subunit B, respectively.
Figure 20:

The primers were designed (Table 15), and a nucleic acid fragment containing the LMN-CTB encoding sequence was amplified by a PCR method using pET-30a(+)-LMN-CTB in Example 5 as a template, and the instructions of Ex Taq Enzyme Reagent (Takara, Cat. No. RR001B) were referred to for the specific method. The nucleic acid fragment was then inserted between Not I and Sal I on the pET-30a(+)-Influ Th vector in Example 7 by a molecular biology method well known in the art to construct the pET-30a(+)-Influ8-LMNB vector (containing 8 Flu virus Th epitopes; the plasmid map is shown in FIG. 19), which was stored after being sequenced for identification. The vector pET-30a(+)-Influ8-LMNB was identified by the restriction endonucleases BamH I and Xho I (the enzyme digestion system is shown in Table 16) and its enzyme digestion map for verification is shown in FIG. 20.

As shown in FIG. 19, the pET-30a(+)-Influ8-LMNB vector contains the Influ Th1 segment, i.e., 8 Flu virus Th epitopes including HA203, NP438, NS1-84, M1-181, HA375, NP24, NP95, and NP221 in Table 4.

TABLE 15

Primers in Example 7

| Primer | Sequence |
| --- | --- |
| 7F1 (SEQ ID NO: 50) | GCGCGGCCGCGTTAGCCATAGAGATAGC |
| 7R1 (SEQ ID NO: 51) | GCGTCGACAAGACGACAAGGCCATGGCTATGC |

TABLE 16

Enzyme digestion system for identification of plasmid pET-30a(+)-Influ8-LMNB (enzyme digestion at 37° C., overnight)

| Enzyme digestion system | Volume |
|---|---|
| Plasmid pET-30a(+)-Influ8-LMNB | 3 µL, about 1 µg |
| BamH I (Takara, Cat. No. 1010A) | 1 µL |
| Xho I (Takara, Cat. No. 1094A) | 1 µL |
| Enzyme digestion buffer | 1 µL |
| ddH₂O | q.s. to 10 µL |

Figure 21:
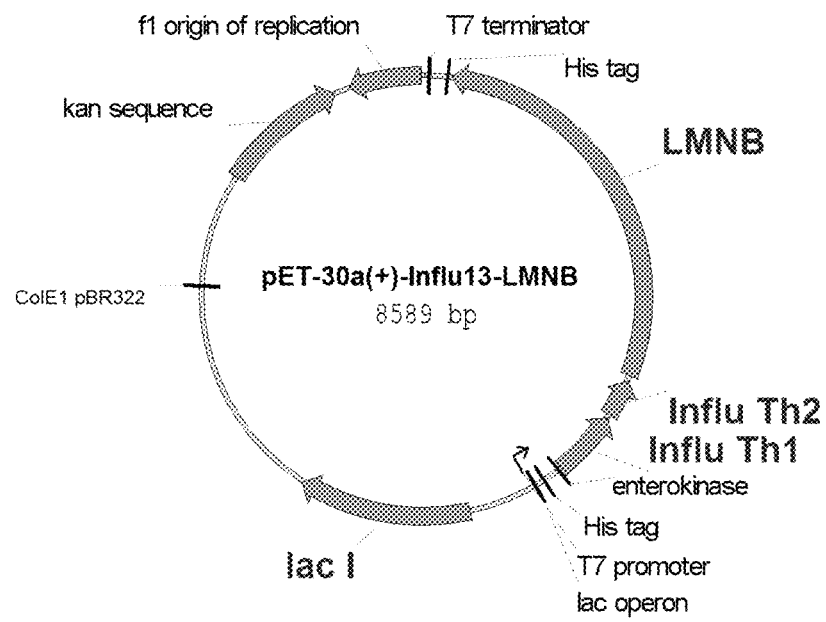
FIGS. 21 and 22 are a plasmid map and a map of double enzyme digestion for identification of the prokaryotic vector pET-30a(+)-Influ13-LMNB carrying the encoding sequences of a Flu virus-derived epitope, LAGE-1, MAGE-A3 and NY-ESO-1 antigens, and cholera toxin subunit B, respectively.
Figure 22:
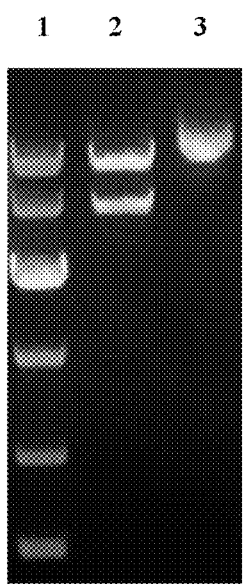

The primers were designed (Table 17), and a nucleic acid fragment containing the LMN-CTB encoding sequence was amplified by a PCR method using pET-30a(+)-LMN-CTB in Example 5 as a template, and the instructions of Ex Taq Enzyme Reagent (Takara, Cat. No. RR001B) was referred to for the specific method. This nucleic acid fragment was then inserted between Not I and Xho I on the pET-30a(+)-Influ Th vector in Example 6 by a molecular biology method well known in the art to construct the pET-30a(+)-Influ13-LMNB vector (containing 13 Flu virus Th epitopes; the plasmid map is shown in FIG. 21), which was stored after being sequenced for identification. The vector pET-30a(+)-CMV10-LMNB was identified by the restriction endonucleases BamH I and Xho I (the enzyme digestion system is shown in Table 18) and its enzyme digestion map for verification is shown in FIG. 22.

As shown in FIG. 21, the pET-30a(+)-Influ13-LMNB vector contains both the Influ Th1 and Influ Th2 segments, i.e., 8 Flu virus Th epitopes including HA203, NP438, NS1-84, M1-181, HA375, NP24, NP95, and NP221 in Table 4, and 5 Flu virus Th epitopes including HA434, HA440, NP324, M1-127 and M1-210 in Table 4. The vector includes all 13 Flu virus Th epitopes in total in Table 4.

TABLE 17

Primer design in Example 7

| Primer | Sequence |
|---|---|
| 7F2 (SEQ ID NO: 52) | GCCTCGAGGTTAGCCATAGAGATAGCA |
| 7R2 (SEQ ID NO: 53) | GCGCGGCCGCGACGACAAGGCCATGGTATG |

TABLE 18

Enzyme digestion system for identification in Example 7 (enzyme digestion at 37° C., overnight)

| Enzyme digestion system | Volume |
|---|---|
| Plasmid pET-30a(+)-Influ13-LMNB | 3 µL, about 1 µg |
| BamH I (Takara, Cat. No. 1010A) | 1 µL |
| Xho I (Takara, Cat. No. 1094A) | 1 µL |
| Enzyme digestion buffer | 1 µL |
| ddH₂O | q.s. to 10 µL |

Example 8 Expression and Purification of Fusion Protein

The prokaryotic expression vector pET-30a(+)-LMN constructed in Example 4, the prokaryotic expression vector pET-30a(+)-LMN-CTB constructed in Example 5, the prokaryotic expression vectors pET-30a(+)-CMV5-LMNB and pET-30a(+)-CMV10-LMNB constructed in Example 6, the prokaryotic expression vectors pET-30a(+)-Influ8-LMNB and pET-30a(+)-Influ13-LMNB constructed in Example 7 were respectively transformed into BL21 (DE3) competent cells (Tiangen Biotech (Beijing) Co., Ltd., Cat. No. CB105; the instructions of competent cells were referred to for the transformation method) to prepare the recombinant proteins LMN (its amino acid sequence is shown in SEQ ID NO: 59), LMNB (its amino acid sequence is shown in SEQ ID NO: 54), LMNB-C10 (its amino acid sequence is shown in SEQ ID NO: 58), LMNB-18 (its amino acid sequence is shown in SEQ ID NO: 55), and LMNB-I13 (its amino acid sequence is shown in SEQ ID NO: 56) according to the pET System Manual (TB055 8th Edition February 2099, Novagen), respectively, which were stored at −80° C. after subpackage.

The concentrations of the recombinant proteins prepared are 1 mg/mL, as detected by a BCA method (Beyotime Institute of Biotechnology, Cat. No. P0009), and the instructions of detection kit were referred to for the detection method. The contents of endotoxin in the prepared recombinant proteins were less than 1 EU/mg, as measured by a gel method (Chinese Horseshoe Crab Reagent Manufactory Co., Ltd., Xiamen, Cat. No. G011000), which meet the requirements of an animal experiment, and the instructions of horseshoe crab agent were referred to for the detection method.

Example 9 Animal Immunization Experiment

The information of the vaccines prepared in Examples 2, 3 and 8 is shown in Table 19. The DNA vaccine vector pVKD1.0 was provided by Vacdiagn Biotechnology Co., Ltd., Suzhou Industrial Park, and the Flu antigen NP (NCBI reference sequence: YP_009118476.1) of the DNA vaccine pVKD1.0-NP (the expression is derived from the virus strain A/Shanghai/02/2013 (H7N9)) was provided by Vacdiagn Biotechnology Co., Ltd., Suzhou Industrial Park, and the protein vaccine VP1 (VP1 protein of enterovirus 71, see the Chinese Patent Application No. 201310088364.5) was provided by Vacdiagn Biotechnology Co., Ltd., Suzhou Industrial Park.

Sixteen (16) 6-8 weeks old female BAL B/c mice were purchased from the Laboratory Animal Center of Suzhou University and raised in the SPF animal house of the Laboratory Animal Center of Suzhou University. The experimental animal grouping and vaccination schemes are shown in Table 20. All DNA vaccines were injected into the tibialis anterior muscle of the calf at 100 jug/animal. All protein vaccines were fully emulsified with complete Freund's adjuvant (CFA) or incomplete Freund's adjuvant (IFA), and injected subcutaneously into the back at 10 µg/animal. Two weeks after the last immunization, the mice were sacrificed, and their serums and splenocytes were collected for an enzyme-linked immunospot (ELISPOT) assay and an enzyme-linked immunosorbent assay (ELISA), respectively.

The mouse IFN-γ ELISPOT kit was purchased from BD, USA (Cat. No. 551083), and the instructions of IFN-γ ELISPOT kit from BD were referred to for the method. The stimulating peptide was NY-ESO-1 41 #peptide (WITQCFLPVFLAQPP) synthesized by Shanghai Science Peptide Biological Technology Co., Ltd., with a final stimulating concentration of 10 μg/mL. The positive stimuli phorbol-12-myristate-13-acetate (PMA) and ionomycin were purchased from Sigma, USA.

An ELISA method is well known for a person skilled in the art, and briefly described below. The 96-well ELISA plates were purchased from Jianghai Glass Instrument General Factory. Both the recombinant LMN and NY-ESO-1 were provided by Vacdiagn Biotechnology Co., Ltd., Suzhou Industrial Park. The plates were coated with the proteins in NaHCO$_3$ buffer (pH 9.6) at 4° C. overnight at a coating concentration of 10 μg/mL, followed by blocking with 0.1% bovine serum albumin (BSA) in phosphate buffered saline (PBS) at 37° C. for 30 minutes and then washing 5 times with 0.5% Tween 20 in phosphate buffered saline (PBST). An incubation with the mouse serum at room temperature was carried out for 1 hour at an initial dilution of 1:100 and washed 5 times with PBST, and another incubation with goat anti-mouse HRP secondary antibody (Santacruz, USA) was carried out at 1: 5000 at 37° C. for 30 min. After being washing 5 times with PBST, the substrate was developed with 3,3,5,5-tetramethylbenzidine (TMB) at 37° C. for 15 min, the development was stopped with 2M dilute sulfuric acid, and then the absorbance (A) values were read at 450 nm using a microplate reader (Thermo, USA). A value which is 2.1 times greater than the negative control A value was judged to be positive, and the reciprocal of the highest dilution with respect to the positive values was defined as the serum antibody titer. A titer was defined as 50 when it was less than the initial dilution of 1: 100.

TABLE 19

| Vaccine information | | | |
|---|---|---|---|
| Vaccine | Attribute | Antigen | CD4 Th epitope |
| pVKD1.0-LMN-CTB | DNA | LAGE-1, MAGE-A3, NY-ESO-1, | Epitope-free |
| pVKD1.0-CI-LMNB | DNA | LAGE-1, MAGE-A3, NY-ESO-1 | 5 CMV epitopes, 8 influenza virus epitopes |
| pVKD1.0-CI | DNA | None | 5 CMV epitopes, 8 influenza virus epitopes |
| pVKD1.0-NP | DNA | NP | 5 influenza virus epitopes |
| LMNB | Recombinant protein | LACE-1, MAGE-A3, NY-ESO-1 | Epitope-free |
| LMNB-I8 | Recombinant protein | LAGE-1, MAGE-A3, NY-ESO-1 | First 8 influenza virus epitopes |
| LMNB-I13 | Recombinant protein | LAGE-1, MAGE-A3, NY-ESO-1 | 13 influenza virus epitopes |
| LMNB-C5 | Recombinant protein | LAGE-1, MAGE-A3, NY-ESO-1 | First 5 CMV epitopes |
| LMNB-C10 | Recombinant protein | LAGE-1, MAGE-A3, NY-ESO-1 | 10 CMV epitopes |
| VP1 | Recombinant protein | VP1 | Epitope-free |

TABLE 20

| | Week 0, 4, 8 | | Week 12, 16, 20 | | Week 24 | | Week 28 | |
|---|---|---|---|---|---|---|---|---|
| Grouping | Vaccine | Dose | Vaccine | Dose | Vaccine | Dose | Vaccine | Dose |
| A(n = 4) | pVKD1.0-NP | 100 μg | pVKD1.0 | 100 μg | VP1/CFA | 100 μg | VPI/IFA | 100 μg |
| B(n = 4) | pVKD1.0-NP | 100 μg | pVKD1.0-LMNB | 100 μg | LMNB/CFA | 100 μg | LMNB/IFA | 100 μg |
| C(n = 4) | pVKD1.0-NP | 100 μg | pVKD1.0-CI-LMNB | 100 μg | LMNB-I8/CFA | 100 μg | LMNB-I8/IFA | 100 μg |
| D(n = 4) | pVKD1.0-NP | 100 μg | pVKD1.0-CI-LMNB | 100 μg | LMNB-I13/CFA | 100 μg | LMNB-I13/IFA | 100 μg |

Figure 23:
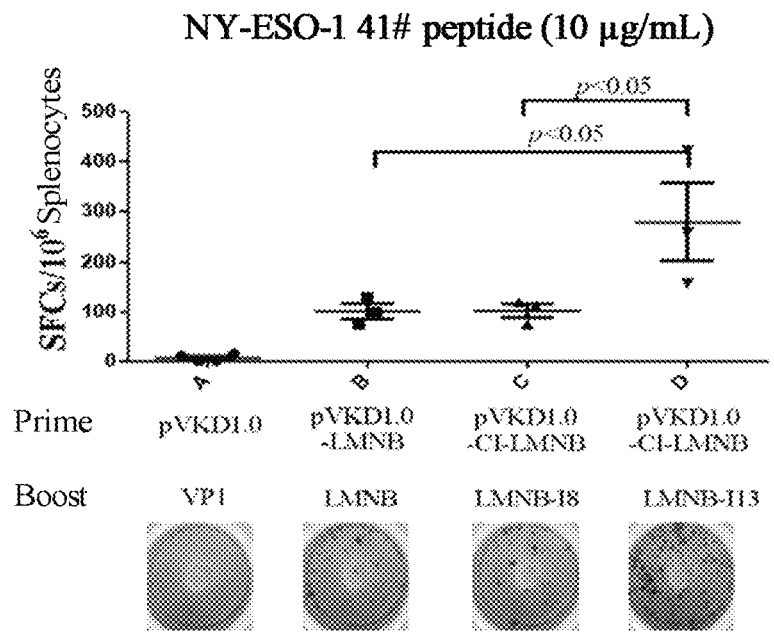
FIG. 23 shows the detection results of cellular immune responses in the animal immunization experiment.

The results of cellular immune response assay are shown in FIG. 23. Among them, the group primed with pVKD1.0-CI-LMNB DNA vaccine and boosted with LMNB-I13 protein (i.e., group D in Example 8) had the best immune effect, which was significantly higher than those of the parallel control group (group B) and the group boosted with LMNB-I8 (group C). Moreover, the level of cellular immune response in the group boosted with LMNB-I13 protein was nearly 3-fold higher than that in the parallel control group (group B). The results show that a load of 13 Flu virus Th epitopes (group D) can significantly increase the cellular immune response level of weak immunogens.

Figure 24:
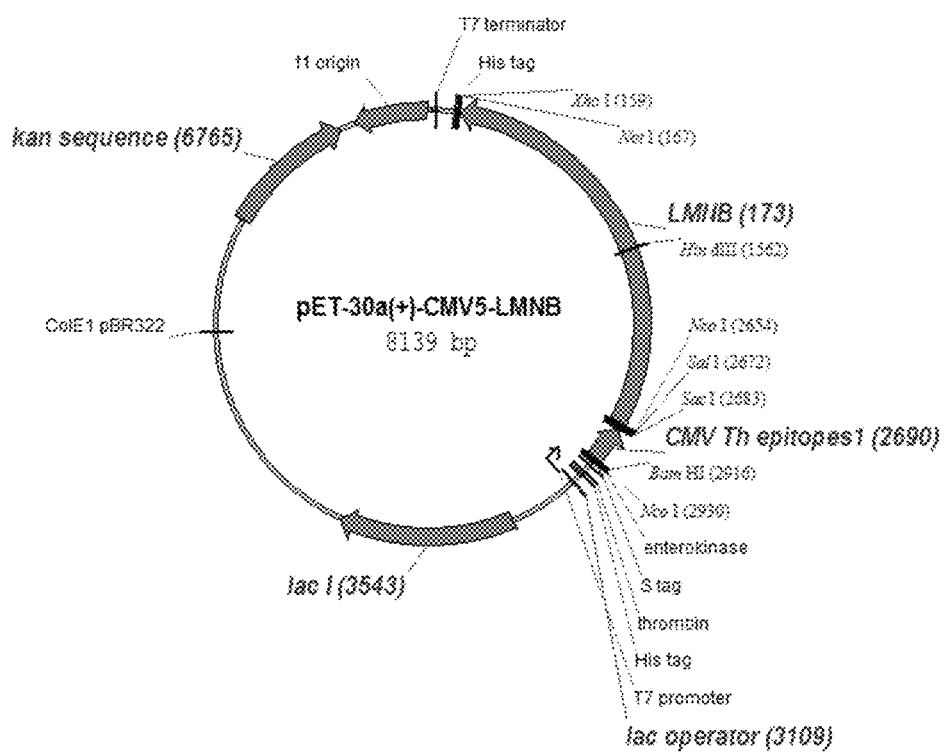
FIGS. 24 and 25 are a plasmid map and a map of double enzyme digestion for identification of the prokaryotic vector pET-30a(+)-CMV5-LMNB carrying the encoding sequences of a CMV-derived epitope, LAGE-1, MAGE-A3 and NY-ESO-1 antigens, and cholera toxin subunit B, respectively.
Figure 25:
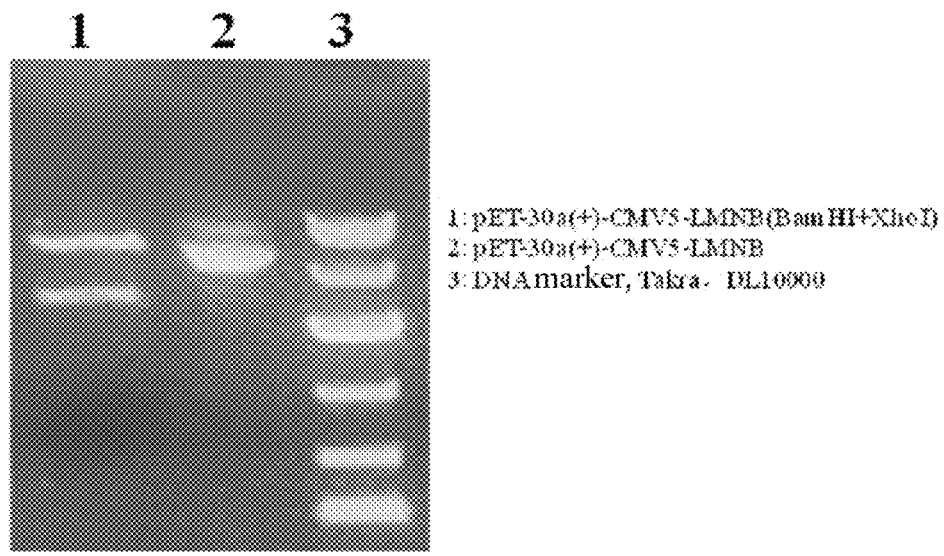

Example 10 Construction of Prokaryotic Expression Vector Containing Fusion Protein of LMN-CTB and CMV Th Epitope The primers were designed (Table 21), and a nucleic acid fragment containing the LMN-CTB encoding sequence was amplified by a PCR method using pET-30a(+)-LMN-CTB in Example 5 as a template, and the instructions of Ex Taq Enzyme Reagent (Takara, Cat. No. RR001B) were referred to for the specific method. The nucleic acid fragment was then inserted between Not I and Sal I on the pET-30a(+)-CMV Th vector in Example 6 by a molecular biology method well known in the art to construct the pET-30a(+)-CMV5-LMNB vector (the plasmid map is shown in FIG. 24), which was stored after being sequenced for identification. The vector pET-30a(+)-CMV5-LMNB was identified by the restriction endonucleases BamH I and Xho I (the enzyme digestion system is shown in Table 22) and its enzyme digestion map for verification is shown in FIG. 25. As shown in FIG. 24, pET-30a(+)-CMV5-LMNB contains a CMV Th1 fragment, i.e. the first 5 CMV Th epitopes in Table 4. These epitopes are pp65-11, pp65-71, pp65-92, pp65-123 and pp65-128.

TABLE 21

Primer design in Example 10

| Primer | Sequence |
|---|---|
| 7F1 (SEQ ID NO: 50) | GCGCGGCCGCGTTAGCCATAGAGATAGC |
| 7R1 (SEQ ID NO: 51) | GCGTCGACAAGACGACAAGGCCATGGCTATGC |

TABLE 22

Enzyme digestion system for identification of pET-30a(+)-CMV10-LMNB (enzyme digestion at 37° C., overnight)

| Enzyme digestion system | Volume |
|---|---|
| Plasmid pET-30a(+)-CMV10-LMNB | 3 µL, about 1 µg |
| BamH I (Takara, Cat. No. 1010A) | 1 µL |
| Xho I (Takara, Cat. No. 1094A) | 1 µL |
| Enzyme digestion buffer | 1 µL |
| ddH$_2$O | q.s. to 10 µL |

Example 11 Expression and Purification of Fusion Protein

As described in Example 8, the prokaryotic expression vector pET-30a(+)-CMV5-LMNB constructed in Example 10 was transformed into BL21 (DE3) competent cells (Tiangen Biotech (Beijing) Co., Ltd., Cat. No. CB105; the instructions of competent cells were referred to for the transformation method) to prepare the recombinant protein LMNB-05 (its amino acid sequence is shown in SEQ ID NO: 57) according to the pET System Manual (TB055 8th Edition February 2099, Novagen), which was stored at −80° C. after subpackage.

The concentration of the recombinant protein prepared was 1 mg/mL, as detected by a BCA method (Beyotime Institute of Biotechnology, Cat. No. P0009), and the instructions of detection kit were referred to for the detection method. The content of endotoxin in the prepared recombinant protein was less than 1 EU/mg, as measured by a gel method (Chinese Horseshoe Crab Reagent Manufactory Co., Ltd., Xiamen, Cat. No. G011000), which met the requirements of an animal experiment, and the instructions of Horseshoe Crab agent were referred to for the detection method.

Example 12 Animal Immunization Experiment

The vaccine information is shown in Table 19. The DNA vaccine pVKD1.0-CI (Example 3) was provided by Vacdiagn Biotechnology Co., Ltd., Suzhou Industrial Park.

Twenty (20) 6-8 weeks old female BAL B/c mice were purchased from the Laboratory Animal Center of Suzhou University and raised in the SPF animal house of the Laboratory Animal Center of Suzhou University. The experimental animal grouping and vaccination schemes are shown in Table 23. All DNA vaccines were injected into the tibial anterior muscle of the calf at 100 µg/animal. All protein vaccines were fully emulsified with complete Freund's adjuvant (CFA) or incomplete Freund's adjuvant (IFA), and injected subcutaneously into the back at 10 µg/animal. Two weeks after the last immunization, the mice were sacrificed, and their serums and splenocytes were collected for an enzyme-linked immunospot (ELISPOT) assay and an enzyme-linked immunosorbent assay (ELISA), respectively.

The mouse IFN-γ ELISPOT kit was purchased from BD, USA (Cat. No. 551083), and the instructions of IFN-γ ELISPOT kit from BD were referred to for the method. The stimulating peptide was NY-ESO-1 41 #peptide (WITQCFLPVFLAQPP) synthesized by Shanghai Science Peptide Biological Technology Co., Ltd., with a final stimulating concentration of 10 µg/mL. The positive stimuli phorbol-12-myristate-13-acetate (PMA) and ionomycin were purchased from Sigma, USA.

An ELISA method is well known for a person skilled in the art and briefly described below. 96-well ELISA plates were purchased from Jianghai Glass Instrument General Factory. Both recombinant LMN and NY-ESO-1 were provided by Vacdiagn Biotechnology Co., Ltd., Suzhou Industrial Park. The plates were coated with the proteins in NaHCO$_3$ buffer (pH 9.6) at 4° C. overnight at a coating concentration of 10 µg/mL, followed by blocking with 0.1% bovine serum albumin (BSA) in phosphate buffered saline (PBS) at 37° C. for 30 minutes and then washing 5 times with 0.5% Tween 20 in phosphate buffered saline (PBST). An incubation with mouse serum was carried out at room temperature for 1 hour at an initial dilution of 1: 100 and washed 5 times with PBST. Another incubation with goat anti-mouse HRP secondary antibody (Santacruz, USA) was carried out at 1: 5000 at 37° C. for 30 min, and washed 5 times with PBST. The substrate was then developed with 3,3,5,5-tetramethylbenzidine (TMB) at 37° C. for 15 min and the development was stopped with 2M dilute sulfuric acid, and the absorbance (A) values were read at 450 nm using a microplate reader (Thermo, USA). A value which is 2.1 times greater than the negative control A value was judged to be positive, and the reciprocal of the highest dilution with respect to the positive values was defined as the serum antibody titer. A titer was defined as 50 when it was less than the initial dilution of 1: 100.

TABLE 23

Grouping and immunization schemes

| | Week 0, 4, 8 | | Week 12, 16, 20 | | Week 24 | | Week 28 | |
|---|---|---|---|---|---|---|---|---|
| Grouping | Vaccine | Dose | Vaccine | Dose | Vaccine | Dose | Vaccine | Dose |
| A(n = 5) | pVKD1.0-CI | 100 μg | pVKD1.0 | 100 μg | VP1/CFA | 10 μg | VP1/IFA | 10 μg |
| B(n = 5) | pVKD1.0-CI | 100 μg | pVKD1.0-LMNB | 100 μg | LMNB/CFA | 10 μg | LMNB/IFA | 10 μg |
| C(n = 5) | pVKD1.0-CI | 100 μg | pVKD1.0-CI-LMNB | 100 μg | LMNB-C5/CFA | 10 μg | LMNB-C5/CFA | 10 μg |
| D(n = 5) | PVKD1.0-CI | 100 μg | pVKD1.0-CI-LMNB | 100 μg | LMNB-C10/CFA | 10 μg | LMNB-C10/CFA | 10 μg |

Figure 26:
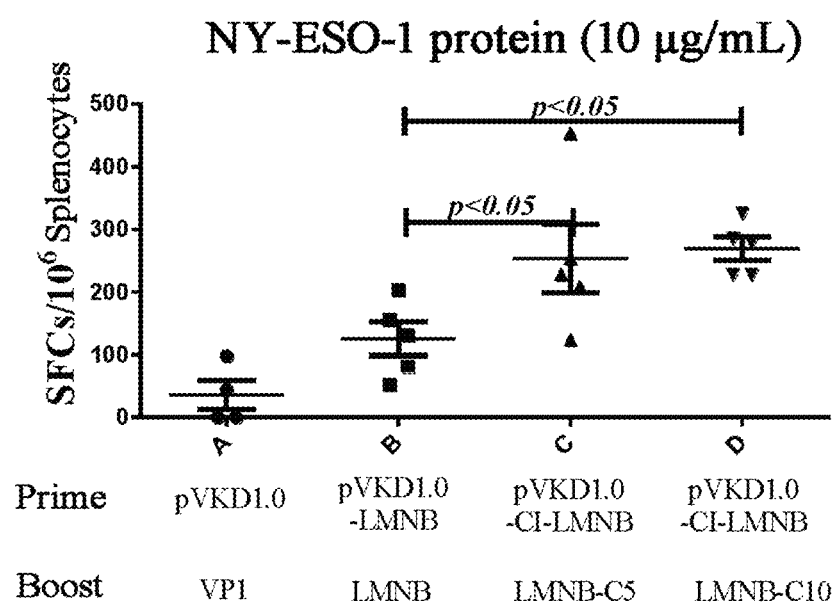
FIG. 26 shows the detection results of cellular immune responses in the animal immunization experiment in Example 12.

The results of cellular immune response assay are shown in FIG. 26. Among them, the group primed with the pVKD1.0-CI-LMNB DNA vaccine, boosted with the LMNB-05 protein (i.e. group C in Example 11) and boosted with the LMNB-C10 protein (i.e. group D in Example 11) had the best immune effect, which was significantly higher than that in the parallel control (group B). The results show that a load of 5 CMV virus Th epitopes (group C) and 10 CMV virus Th epitopes (group D) can significantly improve the cellular immune response of weak immunogens.

Example 13 Animal Experiment for Tumor Prevention

The information of vaccines prepared in Examples 2, 3 and 8 is shown in Table 19. The DNA vaccine vector pVKD1.0 was provided by Vacdiagn Biotechnology Co., Ltd., Suzhou Industrial Park, and the Flu antigen NP (NCBI reference sequence: YP_009118476.1) of the DNA vaccine pVKD1.0-NP (the expression is derived from the virus strain A/Shanghai/02/2013 (H7N9)) was provided by Vacdiagn Biotechnology Co., Ltd., Suzhou Industrial Park, and the protein vaccine VP1 (VP1 protein of enterovirus 71, see the Chinese Patent Application No. 201310088364.5) was provided by Vacdiagn Biotechnology Co., Ltd., Suzhou Industrial Park.

Sixty (60) 6-8 weeks old female BAL B/c mice were purchased from the Laboratory Animal Center of Suzhou University and raised in the SPF animal house of the Laboratory Animal Center of Suzhou University. The experimental animal grouping and vaccination schemes are shown in Table 24. All DNA vaccines were injected into the tibials anterior muscle of the calf at 100 μg/animal. All protein vaccines were fully emulsified with complete Freund's adjuvant (CFA) or incomplete Freund's adjuvant (IFA), and injected subcutaneously into the back at 10 μg/animal. Two weeks after the last immunization, the mice were inoculated subcutaneously with the cell line transfected stably by 4T1-hNY-ESO-1 (provided by Vacdiagn Biotechnology Co., Ltd., Suzhou Industrial Park), at an inoculation dose of $1\times10^5$ cells/mouse, and the tumor growth was continuously observed and measured after the inoculation. The tumor volume was calculated according to the following equation: tumor volume $(mm^3)$=length×width/2. The mice were sacrificed when the tumor volume exceeded 2000 $mm^3$.

TABLE 24

Grouping and immunization schemes

| | | Week 0, 4, 8 | | Week 12, 16, 20 | | Week 24 | | Week 28 | |
|---|---|---|---|---|---|---|---|---|---|
| Grouping | Vaccine | Dose | Vaccine | Dose | Vaccine | Dose | Vaccine | Dose | |
| A(n = 10) | pVKD1.0-NP | 50 μg | pVKD1.0 | 100 μg | VP1/CFA | 10 μg | VP1/IFA | 10 μg | |
| | pVKD1.0-CI | 50 μg | | | | | | | |
| B(n = 10) | pVKD1.0-NP | 50 μg | pVKD1.0-LMNB | 100 μg | LMNB/CFA | 10 μg | LMNB/IFA | 10 μg | |
| | pVKD1.0-CI | 50 μg | | | | | | | |
| C(n = 10) | pVKD1.0-NP | 50 μg | pVKD1.0-CI-LMNB | 100 μg | LMNB-I8/CFA | 10 μg | LMNB-I8/IFA | 10 μg | |
| | pVKD1.0-CI | 50 μg | | | | | | | |
| D(n = 10) | pVKD1.0-NP | 50 μg | pVKD1.0-CI-LMNB | 100 μg | LMNB-I13/CFA | 10 μg | LMNB-I13/IFA | 10 μg | |
| | pVKD1.0-CI | 50 μg | | | | | | | |
| E(n = 10) | pVKD1.0-NP | 50 μg | pVKD1.0-CI-LMNB | 100 μg | LMNB-I13/CFA | 10 μg | LMNB-C10/IFA | 10 μg | |
| | pVKD1.0-CI | 50 μg | | | | | | | |
| F(n = 10) | pVKD1.0-NP | 50 μg | pVKD1.0-CI-LMNB | 100 μg | LMNB-C10/CFA | 5 μg | LMNB-C10/IFA | 5 μg | |
| | pVKD1.0-CI | 50 μg | | | | LMNB-I13/CFA | 5 μg | LMNB-I13/IFA | 5 μg | |

Figure 27:
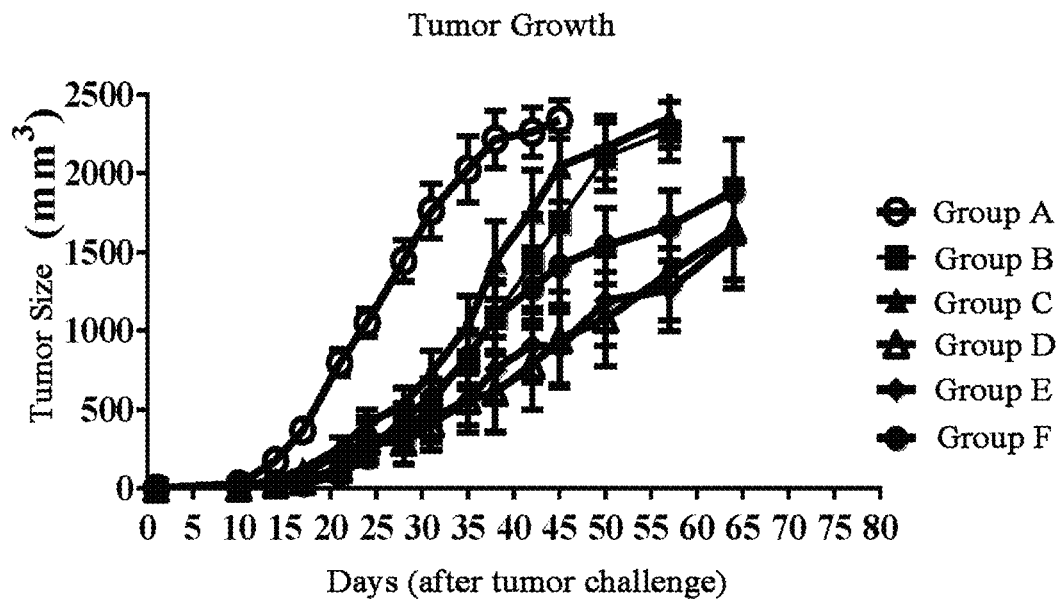
FIG. 27 shows the tumor growth of mice in Example 13.

The tumor growth of immunized mice in each group is shown in FIG. 27. Among them, all the mice in the control group (group A) developed tumors on the 14th day after the tumor challenge (i.e. after the tumor inoculation), and the tumors grew rapidly. The tumor growth of mice in each immunization group lagged behind that in the control group, wherein the mice in the group boosted with LMNB-I13 (group D) and the mice in the group boosted with a mixture of LMNB-I13 and LMNB-C10 (group E) had the slowest tumor growth, so these two groups of vaccines had the best effects.

Figure 28:
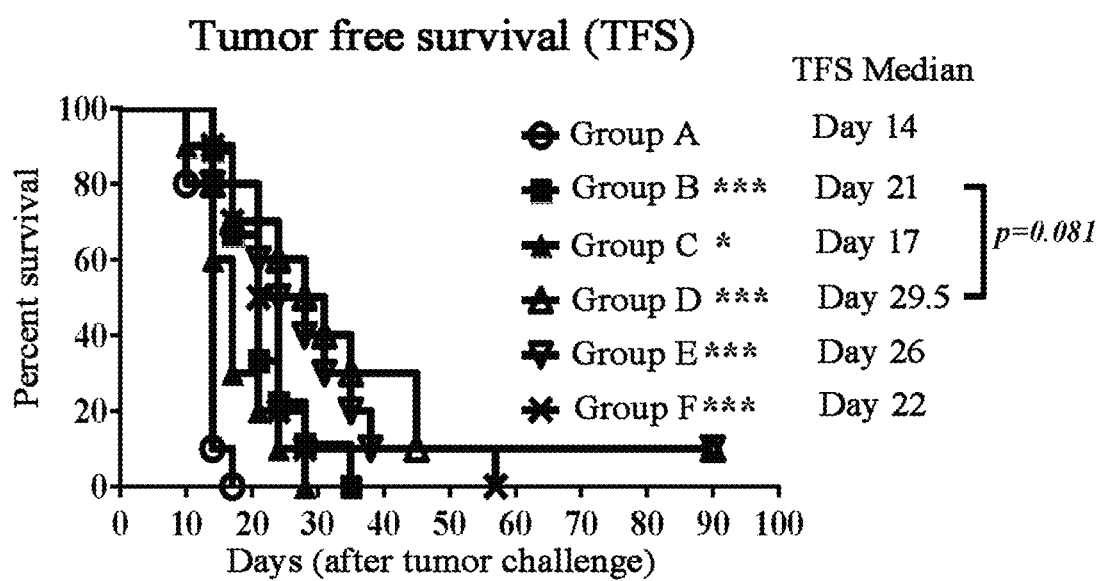
FIGS. 28 and 29 show the tumor-free survival and overall survival of mice in Example 13, respectively.

In addition, the analysis results of tumor-free survival for the mice are shown in FIG. 28. The median tumor-free survival (TFS) of mice in the control group A was 14 days. The tumor-free survival of mice in each vaccine immunized group was significantly higher than that in the control group, indicating that all vaccines could increase the tumor-free survival of immunized mice. Among them, group D with the 113 epitope fusion peptide, and group E and F with the 113 and C10 epitope fusion peptide had the best effects, and the tumor-free survival of mice was doubled at the most. In the vaccine group with the 113 epitope fusion peptide (group D), the tumor-free survival was significantly increased by about 40% compared to the conventional vaccine group (group B), showing that a load of 13 Th epitopes of Flu virus or 10 Th epitopes of CMV could significantly improve the protection effect of tumor vaccine against tumor.

Figure 29:
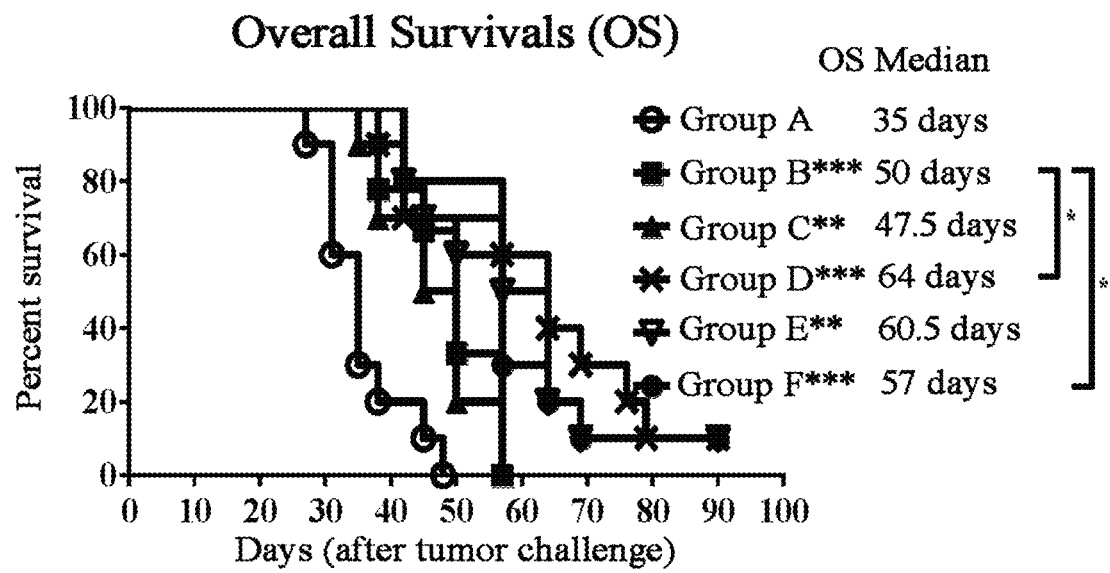

Finally, the analysis results of mouse overall survival are shown in FIG. 29. Among them, the median overall survival (OS) of mice in control group A was 35 days. The overall survival of mice in each vaccine immunized group was significantly higher than that in the control group, indicating that all vaccines could increase the survival of mice after immunization. Among them, group D with 113 epitope fusion peptide and groups E and F with 113 and C10 epitope fusion peptide had the best effects, and the overall survival rate was increased by 83%. Compared with the conventional vaccine group (group B), the vaccine group with the 113 epitope fusion peptide (groups D and group F) significantly increased the tumor-free survival by 28% at the most, indicating that a load of thirteen (13) Flu virus Th epitopes or ten (10) CMV Th epitopes could greatly improve the tumor protection effect of tumor vaccine.

Example 14 Tumor Treatment Experiment

The vaccines involved are shown in Example 9. Thirty (30) 6-8 weeks old female BAL B/c mice were purchased from the Laboratory Animal Center of Suzhou University and raised in the SPF animal house of the Laboratory Animal Center of Suzhou University. The experimental animal grouping and vaccination schemes are shown in Table 25. All DNA vaccines were injected into the tibialis anterior muscle of the calf at 100 µg/animal. All protein vaccines were fully emulsified with complete Freund's adjuvant (CFA) or incomplete Freund's adjuvant (IFA), and injected subcutaneously into the back at 10 µg/animal. Two weeks after the last immunization, the mice were inoculated subcutaneously with the cell line transfected stably by the tumor cells 4T1-hNY-ESO-1 (provided by Vacdiagn Biotechnology Co., Ltd., Suzhou Industrial Park), at a dose of $1 \times 10^5$ cells/mouse, and the corresponding mice were vaccinated subcutaneously with the protein vaccines on day 1, 8 and 15 after the tumor cell inoculation, respectively. The tumor growth was continuously observed and measured after the vaccination. The tumor volume was calculated according to the following equation: tumor volume $(mm^3)$=length×width/2. The mice were sacrificed when the tumor volume exceeded 2000 $mm^3$.

TABLE 25

| | Grouping and immunization schemes | | | | | |
|---|---|---|---|---|---|---|
| | Week 0, 4, 8 | | Week 10 | | Week 11, 12 | |
| Grouping | Vaccine | Dose | Vaccine | Dose | Vaccine | Dose |
| A(n = 10) | pVKD1.0-NP | 100 µg | pVKD1.0 | 100 µg | VP1/CFA | 10 µg |
| B(n = 10) | pVKD1.0-NP | 100 µg | LMNB/CFA | 10 µg | LMNB/IFA | 10 µg |
| C(n = 10) | pVKD1.0-NP | 100 µg | LMNB-I13/CFA | 10 µg | LMNB-I13/IFA | 10 µg |

Figure 30:
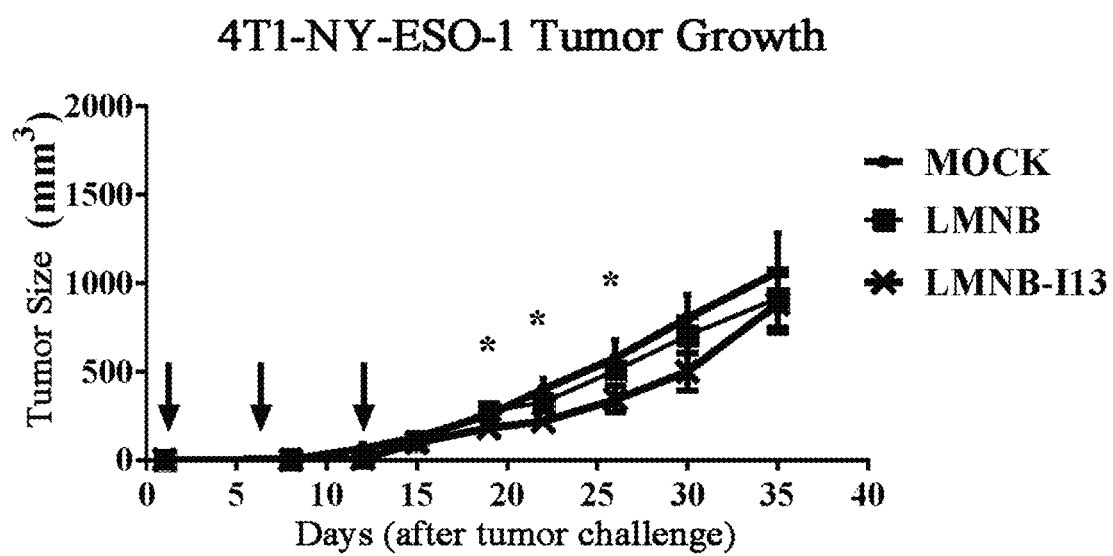
FIG. 30 shows the tumor growth of mice in each treatment group for the 4T1-hNY-ESO-1 mouse tumor model.

The tumor growth of immunized mice in each group is shown in FIG. 30. Among them, all the mice in the control group (group A) developed tumors on the 14th day after the tumor challenge (i.e. after the tumor inoculation), and the tumors grew rapidly. The mice in the group treated by the LMNB-I13 protein vaccine (group C) had the slowest tumor growth compared to the untreated control group (group A). Furthermore, the tumor size of mice in the group treated by the LMNB-I13 protein vaccine was significantly smaller than that in the control group (group A) on day 22 after the tumor challenge, and there was still a significant difference in tumor size between the two groups until day 30. By day 35, the tumor growth of mice began to accelerate in group C, which is possibly associated with the cease of vaccination with the LMNB-I13 protein vaccine. The results indicated that the LMNB-I13 protein vaccine could inhibit tumor growth in mice.

Example 15 Tumor Treatment Experiment

The vaccines involved are shown in Example 9. Thirty (30) 6-8 weeks old female BAL B/c mice were purchased from the Laboratory Animal Center of Suzhou University and raised in the SPF animal house of the Laboratory Animal Center of Suzhou University. The experimental animal grouping and vaccination schemes are shown in Table 26. All DNA vaccines were injected into the tibialis anterior muscle of the calf at 100 µg/animal. All protein vaccines were fully emulsified with complete Freund's adjuvant (CFA) or incomplete Freund's adjuvant (IFA), and injected subcutaneously into the back at 10 µg/animal. Two weeks after the last immunization, the mice were inoculated subcutaneously with the cell line transfected stably by the tumor cells CT26-hLAGE-1 (provided by Vacdiagn Biotechnology Co., Ltd., Suzhou Industrial Park), at an inoculation dose of $1 \times 10^5$ cells/mouse, and the corresponding mice were vaccinated subcutaneously with the protein vaccine on day 1, 8 and 15 after the tumor cell inoculation, respectively. The tumor growth was continuously observed and measured after the inoculation. The tumor volume was calculated according to the following equation: tumor volume $(mm^3)$= length×width/2. The mice were sacrificed when the tumor volume exceeded 2000 $mm^3$.

TABLE 26

Grouping and immunization schemes

| Grouping | Week 0, 4, 8 | | Week 10 | | Week 11, 12 | |
| --- | --- | --- | --- | --- | --- | --- |
| | Vaccine | Dose | Vaccine | Dose | Vaccine | Dose |
| A(n = 10) | pVKD1.0-NP | 100 μg | pVKD1.0 | 100 μg | VP1/CFA | 10 μg |
| B(n = 10) | pVKD1.0-NP | 100 μg | LMNB/CFA | 10 μg | LMNB/IFA | 10 μg |
| C(n = 10) | pVKD1.0-NP | 100 μg | LMNB-I13/CFA | 10 μg | LMNB-I13/IFA | 10 μg |

Figure 31:
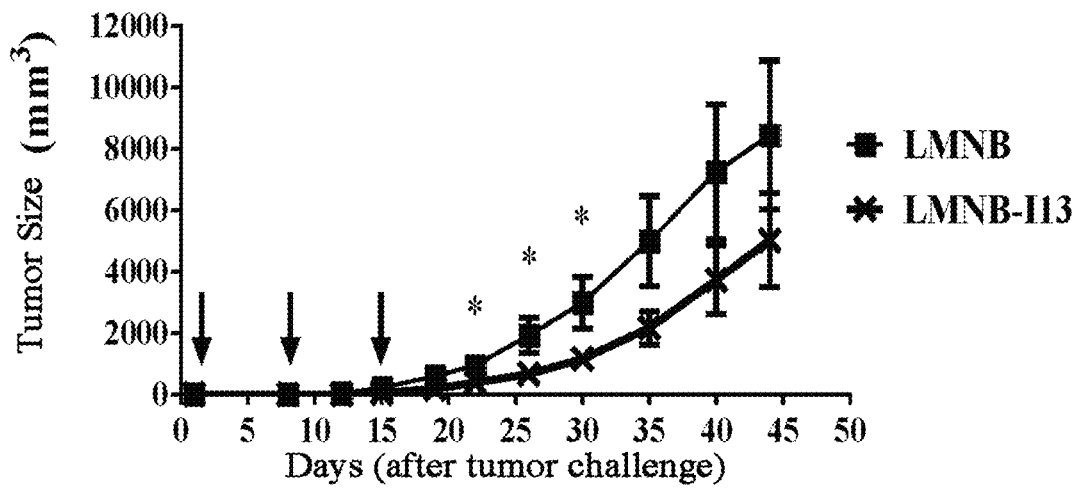
FIG. 31 shows the tumor growth of mice in each treatment group for the CT26-hLAGE-1 mouse tumor model.

The tumor growth of immunized mice in each group is shown in FIG. 31. Due to the failure of tumor inoculation of some mice in the untreated control group (group A) after the tumor challenge (i.e. after the tumor inoculation), such mice were not included for the analysis, and the parallel control vaccine group (group B) and the group treated by LMNB-I13 (group C) were compared. Compared with group B, the tumor growth of mice in group C was slower, and the tumor size of mice in the group treated by the LMNB-I13 protein vaccine was significantly smaller than that in parallel control vaccine group (group B) on day 22 after the tumor challenge. There was still a significant difference in tumor size between the two groups until day 30. Similarly, the increased tumor growth of mice in group C was also observed at a later stage in the CT26 mouse model, which is possibly associated with the cease of vaccination with the LMNB-I13 protein vaccine. These results indicated that the LMNB-I13 protein vaccine could inhibit tumor growth in mice.

Example 16 Construction of Shuttle Vector pSC65-LMNB-I13

The amino acid sequence of 113 (SEQ ID NO: 60) comprises 8 influenza virus Th epitopes including HA203, NP438, NS1-84, M1-181, HA375, NP24, NP95 and NP221 in Table 4, and 5 influenza virus Th epitopes including HA434, HA440, NP324, M1-127 and M1-210 in Table 4. The eukaryotic codon optimized sequence of the amino acid sequence encoding 113 (SEQ ID NO: 61) was synthesized by Suzhou Genewiz Biotechnology Co., Ltd., and then inserted into the shuttle vector pSC65 (addgene, Cat. No. 30327) by a molecular biology method well known in the art to construct the shuttle vector pSC65-I13 comprising 13 influenza epitopes.

Figure 32:
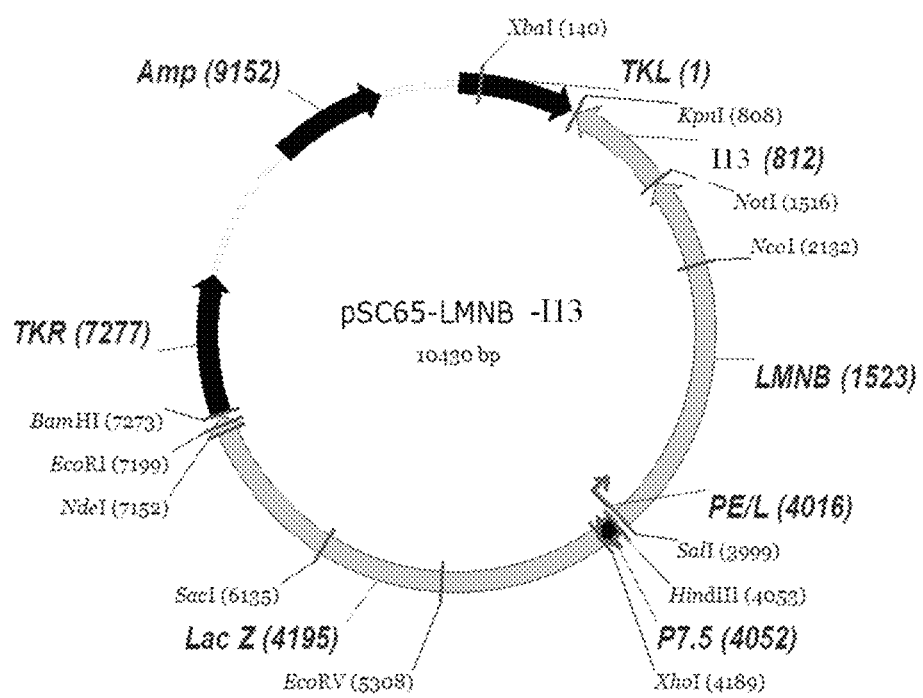
FIG. 32 and FIG. 33 are a plasmid map and a map of double enzyme digestion for identification of the shuttle vector pSC65-LMNB-I13 carrying the coding sequences of LAGE-1, MAGE-A3 and NY-ESO-1 antigens and the coding sequence of 13 influenza epitopes (I13), respectively.
Figure 33:
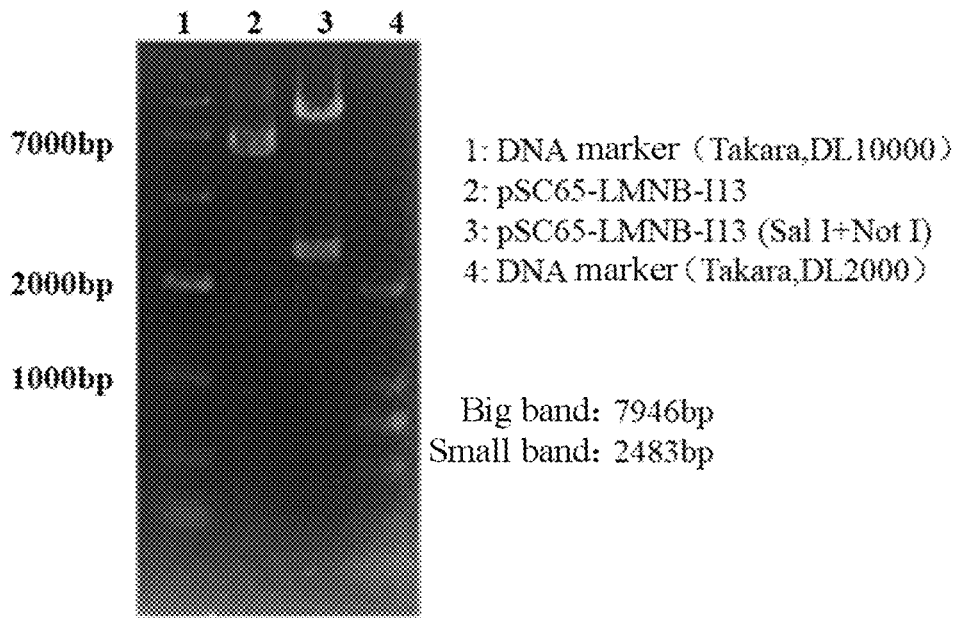

The vector pVKD1.0-hLMN-CTB expressing a fused triad of tumor antigens LAGE-1, MAGE-A3, NY-ESO-1 and cholera toxin subunit B was found in Example 2. Then the LMN-CTB fragment in the vector was digested by the enzymes Sal I and Kpn I for recovery and inserted into the aforesaid shuttle vector pSC65-I13 to construct the shuttle vector pSC65-LMNB-I13 (the plasmid map is shown in FIG. 32) expressing a triad of tumor antigens, which was stored after being sequenced for identification, wherein the amino acid sequence of LMNB-I13 is shown in SEQ ID NO: 62, and the eukaryotic codon optimized sequence thereof is shown in SEQ ID NO: 63. The vector pSC65-LMNB-I13 was identified by the restriction endonucleases Sal I and Kpn I (the enzyme digestion system is shown in Table 27), and its enzyme digestion map for verification is shown in FIG. 33.

TABLE 27

Enzyme digestion system for identification of plasmid pSC65V3 (enzyme digestion at 37° C., 2 h)

| Enzyme digestion system | Volume |
| --- | --- |
| Plasmid pSC65-LMNB-I13 | 3 μL, about 1 μg |
| Sal I (TaKaRa, Cat. No. 1080A) | 1 μL |
| Not I (TaKaRa, Cat. No. 1166A) | 1 μL |
| Enzyme digestion buffer | 1 μL |
| ddH$_2$O | q.s. to 10 μL |

Example 17 Construction of Recombinant Vaccinia Viral Vector rvv-LMNB-I13

The recombinant vaccinia viral vector was obtained from 143B cells according the following specific method. On the first day, 143B cells (provided by Vacdiagn Biotechnology Co., Ltd., Suzhou Industrial Park) were plated into a 6-well cell culture plate (JET, TCP-010-006), at 1×10$^6$ cells/well, and incubated overnight in a carbon dioxide cell incubator at 37° C. On the second day, wild vaccinia virus strains (provided by Beijing Institute of Biological Products Co., Ltd.) were added with 0.05 MOI (i.e., 5×10$^4$ PFU (plaque forming unit)/well), and then an incubation was conducted in the carbon dioxide cell incubator at 37° C. for 2 h, during which a shuttle vector/transfection reagent complex was prepared. The shuttle vector was pSC65-LMNB-I13 obtained in Example 16, the transfection reagent was Turbofect (Thermo Fisher Scientific, R0531), and the instructions of transfection reagent can be referred to for transfection dosage and complex method. After completion of the complex system, the supernatant of 143B cells was replaced with a DMEM maintenance medium containing 2% fetal bovine serum (FBS) at 2 mL/well, and then the shuttle vector/transfection reagent complex was added. After 48 h of transfection, the supernatant was removed, and the cells were collected, re-suspended in 0.5 mL the maintenance medium and frozen-thawed repeatedly for three times. Then the recombinant cell lysates were introduced into new 143B cells (with 50 μg/mL BrdU), followed by an incubation at 37° C. for 1 to 2 days. During this period, the cytopathic effects were observed, and when an appropriate number of virus plaques appeared (less than 20 plaques/well), purification of single plaque was carried out.

Purification of Single Plaque

2% low melting agarose was heated in a microwave oven (medium to high heat for about 2 min) to boiling, then transferred to a water bath at 45° C. and allowed to cool and prevented from solidification.

An appropriate amount of 2×maintenance medium (1 mL/well) was pipetted, an X-gal stock was added at a volume ratio of 1:50, followed by preheating in a water bath at 45° C.

Low melting point agarose and 2×maintenance medium containing X-gal were mixed in a ratio of equal volume to prepare a solid medium for plaque spread, the cell supernatant was removed, and the solid medium for plaque spread was carefully added. Then, the 6-well plate was transferred into a refrigerator for solidification at 4° C. for 10 min, without being moved to prevent from a non-uniform solidification during this period.

After complete solidification, the 6-well plate was transferred to a cell incubator and incubated at 37° C. for 2 to 4 h (sometimes overnight) until blue plaques appeared.

After the blue plaques appeared, the blue plaques which were well-dispersed and deeper in color were preferentially picked by using a 1 mL pipette tip (the pipette tip was trimmed by scissors in advance). The cell layer below the solid culture medium must be picked during picking, and a plurality of blue plaques were picked per well and transferred into Ep tubes containing 0.5 mL the maintenance medium, respectively.

The Ep tubes containing the virus were mixed uniformly by shaking, frozen and thawed three times repeatedly (in a refrigerator at −80° C. for about 5 min, and at room temperature for about 2 min), and finally mixed uniformly by shaking, frozen and stored at −80° C.

Six rounds of purification of single plaque were repeated until the purity reached 100%.

Example 18 Amplification Preparation and Titration of Recombinant Vaccinia Viral Vector Rvv-LMNB-I13

The recombinant vaccinia viral vector rvv-LMNB-I13 constructed in Example 17, and wild strain of vaccinia virus were amplified in Vero cells (provided by Vacdiagn Biotechnology Co., Ltd., Suzhou Industrial Park), respectively. The amplification method is as follows:

The day before, Vero monolayer cells with 100% confluence were prepared for a total of 10 dishes ($1 \times 10^7$ cells/dish).

The supernatant was removed and replaced with the maintenance medium. The vaccinia virus to be amplified was inoculated into the cells (0.01 PFU/cell) and incubated in an incubator at 37° C. for 2-3 days. A significant cytopathic effect was observed.

The cells were scraped off and collected, centrifuged at 1800 g for 5 min, and the supernatant was removed.

5 mL the maintenance medium was used for re-suspension, and an ultrasonic cell crusher was used to for ultrasonication on the ice. The ultrasonication conditions were as follows: 50 watts, 5 s ultrasonication/5 s interval, a total of 15 min.

Freezing and thawing were repeated two times (in a refrigerator at −80° C. for about 5 min, and at room temperature for about 2 min), followed by a final uniform mixing by shaking;

Aliquoting into 1.5 mL centrifuge tubes was carried out in a Class II biosafety cabinet, at 1 mL/tube, followed by freezing at −80° C.

The vaccinia virus prepared by amplification was subjected to a titration for infection titer on Vero cells, and the specific method was as follows.

The day before, Vero cells with 100% confluence were prepared in a 24-well plate, at $3 \times 10^5$ cells/well.

The supernatant was removed, and 200 μL the maintenance medium was added into each well to prevent the cells from cell dryout.

100 μL of vaccinia virus to be tested was added into 900 μL the maintenance medium, and subjected to 10 fold dilutions to be serially diluted $10^1$, $10^2$, $10^3$, up to $10^9$ folds. Note: with respect to the dilution, since it was conducted from a high concentration to a low concentration, the pipette tip should be replaced before each dilution to a lower concentration.

The virus was added into a 24-well plate at 400 μL dilution per well in duplicate with the concentration from low to high ($10^9$, $10^8$, ..., $10^4$), and the measurements were carried out serially for 6 dilution folds. After addition, the 24-well plate was placed and incubated in a cell incubator at 37° C. for 2 days.

The numbers of viral plaques were counted under a microscope, and the number of more than 20 was recorded as 20+. A recombinant virus titer (PFU/mL) was calculated as: an average of the numbers of plaques that can be counted as less than 20 (inclusive) in two duplicate wells×2.5 (1000 μL/400 μL)×dilution fold of the corresponding wells.

Titration results of vaccinia viral vector titer are shown in Table 28.

TABLE 28

| Titrations of vaccinia virus vector titer | |
|---|---|
| Vaccinia virus | Titer (PFU/mL) |
| Wild-type vaccinia virus rvv-wt | $1.5 \times 10^8$ |
| Recombinant vaccinia virus rvv-LMNB-I13 | $1.0 \times 10^8$ |

Example 19 Tumor Treatment Experiment 1

Twenty 6-8 weeks old female BAL B/c mice were purchased from the Laboratory Animal Center of Suzhou University and raised in the SPF animal house of the Laboratory Animal Center of Suzhou University. On day 0, all the mice were inoculated subcutaneously with a cell line stably transfected by the tumor cells CT26-MAGE-A3 expressing the MAGE-A3 tumor antigen (provided Vacdiagn Biotechnology Co., Ltd., Suzhou Industrial Park), at an inoculation dose of $2 \times 10^5$ cells/mouse, and then randomly divided into two groups. The vaccinia viral vector prepared in Example 18 was vaccinated into the tibialis anterior muscle of calf of the corresponding mice on the 1st, 14th and 28th day after the tumor cell inoculation (the specific vaccination scheme is shown in Table 29). The tumor growth was continuously observed and measured after the vaccination. The tumor volume was calculated according to the following formula: tumor volume (mm$^3$)=length×width/2. The mice were sacrificed when the tumor volume exceeded 10000 mm$^3$.

TABLE 29

Experimental animal grouping and vaccination schemes

| Grouping | Day 1 | | Day 14 | | Day 28 | |
|---|---|---|---|---|---|---|
| | Vaccine | Dose | Vaccine | Dose | Vaccine | Dose |
| Control Group (n = 10) | rvv-wt | $2 \times 10^6$ PFU | rvv-wt | $2 \times 10^6$ PFU | rvv-wt | $2 \times 10^6$ PFU |
| Treatment group (n = 10) | rvv-LMNB-I13 | $2 \times 10^6$ PFU | rvv-LMNB-I13 | $2 \times 10^6$ PFU | rvv-LMNB-I13 | $2 \times 10^6$ PFU |

Figure 34:
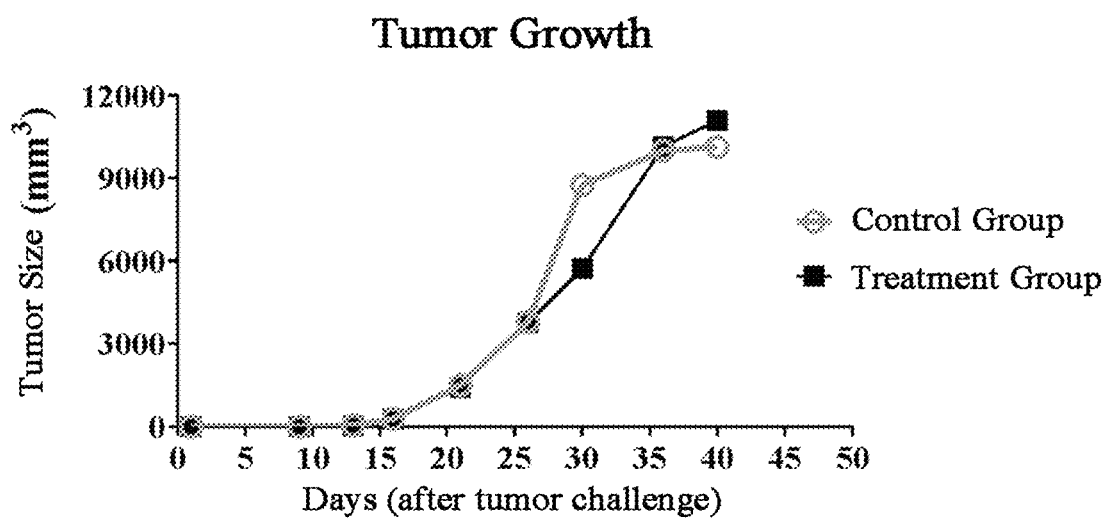
FIG. 34 shows the tumor growth of mice in each group for the CT26-MAGE-A3 mouse tumor model in Example 19.

The tumor growth of immunized mice in each group is shown in FIG. 34. Among them, all the mice in the control group developed the tumor on the 15th day after the tumor inoculation, which grew rapidly. On day 30 after the tumor challenge, the average tumor size of mice in the treatment group was significantly smaller than that in the control group. The results show that the vaccinia viral vector vaccine rvv-LMNB-I13 can inhibit the growth of tumors with MAGE-A3 expression.

Figure 35:
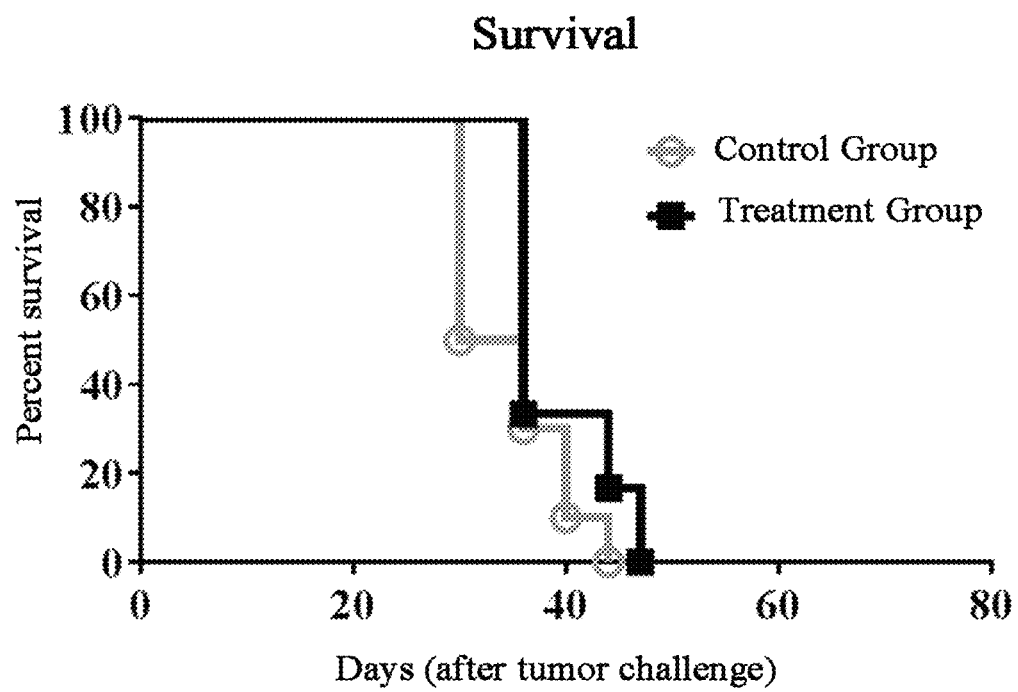
FIG. 35 shows the overall survival status of mice in each group for the CT26-MAGE-A3 mouse tumor model in Example 19.

The results of survival status of mice are shown by the survival curves in FIG. 35, and the overall survival of mice (the OS median: 36 days) in the group treated by the vaccinia viral vector vaccine rvv-LMNB-I13 was superior to that of mice in the control group (the OS median: 33 days, p<0.05). The results show that the vaccinia viral vector vaccine rvv-LMNB-I13 can improve the survival of mice having the tumors expressing MAGE-A3.

Example 20 Tumor Treatment Experiment 2

Twenty 6-8 weeks old female BAL B/c mice were purchased from the Laboratory Animal Center of Suzhou University and raised in the SPF animal house of the Laboratory Animal Center of Suzhou University. On day 0, all mice were inoculated subcutaneously with a cell line stably transfected by the tumor cells CT26-LAGE-1 expressing the LAGE-1 tumor antigen (provided by Vacdiagn Biotechnology Co., Ltd., Suzhou Industrial Park), at an inoculation dose of $1 \times 10^5$ cells/mouse, and then randomly divided into two groups. The vaccinia viral vector prepared in Example 18 was vaccinated into the tibialis anterior muscle of calf of the corresponding mice on the 1st, 14th and 28th day after the tumor cell inoculation (the specific vaccination scheme is shown in Table 30). The tumor growth was continuously observed and measured after the vaccination. The tumor volume was calculated according to the following formula: tumor volume (mm$^3$)=length×width/2. The mice were sacrificed when the tumor volume exceeded 10000 mm$^3$.

TABLE 30

Experimental animal grouping and vaccination schemes

| Grouping | Day 1 | | Day 14 | | Day 28 | |
|---|---|---|---|---|---|---|
| | Vaccine | Dose | Vaccine | Dose | Vaccine | Dose |
| Control Group (n = 10) | rvv-wt | $2 \times 10^6$ PFU | rvv-wt | $2 \times 10^6$ PFU | rvv-wt | $2 \times 10^6$ PFU |
| Treatment group (n = 10) | rvv-LMNB-I13 | $2 \times 10^6$ PFU | rvv-LMNB-I13 | $2 \times 10^6$ PFU | rvv-LMNB-I13 | $2 \times 10^6$ PFU |

Figure 36:
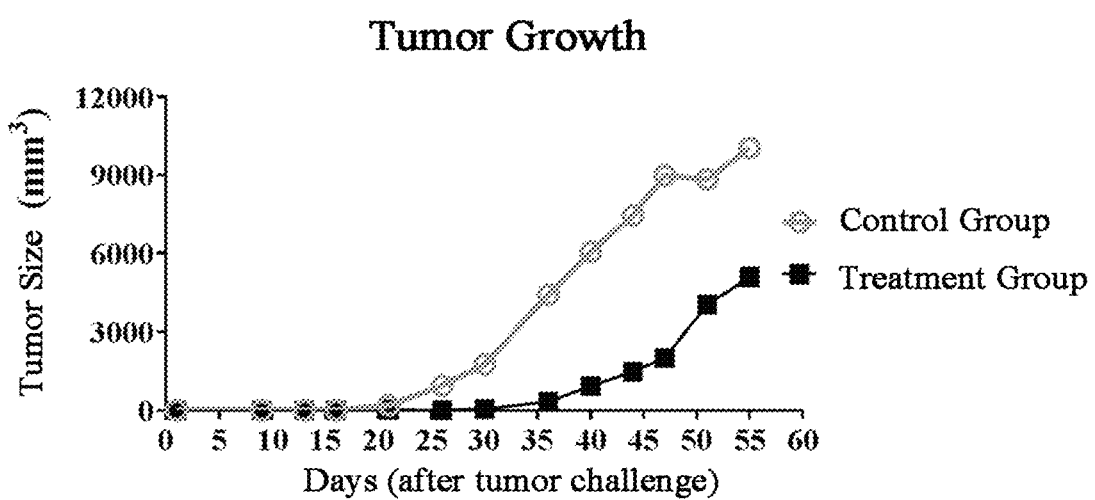
FIG. 36 shows the tumor growth of mice in each group for the CT26-LAGE-1 mouse tumor model in Example 20.

The tumor growth of immunized mice in each group is shown in FIG. 36. On day 26 after the tumor challenge, the tumor of mice in the control group grew rapidly and was significantly larger than that of mice in the treatment group until day 50. The results show that the vaccinia viral vector vaccine rvv-LMNB-I13 can inhibit the growth of tumors with LAGE-1 expression.

Figure 37:
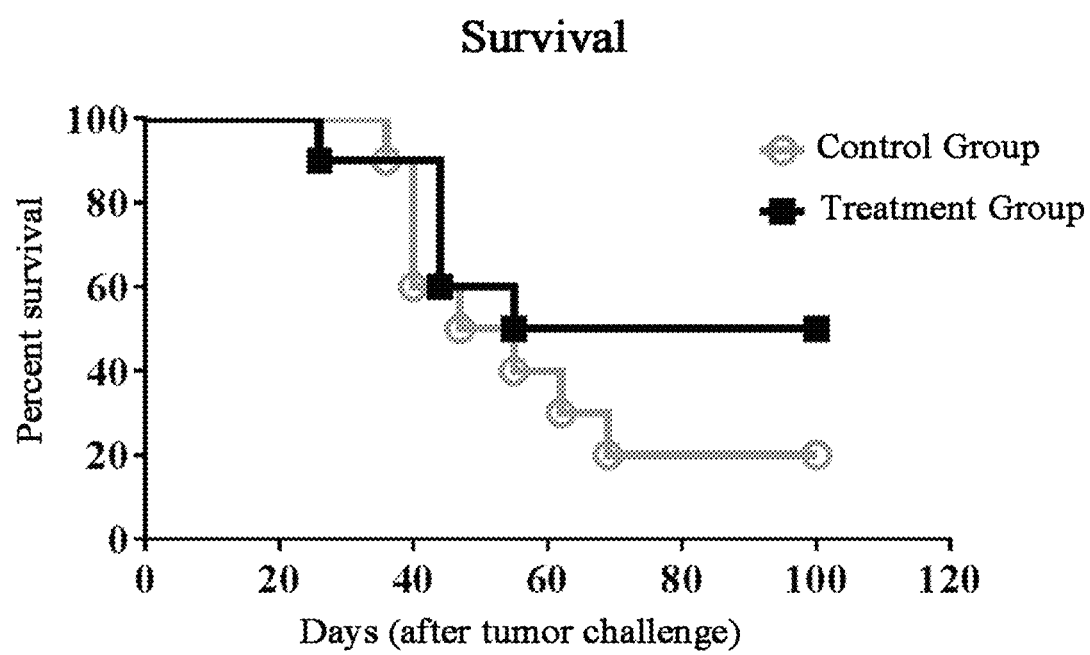
FIG. 37 shows the overall survival status of mice in each group for the CT26-LAGE-1 mouse tumor model in Example 20.

In addition, the results of survival status of mice are shown by the survival curves in FIG. 37, and the overall survival of mice (the OS median: 75 days) in the group treated by the vaccinia viral vector vaccine rvv-LMNB-I13 was superior to that of mice in the control group (the OS median: 51 days, p<0.05). The results show that the vaccinia viral vector vaccine rvv-LMNB-I13 can improve the survival of mice having the tumors expressing LAGE-1.

A comparison between the immune effects of protein vaccines in Examples 13-15 and the treatment effects of recombinant vaccinia viral vectors in Examples 19-20 shows that the protein vaccines had a significant effect in preventing tumors (see FIGS. 27, 28 and 29). Although the protein vaccines maintained a certain therapeutic effect in tumor treatment, the therapeutic effect was not particularly significant and could not be sustained (see FIG. 30 and FIG. 31). The recombinant vaccinia viral vector had achieved a particularly significant effect in tumor treatment, not only a sustained inhibition of tumor growth, but also a significant improvement in overall survival, which were prominent effects (see FIG. 34-37).

The invention claimed is:

1. A recombinant viral vector comprising a polynucleotide encoding a fusion peptide of CD4 helper T cell epitopes, the fusion peptide of CD4 helper T cell epitopes having the amino acid sequence shown in SEQ ID NO: 60, wherein the recombinant virus vector is a vaccinia virus vector.

2. The recombinant viral vector of claim 1, further comprising a polynucleotide encoding a target immunogen.

3. The recombinant viral vector of claim 2, wherein the target immunogen is selected from a peptide, an antigen, a hapten, a carbohydrate, a protein, a nucleic acid, an allergen, a virus or a part of a virus, a bacterium, a parasite or other whole microorganism.

4. A fusion peptide of CD4 helper T cell epitopes having the amino acid sequence shown in SEQ ID NO: 60.

5. A fusion protein comprising the epitope fusion peptide of claim 4 and a target immunogen.

6. An immunogenic composition comprising a therapeutically effective amount of the recombinant viral vector of claim 1, and a pharmaceutically acceptable carrier.

7. The immunogenic composition of claim 6 in the form of a vaccine.

8. A kit comprising the recombinant viral vector of claim 1 and instructions for use thereof.

9. A method for increasing the immunogenicity of a target immunogen in a subject in need thereof, comprising administering the recombinant viral vector of claim 1 to the subject.

10. A method for treating or preventing a condition in a subject in need thereof, comprising administering a prophylactically or therapeutically amount of the recombinant viral vector of claim 1 to the subject, wherein the condition is one or more conditions selected from malignant tumors, and bacterial and viral infections.

11. The recombinant viral vector of claim 3, wherein the antigen is LAGE-1 or MAGE-A3.

12. The fusion protein of claim 5, wherein the fusion protein has the amino acid sequence shown in SEQ ID NO: 62.

* * * * *

```
                      SEQUENCE LISTING

<160> NUMBER OF SEQ ID NOS: 63

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Leu Leu Gln Thr Gly Ile His Val Arg Val Ser Gln Pro Ser Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Ile Ile Lys Pro Gly Lys Ile Ser His Ile Met Leu Asp Val Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Glu His Pro Thr Phe Thr Ser Gln Tyr Arg Ile Gln Gly Lys Leu
1               5                   10                  15

<210> SEQ ID NO 4
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 4

Ala Gly Ile Leu Ala Arg Asn Leu Val Pro Met Val Ala Thr Val
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Lys Tyr Gln Glu Phe Phe Trp Asp Ala Asn Asp Ile Tyr Arg Ile
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Lys Val Tyr Leu Glu Ser Phe Cys Glu Asp Val Pro Ser Gly Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Thr Leu Gly Ser Asp Val Glu Glu Asp Leu Thr Met Thr Arg Asn
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Pro Leu Lys Met Leu Asn Ile Pro Ser Ile Asn Val His His Tyr
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Ala Cys Thr Ser Gly Val Met Thr Arg Gly Arg Leu Lys Ala Glu
1               5                   10                  15

<210> SEQ ID NO 10
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 10

Thr Glu Arg Lys Thr Pro Arg Val Thr Gly Gly Gly Ala Met Ala
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Asn Gln Arg Ala Leu Tyr His Thr Glu Asn Ala Tyr Val Ser Val Val
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

Ser Asp Met Arg Ala Glu Ile Ile Lys Met Met Glu Ser Ala Arg Pro
1               5                   10                  15

Glu

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Ala Leu Ala Ser Arg Tyr Leu Thr Asp Met Thr Ile Glu Glu Met Ser
1               5                   10                  15

Arg

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Leu Ala Ser Thr Thr Ala Lys Ala Met Glu Gln Met Ala Gly Ser Ser
1               5                   10                  15

Glu

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15
```

Ser Gly Tyr Ala Ala Asp Gln Lys Ser Thr Gln Asn Ala Ile Asn Gly
1               5                   10                  15

Ile Thr Asn Lys Val Asn
            20

<210> SEQ ID NO 16
<211> LENGTH: 18
<212> TYPE: PRT
<213> ORGANISM: Artificial Sequence
<220> FEATURE:
<223> OTHER INFORMATION: Synthetic

<400> SEQUENCE: 16

Glu Ile Arg Ala Ser Val Gly Lys Met Ile Asp Gly Ile Gly Arg Phe
1               5                   10                  15

Tyr Ile

<210> SEQ ID NO 17
<211> LENGTH: 17
<212> TYPE: PRT
<213> ORGANISM: Artificial Sequence
<220> FEATURE:
<223> OTHER INFORMATION: Synthetic

<400> SEQUENCE: 17

Pro Ile Tyr Arg Arg Val Asp Gly Lys Trp Met Arg Glu Leu Val Leu
1               5                   10                  15

Tyr

<210> SEQ ID NO 18
<211> LENGTH: 18
<212> TYPE: PRT
<213> ORGANISM: Artificial Sequence
<220> FEATURE:
<223> OTHER INFORMATION: Synthetic

<400> SEQUENCE: 18

Arg Met Cys Asn Ile Leu Lys Gly Lys Phe Gln Thr Ala Ala Gln Arg
1               5                   10                  15

Ala Met

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Ile Trp Thr Tyr Asn Ala Glu Leu Leu Val Leu Leu Glu Asn Glu Arg
1               5                   10                  15

Thr

<210> SEQ ID NO 20
<211> LENGTH: 17
<212> TYPE: PRT
<213> ORGANISM: Artificial Sequence
<220> FEATURE:
<223> OTHER INFORMATION: Synthetic

<400> SEQUENCE: 20

Glu Leu Leu Val Leu Leu Glu Asn Glu Arg Thr Leu Asp Phe His Asp
1               5                   10                  15

Ser

<210> SEQ ID NO 21
<211> LENGTH: 17
<212> TYPE: PRT
<213> ORGANISM: Artificial Sequence
<220> FEATURE:
<223> OTHER INFORMATION: Synthetic

<400> SEQUENCE: 21

```
His Lys Ser Gln Leu Val Trp Met Ala Cys Asn Ser Ala Ala Phe Glu
1               5                   10                  15

Asp
```

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

```
Cys Met Gly Leu Ile Tyr Asn Arg Met Gly Ala Val Thr Thr Glu Ser
1               5                   10                  15

Ala
```

<210> SEQ ID NO 23
<211> LENGTH: 23
<212> TYPE: PRT
<213> ORGANISM: Artificial Sequence
<220> FEATURE:
<223> OTHER INFORMATION: Synthetic

<400> SEQUENCE: 23

```
Arg Gln Met Val Gln Ala Met Arg Ala Ile Gly Thr His Pro Ser Ser
1               5                   10                  15

Ser Thr Gly Leu Lys Asn Asp
            20
```

<210> SEQ ID NO 24
<211> LENGTH: 210
<212> TYPE: PRT
<213> ORGANISM: Artificial Sequence
<220> FEATURE:
<223> OTHER INFORMATION: Synthetic

<400> SEQUENCE: 24

```
Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Glu Leu His Ile Thr Met Pro Phe
                85                  90                  95

Ser Ser Pro Met Glu Ala Glu Leu Val Arg Arg Ile Leu Ser Arg Asp
            100                 105                 110
```

```
Ala Ala Pro Leu Pro Arg Pro Gly Ala Val Leu Lys Asp Phe Thr Val
        115                 120                 125

Ser Gly Asn Leu Leu Phe Met Ser Val Arg Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
                180                 185                 190

Gly Asp Gly Cys Arg Gly Val Ala Phe Asn Val Met Phe Ser Ala Pro
        195                 200                 205

His Ile
    210

<210> SEQ ID NO 25
<211> LENGTH: 313
<212> TYPE: PRT
<213> ORGANISM: Artificial Sequence
<220> FEATURE:
<223> OTHER INFORMATION: Synthetic

<400> SEQUENCE: 25

Pro Leu Glu Gln Arg Ser Gln His Cys Lys Pro Glu Glu Gly Leu Glu
1               5                   10                  15

Ala Arg Gly Glu Ala Leu Gly Leu Val Gly Ala Gln Ala Pro Ala Thr
                20                  25                  30

Glu Glu Gln Glu Ala Ala Ser Ser Ser Thr Leu Val Glu Val Thr
            35                  40                  45

Leu Gly Glu Val Pro Ala Ala Glu Ser Pro Asp Pro Pro Gln Ser Pro
    50                  55                  60

Gln Gly Ala Ser Ser Leu Pro Thr Thr Met Asn Tyr Pro Leu Trp Ser
65                  70                  75                  80

Gln Ser Tyr Glu Asp Ser Ser Asn Gln Glu Glu Glu Gly Pro Ser Thr
                85                  90                  95

Phe Pro Asp Leu Glu Ser Glu Phe Gln Ala Ala Leu Ser Arg Lys Val
            100                 105                 110

Ala Glu Leu Val His Phe Leu Leu Leu Lys Tyr Arg Ala Arg Glu Pro
        115                 120                 125

Val Thr Lys Ala Glu Met Leu Gly Ser Val Val Gly Asn Trp Gln Tyr
    130                 135                 140

Phe Phe Pro Val Ile Phe Ser Lys Ala Ser Ser Ser Leu Gln Leu Val
145                 150                 155                 160

Phe Gly Ile Glu Leu Met Glu Val Asp Pro Ile Gly His Leu Tyr Ile
                165                 170                 175

Phe Ala Thr Cys Leu Gly Leu Ser Tyr Asp Gly Leu Leu Gly Asp Asn
            180                 185                 190

Gln Ile Met Pro Lys Ala Gly Leu Leu Ile Ile Val Leu Ala Ile Ile
        195                 200                 205

Ala Arg Glu Gly Asp Cys Ala Pro Glu Glu Lys Ile Trp Glu Glu Leu
    210                 215                 220

Ser Val Leu Glu Val Phe Glu Gly Arg Glu Asp Ser Ile Leu Gly Asp
225                 230                 235                 240

Pro Lys Lys Leu Leu Thr Gln His Phe Val Gln Glu Asn Tyr Leu Glu
                245                 250                 255
```

Tyr Arg Gln Val Pro Gly Ser Asp Pro Ala Cys Tyr Glu Phe Leu Trp
            260                 265                 270

Gly Pro Arg Ala Leu Val Glu Thr Ser Tyr Val Lys Val Leu His His
        275                 280                 285

Met Val Lys Ile Ser Gly Gly Pro His Ile Ser Tyr Pro Pro Leu His
290                 295                 300

Glu Trp Val Leu Arg Glu Gly Glu Glu
305                 310

<210> SEQ ID NO 26
<211> LENGTH: 179
<212> TYPE: PRT
<213> ORGANISM: Artificial Sequence
<220> FEATURE:
<223> OTHER INFORMATION: Synthetic

<400> SEQUENCE: 26

Gln Ala Glu Gly Arg Gly Thr Gly Gly Ser Thr Gly Asp Ala Asp Gly
1               5                   10                  15

Pro Gly Gly Pro Gly Ile Pro Asp Gly Pro Gly Gly Asn Ala Gly Gly
            20                  25                  30

Pro Gly Glu Ala Gly Ala Thr Gly Gly Arg Gly Pro Arg Gly Ala Gly
        35                  40                  45

Ala Ala Arg Ala Ser Gly Pro Gly Gly Ala Pro Gly Pro His
    50                  55                  60

Gly Gly Ala Ala Ser Gly Leu Asn Gly Cys Cys Arg Cys Gly Ala Arg
65                  70                  75                  80

Gly Pro Glu Ser Arg Leu Leu Glu Phe Tyr Leu Ala Met Pro Phe Ala
                85                  90                  95

Thr Pro Met Glu Ala Glu Leu Ala Arg Arg Ser Leu Ala Gln Asp Ala
            100                 105                 110

Pro Pro Leu Pro Val Pro Gly Val Leu Leu Lys Glu Phe Thr Val Ser
        115                 120                 125

Gly Asn Ile Leu Thr Ile Arg Leu Thr Ala Ala Asp His Arg Gln Leu
130                 135                 140

Gln Leu Ser Ile Ser Ser Cys Leu Gln Gln Leu Ser Leu Leu Met Trp
145                 150                 155                 160

Ile Thr Gln Cys Phe Leu Pro Val Phe Leu Ala Gln Pro Pro Ser Gly
                165                 170                 175

Gln Arg Arg

<210> SEQ ID NO 27
<211> LENGTH: 630
<212> TYPE: DNA
<213> ORGANISM: Artificial Sequence
<220> FEATURE:
<223> OTHER INFORMATION: Synthetic

<400> SEQUENCE: 27
atgcaggccg aaggccgggg cacagggggt tcgacgggcg atgctgatgg cccaggaggc      60
cctggcattc ctgatggccc agggggcaat gctggcggcc aggagaggc gggtgccacg     120 ggcggcagag gtccccgggg cgcaggggca gcaagggcct cggggccgag aggaggcgcc     180
ccgcggggtc cgcatggcgg tgccgcttct gcgcaggatg aaggtgccc ctgcggggcc     240 aggaggccgg acagccgcct gcttgagttg cacatcacga tgccctttctc gtcgccaatg     300 gaagcggagc tggtccgcag aatcctgtcc cgggatgccg caccgctccc ccgaccaggg     360

```
gcggttctga aggacttcac cgtgtccggc aacctactgt ttatgtcagt tcgggaccag    420
gacagggaag gcgctgggcg gatgagggtg gtgggttggg ggctgggatc agcctccccg    480
gaggggcaga aagctagaga tctcagaaca cccaaacaca aggtctcaga acagagacct    540
ggtacaccag gcccgccgcc acccgaggga gcccagggag atgggtgcag aggtgtcgcc    600
tttaatgtga tgttctctgc ccctcacatt                                    630
```

<210> SEQ ID NO 28
<211> LENGTH: 939
<212> TYPE: DNA
<213> ORGANISM: Artificial Sequence
<220> FEATURE:
<223> OTHER INFORMATION: Synthetic

<400> SEQUENCE: 28

```
cccctggagc agcgcagcca gcactgcaag cccgaggagg gcctggaggc ccgcggcgag     60
gccctgggcc tggtgggcgc ccaggccccc gccaccgagg agcaggaggc cgccagcagc    120
agcagcaccc tggtggaggt gaccctgggc gaggtgcccg ccgccgagag ccccgacccc    180
ccccagagcc cccagggcgc cagcagcctg cccaccacca tgaactaccc cctgtggagc    240
cagagctacg aggacagcag caaccaggag gaggagggcc ccagcaccct ccccgacctg    300
gagagcgagt ccaggccgc cctgagccgc aaggtggccg agctggtgca cttcctgctg    360
ctgaagtacc gcgcccgcga gcccgtgacc aaggccgaga tgctgggcag cgtggtgggc    420
aactggcagt acttcttccc cgtgatcttc agcaaggcca gcagcagcct gcagctggtg    480
ttcggcatcg agctgatgga ggtggacccc atcggccacc tgtacatctt cgccacctgc    540
ctgggcctga gctacgacgg cctgctgggc gacaaccaga tcatgcccaa ggccggcctg    600
ctgatcatcg tgctggccat catcgcccgc gagggcgact gcgcccccga ggagaagatc    660
tgggaggagc tgagcgtgct ggaggtgttc gagggccgcg aggacagcat cctgggcgac    720
cccaagaagc tgctgaccca gcacttcgtg caggagaact acctggagta ccgccaggtg    780
cccggcagcg accccgcctg ctacgagttc ctgtggggcc ccgcgccct ggtggagacc    840 agctacgtga aggtgctgca ccacatggtg aagatcagcg cggccccca catcagctac    900 cccccccctgc acgagtgggt gctgcgcgag ggcgaggag                         939
```

<210> SEQ ID NO 29
<211> LENGTH: 537
<212> TYPE: DNA
<213> ORGANISM: Artificial Sequence
<220> FEATURE:
<223> OTHER INFORMATION: Synthetic

<400> SEQUENCE: 29

```
caggccgaag gccggggcac aggggttcg acgggcgatg ctgatggccc aggaggccct     60
ggcattcctg atggcccagg gggcaatgct ggcggcccag gagaggcggg tgccacgggc    120
ggcagaggtc cccggggcgc aggggcagca agggcctcgg ggccgggagg aggcgccccg    180
cggggtccgc atggcggcgc ggcttcaggg ctgaatggat gctgcagatg cggggccagg    240
gggccggaga gccgcctgct tgagttctac ctcgccatgc ctttcgcgac acccatggaa    300
gcagagctgg cccgcaggag cctggcccag gatgcccac cgcttcccgt gccaggggtg    360
cttctgaagg agttcactgt gtccggcaac atactgacta tccgactgac tgctgcagac    420
caccgccaac tgcagctctc catcagctcc tgtctccagc agctttccct gttgatgtgg    480
```

```
atcacgcagt gctttctgcc cgtgttttg gctcagcctc cctcagggca gaggcgc        537
```

<210> SEQ ID NO 30
<211> LENGTH: 123
<212> TYPE: PRT
<213> ORGANISM: Artificial Sequence
<220> FEATURE:
<223> OTHER INFORMATION: Synthetic

<400> SEQUENCE: 30

```
Ile Lys Leu Lys Phe Gly Val Phe Phe Thr Val Leu Leu Ser Ser Ala
1               5                   10                  15

Tyr Ala His Gly Thr Pro Gln Asn Ile Thr Asp Leu Cys Ala Glu Tyr
            20                  25                  30

His Asn Thr Gln Ile His Thr Leu Asn Asp Lys Ile Phe Ser Tyr Thr
        35                  40                  45

Glu Ser Leu Ala Gly Lys Arg Glu Met Ala Ile Ile Thr Phe Lys Asn
    50                  55                  60

Gly Ala Thr Phe Gln Val Glu Val Pro Gly Ser Gln His Ile Asp Ser
65                  70                  75                  80

Gln Lys Lys Ala Ile Glu Arg Met Lys Asp Thr Leu Arg Ile Ala Tyr
                85                  90                  95

Leu Thr Glu Ala Lys Val Glu Lys Leu Cys Val Trp Asn Asn Lys Thr
            100                 105                 110

Pro His Ala Ile Ala Ala Ile Ser Met Ala Asn
        115                 120
```

<210> SEQ ID NO 31
<211> LENGTH: 369
<212> TYPE: DNA
<213> ORGANISM: Artificial Sequence
<220> FEATURE:
<223> OTHER INFORMATION: Synthetic

<400> SEQUENCE: 31

```
atcaagctga agttcggcgt gttcttcacc gtgctgctga gcagcgccta cgcccacggc        60
acccccagaa acatcaccga cctgtgcgcc gagtaccaca cacccagat ccacaccctg       120
aacgacaaga tcttcagcta caccgagagc ctggccggca agcgcgagat ggccatcatc       180
accttcaaga acggcgccac cttccaggtg gaggtgcccg gcagccagca catcgacagc       240
cagaagaagg ccatcgagcg catgaaggac accctgcgca tcgcctacct gaccgaggcc       300
aaggtggaga gctgtgcgt gtggaacaac aagacccccc acgccatcgc cgccatcagc       360
atggccaac                                                              369
```

<210> SEQ ID NO 32
<211> LENGTH: 40
<212> TYPE: DNA
<213> ORGANISM: Artificial Sequence
<220> FEATURE:
<223> OTHER INFORMATION: Synthetic

<400> SEQUENCE: 32

```
tccctcaggg cagaggcgca tcaagctgaa gttcggcgtg                             40
```

<210> SEQ ID NO 33
<211> LENGTH: 44
<212> TYPE: DNA
<213> ORGANISM: Artificial Sequence
<220> FEATURE:
<223> OTHER INFORMATION: Synthetic

<400> SEQUENCE: 33
gaaggcacag cagatctgga tcctcagttg gccatgctga tggc 44

<210> SEQ ID NO 34
<211> LENGTH: 219
<212> TYPE: PRT
<213> ORGANISM: Artificial Sequence
<220> FEATURE:
<223> OTHER INFORMATION: Synthetic

<400> SEQUENCE: 34

```
Met Leu Leu Gln Thr Gly Ile His Val Arg Val Ser Gln Pro Ser Leu
1               5                  10                  15

Ile Ile Lys Pro Gly Lys Ile Ser His Ile Met Leu Asp Val Ala Glu
            20                  25                  30

His Pro Thr Phe Thr Ser Gln Tyr Arg Ile Gln Gly Lys Leu Ala Gly
        35                  40                  45

Ile Leu Ala Arg Asn Leu Val Pro Met Val Ala Thr Val Lys Tyr Gln
    50                  55                  60

Glu Phe Phe Trp Asp Ala Asn Asp Ile Tyr Arg Ile Asn Gln Arg Ala
65                  70                  75                  80

Leu Tyr His Thr Glu Asn Ala Tyr Val Ser Val Val Ser Ser Asp Met
                85                  90                  95

Arg Ala Glu Ile Ile Lys Met Met Glu Ser Ala Arg Pro Glu Ala Leu
            100                 105                 110

Ala Ser Arg Tyr Leu Thr Asp Met Thr Ile Glu Glu Met Ser Arg Leu
        115                 120                 125

Ala Ser Thr Thr Ala Lys Ala Met Glu Gln Met Ala Gly Ser Ser Glu
    130                 135                 140

Ser Gly Tyr Ala Ala Asp Gln Lys Ser Thr Gln Asn Ala Ile Asn Gly
145                 150                 155                 160

Ile Thr Asn Lys Val Asn Glu Ile Arg Ala Ser Val Gly Lys Met Ile
                165                 170                 175

Asp Gly Ile Gly Arg Phe Tyr Ile Pro Ile Tyr Arg Arg Val Asp Gly
            180                 185                 190

Lys Trp Met Arg Glu Leu Val Leu Tyr Arg Met Cys Asn Ile Leu Lys
        195                 200                 205

Gly Lys Phe Gln Thr Ala Ala Gln Arg Ala Met
    210                 215
```

<210> SEQ ID NO 35
<211> LENGTH: 657
<212> TYPE: DNA
<213> ORGANISM: Artificial Sequence
<220> FEATURE:
<223> OTHER INFORMATION: Synthetic

<400> SEQUENCE: 35
atgctgctgc aaaccggcat ccacgtgcgc gtgagccagc ccagcctgat catcaagccc 60
ggcaagatca gccacatcat gctggacgtg gccgagcacc ccaccttcac cagccagtac 120
cgcatccagg gcaagctggc cggcatcctg gcccgcaacc tggtgcccat ggtggccacc 180
gtgaagtacc aggagttctt ctgggacgcc aacgacatct accgcatcaa ccagcgcgcc 240
ctgtaccaca ccgagaacgc ctacgtgagc gtggtgagca gcgacatgcg cgccgagatc 300
atcaagatga tggagagcgc ccgccccgag gccctggcca gccgctacct gaccgacatg 360

| | |
|---|---|
| accatcgagg agatgagccg cctggccagc accaccgcca aggccatgga gcagatggcc | 420 |
| ggcagcagcg agagcggcta cgccgccgac cagaagagca cccagaacgc catcaacggc | 480 |
| atcaccaaca aggtgaacga gatccgcgcc agcgtgggca gatgatcga cggcatcggc | 540 |
| cgcttctaca tccccatcta ccgcgcgtg gacggcaagt ggatgcgcga gctggtgctg | 600 |
| taccgcatgt gcaacatcct gaagggcaag ttccagaccg ccgcccagcg cgccatg | 657 |

<210> SEQ ID NO 36
<211> LENGTH: 38
<212> TYPE: DNA
<213> ORGANISM: Artificial Sequence
<220> FEATURE:
<223> OTHER INFORMATION: Synthetic

<400> SEQUENCE: 36

| | |
|---|---|
| gcgcggccgc tgtcaccgtc gtcgacatgc aggccgaa | 38 |

<210> SEQ ID NO 37
<211> LENGTH: 35
<212> TYPE: DNA
<213> ORGANISM: Artificial Sequence
<220> FEATURE:
<223> OTHER INFORMATION: Synthetic

<400> SEQUENCE: 37

| | |
|---|---|
| gcgatcctca gttggccatg ctgatggcgg cgatg | 35 |

<210> SEQ ID NO 38
<211> LENGTH: 630
<212> TYPE: DNA
<213> ORGANISM: Artificial Sequence
<220> FEATURE:
<223> OTHER INFORMATION: Synthetic

<400> SEQUENCE: 38

| | |
|---|---|
| atgcaggctg aaggtcgtgg taccggtggt tctaccggtg acgctgacgg tccgggtggt | 60 |
| ccgggtatcc cggacggtcc gggtggtaac gctggtggtc cgggtgaagc tggtgctacc | 120 |
| ggtggtcgtg gtccgcgtgg tgctggtgct gctcgtgctt ctggtccgcg tggtggtgct | 180 |
| ccgcgtggtc cgcacggtgg tgctgcttct gctcaggacg tcgttgccc gtgcggtgct | 240 |
| cgtcgtccgg actctcgtct gctggaactg cacatcacca tgccgttctc ttctccgatg | 300 |
| gaagctgaac tggttcgtcg tatcctgtct cgtgacgctg ctccgctgcc gcgtccgggt | 360 |
| gctgttctga aagacttcac cgtttctggt aacctgctgt tcatgtctgt tcgtgaccag | 420 |
| gaccgtgaag gtgctggtcg tatgcgtgtt gttggttggg gtctgggttc tgcttctccg | 480 |
| gaaggtcaga aagctcgtga cctgcgtacc ccgaaacaca agtttctga acagcgtccg | 540 |
| ggtaccccgg gtccgccgcc gccggaaggt gctcagggtg acggttgccg tggtgttgct | 600 |
| ttcaacgtta tgttctctgc tccgcacatc | 630 |

<210> SEQ ID NO 39
<211> LENGTH: 939
<212> TYPE: DNA
<213> ORGANISM: Artificial Sequence
<220> FEATURE:
<223> OTHER INFORMATION: Synthetic

<400> SEQUENCE: 39

| | |
|---|---|
| ccgctggaac agcgttctca gcactgcaaa ccggaagaag gtctggaagc tcgtggtgaa | 60 |
| gctctgggtc tggttggtgc tcaggctccg gctaccgaag aacaggaagc tgcttcttct | 120 |

```
tcttctaccc tggttgaagt taccctgggt gaagttccgg ctgctgaatc tccggacccg    180
ccgcagtctc cgcagggtgc ttcttctctg ccgaccacca tgaactaccc gctgtggtct    240
cagtcttacg aagactcttc taaccaggaa gaagaaggtc cgtctacctt cccggacctg    300
gaatctgaat tccaggctgc tctgtctcgt aaagttgctg aactggttca cttcctgctg    360
ctgaaatacc gtgctcgtga accggttacc aaagctgaaa tgctgggttc tgttgttggt    420
aactggcagt acttcttccc ggttatcttc tctaaagctt cttcttctct gcagctggtt    480
ttcggtatcg aactgatgga agttgacccg atcggtcacc tgtacatctt cgctacctgc    540
ctgggtctgt cttacgacgg tctgctgggt gacaaccaga tcatgccgaa agctggtctg    600
ctgatcatcg ttctggctat catcgctcgt gaaggtgact gcgctccgga agaaaaaatc    660
tgggaagaac tgtctgttct ggaagttttc gaaggtcgtg aagactctat cctgggtgac    720
ccgaaaaaac tgctgaccca gcacttcgtt caggaaaact acctggaata ccgtcaggtt    780
ccgggttctg acccggcttg ctacgaattc ctgtgggtc cgcgtgctct ggttgaaacc    840
tcttacgtta aagttctgca ccacatggtt aaaatctctg gtggtccgca catctcttac    900
ccgccgctgc acgaatgggt tctgcgtgaa ggtgaagaa                           939

<210> SEQ ID NO 40
<211> LENGTH: 540
<212> TYPE: DNA
<213> ORGANISM: Artificial Sequence
<220> FEATURE:
<223> OTHER INFORMATION: Synthetic

<400> SEQUENCE: 40
gctcaggctg aaggtcgtgg taccggtggt tctaccggtg acgctgacgg tccgggtggt     60
ccgggtatcc cggacggtcc gggtggtaac gctggtggtc cgggtgaagc tggtgctacc    120
ggtggtcgtg gtccgcgtgg tgctggtgct gctcgtgctt ctggtccggg tggtggtgct    180
ccgcgtggtc cgcacggtgg tgctgcttct ggtctgaacg gttgctgccg ttgcggtgct    240
cgtggtccgg aatctcgtct gctggaattc tacctggcta tgccgttcgc taccccgatg    300
gaagctgaac tggctcgtcg ttctctggct caggacgctc cgccgctgcc ggttccgggt    360
gttctgctga agaattcac cgtttctggt aacatcctga ccatccgtct gaccgctgct    420
gaccaccgtc agctgcagct gtctatctct tcttgcctgc agcagctgtc tctgctgatg    480
tggatcaccc agtgcttcct gccggttttc ctggctcagc cgccgtctgg tcagcgtcgt    540

<210> SEQ ID NO 41
<211> LENGTH: 369
<212> TYPE: DNA
<213> ORGANISM: Artificial Sequence
<220> FEATURE:
<223> OTHER INFORMATION: Synthetic

<400> SEQUENCE: 41
atcaaactga atttggcgt cttcttcacc gtcctgctgt cttctgctta cgtctcacggt     60 accccgcaga acatcaccga cctgtgcgct gaataccaca acacccagat ccacaccctg    120
aacgacaaaa tcttctctta caccgaatct ctggctggta acgtgaaat ggctatcatc    180 accttcaaaa acggtgctac cttccaggtt gaagttccgg ttctcagca catcgactct    240 cagaaaaaag ctatcgaacg tatgaaagac ccctgcgta tcgcttacct gaccgaagct    300
aaagttgaaa actgtgcgt ttggaacaac aaaacccgc acgctatcgc tgctatctct    360
``` atggctaac                                                           369

<210> SEQ ID NO 42
<211> LENGTH: 36
<212> TYPE: DNA
<213> ORGANISM: Artificial Sequence
<220> FEATURE:
<223> OTHER INFORMATION: Synthetic

<400> SEQUENCE: 42
ggtggtggtg gtgctcgagt tagttagcca tagaga                             36

<210> SEQ ID NO 43
<211> LENGTH: 39
<212> TYPE: DNA
<213> ORGANISM: Artificial Sequence
<220> FEATURE:
<223> OTHER INFORMATION: Synthetic

<400> SEQUENCE: 43
tctgcgtgaa ggtgaagaag ctcaggctga aggtcgtgg                          39

<210> SEQ ID NO 44
<211> LENGTH: 157
<212> TYPE: PRT
<213> ORGANISM: Artificial Sequence
<220> FEATURE:
<223> OTHER INFORMATION: Synthetic

<400> SEQUENCE: 44

Leu Leu Gln Thr Gly Ile His Val Arg Val Ser Gln Pro Ser Leu Ile
1               5                   10                  15

Ile Lys Pro Gly Lys Ile Ser His Ile Met Leu Asp Val Ala Glu His
            20                  25                  30

Pro Thr Phe Thr Ser Gln Tyr Arg Ile Gln Gly Lys Leu Ala Gly Ile
        35                  40                  45

Leu Ala Arg Asn Leu Val Pro Met Val Ala Thr Val Lys Tyr Gln Glu
    50                  55                  60

Phe Phe Trp Asp Ala Asn Asp Ile Tyr Arg Ile Glu Phe Glu Leu Arg
65                  70                  75                  80

Arg Gln Lys Val Tyr Leu Glu Ser Phe Cys Glu Asp Val Pro Ser Gly
                85                  90                  95

Lys Thr Leu Gly Ser Asp Val Glu Glu Asp Leu Thr Met Thr Arg Asn
            100                 105                 110

Pro Leu Lys Met Leu Asn Ile Pro Ser Ile Asn Val His His Tyr Ala
        115                 120                 125

Cys Thr Ser Gly Val Met Thr Arg Gly Arg Leu Lys Ala Glu Thr Glu
    130                 135                 140

Arg Lys Thr Pro Arg Val Thr Gly Gly Gly Ala Met Ala
145                 150                 155

<210> SEQ ID NO 45
<211> LENGTH: 471
<212> TYPE: DNA
<213> ORGANISM: Artificial Sequence
<220> FEATURE:
<223> OTHER INFORMATION: Synthetic

<400> SEQUENCE: 45
ctgctgcaga ccggtatcca cgttcgtgtt tctcagccgt ctctgatcat caaaccgggt   60
aaaatctctc acatcatgct ggacgttgct gaacacccga ccttcacctc tcagtaccgt  120

```
atccagggta aactggctgg tatcctggct cgtaacctgg ttccgatggt tgctaccgtt      180
aaataccagg aattcttctg ggacgctaac gacatctacc gtatcgaatt cgagctccgt      240
cgacaaaaag tttacctgga atctttctgc gaagacgttc cgtctggtaa aaccctgggt      300
tctgacgttg aagaagacct gaccatgacc cgtaacccgc tgaaaatgct gaacatcccg      360
tctatcaacg ttcaccacta cgcttgcacc tctggtgtta tgacccgtgg tcgtctgaaa      420
gctgaaaccg aacgtaaaac cccgcgtgtt accggtggtg gtgctatggc t              471
```

<210> SEQ ID NO 46
<211> LENGTH: 28
<212> TYPE: DNA
<213> ORGANISM: Artificial Sequence
<220> FEATURE:
<223> OTHER INFORMATION: Synthetic

<400> SEQUENCE: 46

```
gcgcggccgc gacgacaagg ccatggct                                          28
```

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47

```
gcctcgaggt tagccataga gatagc                                            26
```

<210> SEQ ID NO 48
<211> LENGTH: 230
<212> TYPE: PRT
<213> ORGANISM: Artificial Sequence
<220> FEATURE:
<223> OTHER INFORMATION: Synthetic

<400> SEQUENCE: 48

```
Asn Gln Arg Ala Leu Tyr His Thr Glu Asn Ala Tyr Val Ser Val Val
1               5                   10                  15

Ser Ser Asp Met Arg Ala Glu Ile Ile Lys Met Met Glu Ser Ala Arg
            20                  25                  30

Pro Glu Ala Leu Ala Ser Arg Tyr Leu Thr Asp Met Thr Ile Glu Glu
        35                  40                  45

Met Ser Arg Leu Ala Ser Thr Thr Ala Lys Ala Met Glu Gln Met Ala
    50                  55                  60

Gly Ser Ser Glu Ser Gly Tyr Ala Ala Asp Gln Lys Ser Thr Gln Asn
65                  70                  75                  80

Ala Ile Asn Gly Ile Thr Asn Lys Val Asn Glu Ile Arg Ala Ser Val
                85                  90                  95

Gly Lys Met Ile Asp Gly Ile Gly Arg Phe Tyr Ile Pro Ile Tyr Arg
            100                 105                 110

Arg Val Asp Gly Lys Trp Met Arg Glu Leu Val Leu Tyr Arg Met Cys
        115                 120                 125

Asn Ile Leu Lys Gly Lys Phe Gln Thr Ala Ala Gln Arg Ala Met Glu
    130                 135                 140

Phe Glu Leu Arg Arg Gln Ile Trp Thr Tyr Asn Ala Glu Leu Leu Val
145                 150                 155                 160

Leu Leu Glu Asn Glu Arg Thr Leu Asp Phe His Asp Ser His Lys Ser
                165                 170                 175
```

Gln Leu Val Trp Met Ala Cys Asn Ser Ala Ala Phe Glu Asp Cys Met
            180                 185                 190

Gly Leu Ile Tyr Asn Arg Met Gly Ala Val Thr Thr Glu Ser Ala Arg
        195                 200                 205

Gln Met Val Gln Ala Met Arg Ala Ile Gly Thr His Pro Ser Ser Ser
    210                 215                 220

Thr Gly Leu Lys Asn Asp
225                 230

<210> SEQ ID NO 49
<211> LENGTH: 690
<212> TYPE: DNA
<213> ORGANISM: Artificial Sequence
<220> FEATURE:
<223> OTHER INFORMATION: Synthetic

<400> SEQUENCE: 49
aaccagcgtg ctctgtacca caccgaaaac gcttacgttt cggttgtaag ctctgacatg        60
cgtgctgaaa tcatcaaaat gatggaatct gctcgtccgg aagctctggc ttctcgttac       120
ctgaccgaca tgaccatcga agaaatgtct cgtctggctt ctaccaccgc taaagctatg       180
gaacagatgg ctggttcttc tgaatctggt tacgctgctg accagaaatc tacccagaac       240
gctatcaacg gtatccacca aaagttaac gaaatccgtg cttctgttgg taaaatgatc       300
gacggtatag gcaggttcta catcccgata taccgtcgtg ttgacggtaa atggatgcgt       360
gaactggttc tgtaccgtat gtgcaacatc ctgaaaggta aattccagac cgctgctcag       420
cgtgctatgg aattcgagct ccgtcgacaa atctggacct acaacgctga actgctggtt       480
ctgctggaaa acgaacgtac cctggacttc cacgactctc acaaatctca gctggtttgg       540
atggcttgca actcggcggc gttcgaagac tgcatgggtc tgatctacaa ccgtatgggt       600
gctgttacca ccgaatctgc tcgtcagatg gttcaggcta tgcgtgctat cggtacccac       660
ccgtcttctt ctaccggtct gaaaaacgac                                        690

<210> SEQ ID NO 50
<211> LENGTH: 28
<212> TYPE: DNA
<213> ORGANISM: Artificial Sequence
<220> FEATURE:
<223> OTHER INFORMATION: Synthetic

<400> SEQUENCE: 50
gcgcggccgc gttagccata gagatagc                                           28

<210> SEQ ID NO 51
<211> LENGTH: 32
<212> TYPE: DNA
<213> ORGANISM: Artificial Sequence
<220> FEATURE:
<223> OTHER INFORMATION: Synthetic

<400> SEQUENCE: 51
gcgtcgacaa gacgacaagg ccatggctat gc                                      32

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
gcctcgaggt tagccataga gatagca                                27

<210> SEQ ID NO 53
<211> LENGTH: 31
<212> TYPE: DNA
<213> ORGANISM: Artificial Sequence
<220> FEATURE:
<223> OTHER INFORMATION: Synthetic

<400> SEQUENCE: 53
gcgcggccgc gacgacaagg ccatggctat g                           31

<210> SEQ ID NO 54
<211> LENGTH: 872
<212> TYPE: PRT
<213> ORGANISM: Artificial Sequence
<220> FEATURE:
<223> OTHER INFORMATION: Synthetic

<400> SEQUENCE: 54

```
Met His His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Met Gln
        35                  40                  45

Ala Glu Gly Arg Gly Thr Gly Gly Ser Thr Gly Asp Ala Asp Gly Pro
    50                  55                  60

Gly Gly Pro Gly Ile Pro Asp Gly Pro Gly Gly Asn Ala Gly Gly Pro
65                  70                  75                  80

Gly Glu Ala Gly Ala Thr Gly Gly Arg Gly Pro Arg Gly Ala Gly Ala
                85                  90                  95

Ala Arg Ala Ser Gly Pro Arg Gly Gly Ala Pro Arg Gly Pro His Gly
            100                 105                 110

Gly Ala Ala Ser Ala Gln Asp Gly Arg Cys Pro Cys Gly Ala Arg Arg
        115                 120                 125

Pro Asp Ser Arg Leu Leu Glu Leu His Ile Thr Met Pro Phe Ser Ser
130                 135                 140

Pro Met Glu Ala Glu Leu Val Arg Arg Ile Leu Ser Arg Asp Ala Ala
145                 150                 155                 160

Pro Leu Pro Arg Pro Gly Ala Val Leu Lys Asp Phe Thr Val Ser Gly
                165                 170                 175

Asn Leu Leu Phe Met Ser Val Arg Asp Gln Asp Arg Glu Gly Ala Gly
            180                 185                 190

Arg Met Arg Val Val Gly Trp Gly Leu Gly Ser Ala Ser Pro Glu Gly
        195                 200                 205

Gln Lys Ala Arg Asp Leu Arg Thr Pro Lys His Lys Val Ser Glu Gln
    210                 215                 220

Arg Pro Gly Thr Pro Gly Pro Pro Pro Glu Gly Ala Gln Gly Asp
225                 230                 235                 240

Gly Cys Arg Gly Val Ala Phe Asn Val Met Phe Ser Ala Pro His Ile
                245                 250                 255

Pro Leu Glu Gln Arg Ser Gln His Cys Lys Pro Glu Glu Gly Leu Glu
            260                 265                 270

Ala Arg Gly Glu Ala Leu Gly Leu Val Gly Ala Gln Ala Pro Ala Thr
        275                 280                 285
```

```
Glu Gln Glu Ala Ala Ser Ser Ser Thr Leu Val Glu Val Thr
290                 295                 300

Leu Gly Glu Val Pro Ala Ala Glu Ser Pro Asp Pro Gln Ser Pro
305                 310                 315                 320

Gln Gly Ala Ser Ser Leu Pro Thr Thr Met Asn Tyr Pro Leu Trp Ser
                325                 330                 335

Gln Ser Tyr Glu Asp Ser Ser Asn Gln Glu Glu Gly Pro Ser Thr
            340                 345                 350

Phe Pro Asp Leu Glu Ser Glu Phe Gln Ala Ala Leu Ser Arg Lys Val
        355                 360                 365

Ala Glu Leu Val His Phe Leu Leu Lys Tyr Arg Ala Arg Glu Pro
370                 375                 380

Val Thr Lys Ala Glu Met Leu Gly Ser Val Val Gly Asn Trp Gln Tyr
385                 390                 395                 400

Phe Phe Pro Val Ile Phe Ser Lys Ala Ser Ser Ser Leu Gln Leu Val
                405                 410                 415

Phe Gly Ile Glu Leu Met Glu Val Asp Pro Ile Gly His Leu Tyr Ile
            420                 425                 430

Phe Ala Thr Cys Leu Gly Leu Ser Tyr Asp Gly Leu Leu Gly Asp Asn
                435                 440                 445

Gln Ile Met Pro Lys Ala Gly Leu Leu Ile Ile Val Leu Ala Ile Ile
450                 455                 460

Ala Arg Glu Gly Asp Cys Ala Pro Glu Glu Lys Ile Trp Glu Glu Leu
465                 470                 475                 480

Ser Val Leu Glu Val Phe Glu Gly Arg Glu Asp Ser Ile Leu Gly Asp
                485                 490                 495

Pro Lys Lys Leu Leu Thr Gln His Phe Val Gln Glu Asn Tyr Leu Glu
        500                 505                 510

Tyr Arg Gln Val Pro Gly Ser Asp Pro Ala Cys Tyr Glu Phe Leu Trp
        515                 520                 525

Gly Pro Arg Ala Leu Val Glu Thr Ser Tyr Val Lys Val Leu His His
530                 535                 540

Met Val Lys Ile Ser Gly Gly Pro His Ile Ser Tyr Pro Pro Leu His
545                 550                 555                 560

Glu Trp Val Leu Arg Glu Gly Glu Ala Gln Ala Glu Gly Arg Gly
                565                 570                 575

Thr Gly Gly Ser Thr Gly Asp Ala Asp Gly Pro Gly Pro Gly Ile
            580                 585                 590

Pro Asp Gly Pro Gly Gly Asn Ala Gly Gly Pro Gly Glu Ala Gly Ala
                595                 600                 605

Thr Gly Gly Arg Gly Pro Arg Gly Ala Gly Ala Ala Arg Ala Ser Gly
            610                 615                 620

Pro Gly Gly Gly Ala Pro Arg Gly Pro His Gly Gly Ala Ala Ser Gly
625                 630                 635                 640

Leu Asn Gly Cys Cys Arg Cys Gly Ala Arg Gly Pro Glu Ser Arg Leu
                645                 650                 655

Leu Glu Phe Tyr Leu Ala Met Pro Phe Ala Thr Pro Met Glu Ala Glu
            660                 665                 670

Leu Ala Arg Arg Ser Leu Ala Gln Asp Ala Pro Pro Leu Pro Val Pro
        675                 680                 685

Gly Val Leu Leu Lys Glu Phe Thr Val Ser Gly Asn Ile Leu Thr Ile
690                 695                 700
```

```
Arg Leu Thr Ala Ala Asp His Arg Gln Leu Gln Leu Ser Ile Ser Ser
705                 710                 715                 720

Cys Leu Gln Gln Leu Ser Leu Leu Met Trp Ile Thr Gln Cys Phe Leu
            725                 730                 735

Pro Val Phe Leu Ala Gln Pro Pro Ser Gly Gln Arg Arg Ile Lys Leu
        740                 745                 750

Lys Phe Gly Val Phe Phe Thr Val Leu Leu Ser Ser Ala Tyr Ala His
    755                 760                 765

Gly Thr Pro Gln Asn Ile Thr Asp Leu Cys Ala Glu Tyr His Asn Thr
    770                 775                 780

Gln Ile His Thr Leu Asn Asp Lys Ile Phe Ser Tyr Thr Glu Ser Leu
785                 790                 795                 800

Ala Gly Lys Arg Glu Met Ala Ile Ile Thr Phe Lys Asn Gly Ala Thr
                805                 810                 815

Phe Gln Val Glu Val Pro Gly Ser Gln His Ile Asp Ser Gln Lys Lys
            820                 825                 830

Ala Ile Glu Arg Met Lys Asp Thr Leu Arg Ile Ala Tyr Leu Thr Glu
        835                 840                 845

Ala Lys Val Glu Lys Leu Cys Val Trp Asn Asn Lys Thr Pro His Ala
    850                 855                 860

Ile Ala Ala Ile Ser Met Ala Asn
865                 870

<210> SEQ ID NO 55
<211> LENGTH: 1043
<212> TYPE: PRT
<213> ORGANISM: Artificial Sequence
<220> FEATURE:
<223> OTHER INFORMATION: Synthetic

<400> SEQUENCE: 55

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
        35                  40                  45

Gly Ser Asn Gln Arg Ala Leu Tyr His Thr Glu Asn Ala Tyr Val Ser
    50                  55                  60

Val Val Ser Ser Asp Met Arg Ala Glu Ile Ile Lys Met Met Glu Ser
65                  70                  75                  80

Ala Arg Pro Glu Ala Leu Ala Ser Arg Tyr Leu Thr Asp Met Thr Ile
                85                  90                  95

Glu Glu Met Ser Arg Leu Ala Ser Thr Thr Ala Lys Ala Met Glu Gln
            100                 105                 110

Met Ala Gly Ser Ser Glu Ser Gly Tyr Ala Ala Asp Gln Lys Ser Thr
        115                 120                 125

Gln Asn Ala Ile Asn Gly Ile Thr Asn Lys Val Asn Glu Ile Arg Ala
    130                 135                 140

Ser Val Gly Lys Met Ile Asp Gly Ile Gly Arg Phe Tyr Ile Pro Ile
145                 150                 155                 160

Tyr Arg Arg Val Asp Gly Lys Trp Met Arg Glu Leu Val Leu Tyr Arg
                165                 170                 175

Met Cys Asn Ile Leu Lys Gly Lys Phe Gln Thr Ala Ala Gln Arg Ala
            180                 185                 190
```

-continued

```
Met Glu Phe Glu Leu Arg Arg Gln Asp Asp Lys Ala Met Ala Met Gln
            195                 200                 205

Ala Glu Gly Arg Gly Thr Gly Gly Ser Thr Gly Asp Ala Asp Gly Pro
210                 215                 220

Gly Gly Pro Gly Ile Pro Asp Gly Pro Gly Gly Asn Ala Gly Gly Pro
225                 230                 235                 240

Gly Glu Ala Gly Ala Thr Gly Gly Arg Gly Pro Arg Gly Ala Gly Ala
                245                 250                 255

Ala Arg Ala Ser Gly Pro Arg Gly Gly Ala Pro Arg Gly Pro His Gly
                260                 265                 270

Gly Ala Ala Ser Ala Gln Asp Gly Arg Cys Pro Cys Gly Ala Arg Arg
            275                 280                 285

Pro Asp Ser Arg Leu Leu Glu Leu His Ile Thr Met Pro Phe Ser Ser
            290                 295                 300

Pro Met Glu Ala Glu Leu Val Arg Arg Ile Leu Ser Arg Asp Ala Ala
305                 310                 315                 320

Pro Leu Pro Arg Pro Gly Ala Val Leu Lys Asp Phe Thr Val Ser Gly
                325                 330                 335

Asn Leu Leu Phe Met Ser Val Arg Asp Gln Asp Arg Glu Gly Ala Gly
                340                 345                 350

Arg Met Arg Val Val Gly Trp Gly Leu Gly Ser Ala Ser Pro Glu Gly
            355                 360                 365

Gln Lys Ala Arg Asp Leu Arg Thr Pro Lys His Lys Val Ser Glu Gln
            370                 375                 380

Arg Pro Gly Thr Pro Gly Pro Pro Pro Glu Gly Ala Gln Gly Asp
385                 390                 395                 400

Gly Cys Arg Gly Val Ala Phe Asn Val Met Phe Ser Ala Pro His Ile
                405                 410                 415

Pro Leu Glu Gln Arg Ser Gln His Cys Lys Pro Glu Glu Gly Leu Glu
                420                 425                 430

Ala Arg Gly Glu Ala Leu Gly Leu Val Gly Ala Gln Ala Pro Ala Thr
            435                 440                 445

Glu Glu Gln Glu Ala Ala Ser Ser Ser Thr Leu Val Glu Val Thr
450                 455                 460

Leu Gly Glu Val Pro Ala Ala Glu Ser Pro Asp Pro Pro Gln Ser Pro
465                 470                 475                 480

Gln Gly Ala Ser Ser Leu Pro Thr Thr Met Asn Tyr Pro Leu Trp Ser
                485                 490                 495

Gln Ser Tyr Glu Asp Ser Ser Asn Gln Glu Glu Glu Gly Pro Ser Thr
                500                 505                 510

Phe Pro Asp Leu Glu Ser Glu Phe Gln Ala Ala Leu Ser Arg Lys Val
            515                 520                 525

Ala Glu Leu Val His Phe Leu Leu Leu Lys Tyr Arg Ala Arg Glu Pro
            530                 535                 540

Val Thr Lys Ala Glu Met Leu Gly Ser Val Val Gly Asn Trp Gln Tyr
545                 550                 555                 560

Phe Phe Pro Val Ile Phe Ser Lys Ala Ser Ser Ser Leu Gln Leu Val
                565                 570                 575

Phe Gly Ile Glu Leu Met Glu Val Asp Pro Ile Gly His Leu Tyr Ile
                580                 585                 590

Phe Ala Thr Cys Leu Gly Leu Ser Tyr Asp Gly Leu Leu Gly Asp Asn
            595                 600                 605

Gln Ile Met Pro Lys Ala Gly Leu Leu Ile Ile Val Leu Ala Ile Ile
```

```
              610                 615                 620
Ala Arg Glu Gly Asp Cys Ala Pro Glu Lys Ile Trp Glu Leu
625                 630                 635                 640

Ser Val Leu Glu Val Phe Gly Arg Glu Asp Ser Ile Leu Gly Asp
                645                 650                 655

Pro Lys Lys Leu Leu Thr Gln His Phe Val Gln Glu Asn Tyr Leu Glu
                660                 665                 670

Tyr Arg Gln Val Pro Gly Ser Asp Pro Ala Cys Tyr Glu Phe Leu Trp
                675                 680                 685

Gly Pro Arg Ala Leu Val Glu Thr Ser Tyr Val Lys Val Leu His His
690                 695                 700

Met Val Lys Ile Ser Gly Gly Pro His Ile Ser Tyr Pro Pro Leu His
705                 710                 715                 720

Glu Trp Val Leu Arg Glu Gly Glu Ala Gln Ala Glu Gly Arg Gly
                725                 730                 735

Thr Gly Gly Ser Thr Gly Asp Ala Asp Gly Pro Gly Gly Pro Gly Ile
                740                 745                 750

Pro Asp Gly Pro Gly Gly Asn Ala Gly Gly Pro Gly Glu Ala Gly Ala
                755                 760                 765

Thr Gly Gly Arg Gly Pro Arg Gly Ala Gly Ala Ala Arg Ala Ser Gly
770                 775                 780

Pro Gly Gly Gly Ala Pro Arg Gly Pro His Gly Gly Ala Ala Ser Gly
785                 790                 795                 800

Leu Asn Gly Cys Cys Arg Cys Gly Ala Arg Gly Pro Glu Ser Arg Leu
                805                 810                 815

Leu Glu Phe Tyr Leu Ala Met Pro Phe Ala Thr Pro Met Glu Ala Glu
                820                 825                 830

Leu Ala Arg Arg Ser Leu Ala Gln Asp Ala Pro Pro Leu Pro Val Pro
                835                 840                 845

Gly Val Leu Leu Lys Glu Phe Thr Val Ser Gly Asn Ile Leu Thr Ile
850                 855                 860

Arg Leu Thr Ala Ala Asp His Arg Gln Leu Gln Leu Ser Ile Ser Ser
865                 870                 875                 880

Cys Leu Gln Gln Leu Ser Leu Leu Met Trp Ile Thr Gln Cys Phe Leu
                885                 890                 895

Pro Val Phe Leu Ala Gln Pro Pro Ser Gly Gln Arg Arg Ile Lys Leu
                900                 905                 910

Lys Phe Gly Val Phe Phe Thr Val Leu Leu Ser Ser Ala Tyr Ala His
                915                 920                 925

Gly Thr Pro Gln Asn Ile Thr Asp Leu Cys Ala Glu Tyr His Asn Thr
930                 935                 940

Gln Ile His Thr Leu Asn Asp Lys Ile Phe Ser Tyr Thr Glu Ser Leu
945                 950                 955                 960

Ala Gly Lys Arg Glu Met Ala Ile Ile Thr Phe Lys Asn Gly Ala Thr
                965                 970                 975

Phe Gln Val Glu Val Pro Gly Ser Gln His Ile Asp Ser Gln Lys Lys
                980                 985                 990

Ala Ile Glu Arg Met Lys Asp Thr  Leu Arg Ile Ala Tyr Leu Thr Glu
                995                 1000                1005

Ala Lys  Val Glu Lys Leu Cys  Val Trp Asn Asn Lys  Thr Pro His
    1010                1015                1020

Ala Ile  Ala Ala Ile Ser Met  Ala Asn Ala Ala Ala  Leu Glu His
    1025                1030                1035
```

His His His His His
               1040

<210> SEQ ID NO 56
<211> LENGTH: 1125
<212> TYPE: PRT
<213> ORGANISM: Artificial Sequence
<220> FEATURE:
<223> OTHER INFORMATION: Synthetic

<400> SEQUENCE: 56

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Asn Gln Arg Ala Leu Tyr His Thr Glu Asn Ala Tyr Val Ser
    50                  55                  60

Val Val Ser Ser Asp Met Arg Ala Glu Ile Ile Lys Met Met Glu Ser
65                  70                  75                  80

Ala Arg Pro Glu Ala Leu Ala Ser Arg Tyr Leu Thr Asp Met Thr Ile
                85                  90                  95

Glu Glu Met Ser Arg Leu Ala Ser Thr Thr Ala Lys Ala Met Glu Gln
            100                 105                 110

Met Ala Gly Ser Ser Glu Ser Gly Tyr Ala Ala Asp Gln Lys Ser Thr
        115                 120                 125

Gln Asn Ala Ile Asn Gly Ile Thr Asn Lys Val Asn Glu Ile Arg Ala
    130                 135                 140

Ser Val Gly Lys Met Ile Asp Gly Ile Gly Arg Phe Tyr Ile Pro Ile
145                 150                 155                 160

Tyr Arg Arg Val Asp Gly Lys Trp Met Arg Glu Leu Val Leu Tyr Arg
                165                 170                 175

Met Cys Asn Ile Leu Lys Gly Lys Phe Gln Thr Ala Ala Gln Arg Ala
            180                 185                 190

Met Glu Phe Glu Leu Arg Arg Gln Ile Trp Thr Tyr Asn Ala Glu Leu
        195                 200                 205

Leu Val Leu Leu Glu Asn Glu Arg Thr Leu Asp Phe His Asp Ser His
    210                 215                 220

Lys Ser Gln Leu Val Trp Met Ala Cys Asn Ser Ala Ala Phe Glu Asp
225                 230                 235                 240

Cys Met Gly Leu Ile Tyr Asn Arg Met Gly Ala Val Thr Thr Glu Ser
                245                 250                 255

Ala Arg Gln Met Val Gln Ala Met Arg Ala Ile Gly Thr His Pro Ser
            260                 265                 270

Ser Ser Thr Gly Leu Lys Asn Asp Gln Ala Cys Gly Arg Asp Asp Lys
        275                 280                 285

Ala Met Ala Met Gln Ala Glu Gly Arg Gly Thr Gly Gly Ser Thr Gly
    290                 295                 300

Asp Ala Asp Gly Pro Gly Gly Pro Gly Ile Pro Asp Gly Pro Gly Gly
305                 310                 315                 320

Asn Ala Gly Gly Pro Gly Glu Ala Gly Ala Thr Gly Gly Arg Gly Pro
                325                 330                 335

Arg Gly Ala Gly Ala Ala Arg Ala Ser Gly Pro Arg Gly Ala Pro
            340                 345                 350

```
Arg Gly Pro His Gly Gly Ala Ala Ser Ala Gln Asp Gly Arg Cys Pro
            355                 360                 365
Cys Gly Ala Arg Arg Pro Asp Ser Arg Leu Leu Glu Leu His Ile Thr
        370                 375                 380
Met Pro Phe Ser Ser Pro Met Glu Ala Glu Leu Val Arg Arg Ile Leu
385                 390                 395                 400
Ser Arg Asp Ala Ala Pro Leu Pro Arg Pro Gly Ala Val Leu Lys Asp
                405                 410                 415
Phe Thr Val Ser Gly Asn Leu Leu Phe Met Ser Val Arg Asp Gln Asp
            420                 425                 430
Arg Glu Gly Ala Gly Arg Met Arg Val Val Gly Trp Gly Leu Gly Ser
            435                 440                 445
Ala Ser Pro Glu Gly Gln Lys Ala Arg Asp Leu Arg Thr Pro Lys His
        450                 455                 460
Lys Val Ser Glu Gln Arg Pro Gly Thr Pro Gly Pro Pro Pro Glu
465                 470                 475                 480
Gly Ala Gln Gly Asp Gly Cys Arg Gly Val Ala Phe Asn Val Met Phe
                485                 490                 495
Ser Ala Pro His Ile Pro Leu Glu Gln Arg Ser Gln His Cys Lys Pro
            500                 505                 510
Glu Glu Gly Leu Glu Ala Arg Gly Glu Ala Leu Gly Leu Val Gly Ala
        515                 520                 525
Gln Ala Pro Ala Thr Glu Glu Gln Glu Ala Ala Ser Ser Ser Ser Thr
    530                 535                 540
Leu Val Glu Val Thr Leu Gly Glu Val Pro Ala Ala Glu Ser Pro Asp
545                 550                 555                 560
Pro Pro Gln Ser Pro Gln Gly Ala Ser Ser Leu Pro Thr Thr Met Asn
                565                 570                 575
Tyr Pro Leu Trp Ser Gln Ser Tyr Glu Asp Ser Ser Asn Gln Glu Glu
            580                 585                 590
Glu Gly Pro Ser Thr Phe Pro Asp Leu Glu Ser Glu Phe Gln Ala Ala
        595                 600                 605
Leu Ser Arg Lys Val Ala Glu Leu Val His Phe Leu Leu Leu Lys Tyr
    610                 615                 620
Arg Ala Arg Glu Pro Val Thr Lys Ala Glu Met Leu Gly Ser Val Val
625                 630                 635                 640
Gly Asn Trp Gln Tyr Phe Phe Pro Val Ile Phe Ser Lys Ala Ser Ser
                645                 650                 655
Ser Leu Gln Leu Val Phe Gly Ile Glu Leu Met Glu Val Asp Pro Ile
            660                 665                 670
Gly His Leu Tyr Ile Phe Ala Thr Cys Leu Gly Leu Ser Tyr Asp Gly
        675                 680                 685
Leu Leu Gly Asp Asn Gln Ile Met Pro Lys Ala Gly Leu Leu Ile Ile
    690                 695                 700
Val Leu Ala Ile Ile Ala Arg Glu Gly Asp Cys Ala Pro Glu Glu Lys
705                 710                 715                 720
Ile Trp Glu Glu Leu Ser Val Leu Glu Val Phe Glu Gly Arg Glu Asp
                725                 730                 735
Ser Ile Leu Gly Asp Pro Lys Lys Leu Leu Thr Gln His Phe Val Gln
            740                 745                 750
Glu Asn Tyr Leu Glu Tyr Arg Gln Val Pro Gly Ser Asp Pro Ala Cys
        755                 760                 765
```

Tyr Glu Phe Leu Trp Gly Pro Arg Ala Leu Val Glu Thr Ser Tyr Val
770                 775                 780

Lys Val Leu His His Met Val Lys Ile Ser Gly Gly Pro His Ile Ser
785                 790                 795                 800

Tyr Pro Pro Leu His Glu Trp Val Leu Arg Glu Gly Glu Ala Gln
            805                 810                 815

Ala Glu Gly Arg Gly Thr Gly Ser Thr Gly Asp Ala Asp Gly Pro
            820                 825                 830

Gly Gly Pro Gly Ile Pro Asp Gly Pro Gly Gly Asn Ala Gly Gly Pro
            835                 840                 845

Gly Glu Ala Gly Ala Thr Gly Gly Arg Gly Pro Arg Gly Ala Gly Ala
850                 855                 860

Ala Arg Ala Ser Gly Pro Gly Gly Ala Pro Arg Gly Pro His Gly
865                 870                 875                 880

Gly Ala Ala Ser Gly Leu Asn Gly Cys Cys Arg Cys Gly Ala Arg Gly
                    885                 890                 895

Pro Glu Ser Arg Leu Leu Glu Phe Tyr Leu Ala Met Pro Phe Ala Thr
            900                 905                 910

Pro Met Glu Ala Glu Leu Ala Arg Arg Ser Leu Ala Gln Asp Ala Pro
            915                 920                 925

Pro Leu Pro Val Pro Gly Val Leu Lys Glu Phe Thr Val Ser Gly
930                 935                 940

Asn Ile Leu Thr Ile Arg Leu Thr Ala Ala Asp His Arg Gln Leu Gln
945                 950                 955                 960

Leu Ser Ile Ser Ser Cys Leu Gln Gln Leu Ser Leu Met Trp Ile
                    965                 970                 975

Thr Gln Cys Phe Leu Pro Val Phe Leu Ala Gln Pro Pro Ser Gly Gln
            980                 985                 990

Arg Arg Ile Lys Leu Lys Phe Gly Val Phe Phe Thr Val Leu Leu Ser
            995                 1000                1005

Ser Ala Tyr Ala His Gly Thr Pro Gln Asn Ile Thr Asp Leu Cys
    1010                1015                1020

Ala Glu Tyr His Asn Thr Gln Ile His Thr Leu Asn Asp Lys Ile
    1025                1030                1035

Phe Ser Tyr Thr Glu Ser Leu Ala Gly Lys Arg Glu Met Ala Ile
    1040                1045                1050

Ile Thr Phe Lys Asn Gly Ala Thr Phe Gln Val Glu Val Pro Gly
    1055                1060                1065

Ser Gln His Ile Asp Ser Gln Lys Lys Ala Ile Glu Arg Met Lys
    1070                1075                1080

Asp Thr Leu Arg Ile Ala Tyr Leu Thr Glu Ala Lys Val Glu Lys
    1085                1090                1095

Leu Cys Val Trp Asn Asn Lys Thr Pro His Ala Ile Ala Ala Ile
    1100                1105                1110

Ser Met Ala Asn Leu Glu His His His His His
    1115                1120                1125

<210> SEQ ID NO 57
<211> LENGTH: 975
<212> TYPE: PRT
<213> ORGANISM: Artificial Sequence
<220> FEATURE:
<223> OTHER INFORMATION: Synthetic

<400> SEQUENCE: 57

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Leu Leu Gln Thr Gly Ile His Val Arg Val Ser Gln Pro Ser
50                      55                  60

Leu Ile Ile Lys Pro Gly Lys Ile Ser His Ile Met Leu Asp Val Ala
65                  70                  75                  80

Glu His Pro Thr Phe Thr Ser Gln Tyr Arg Ile Gln Gly Lys Leu Ala
                85                  90                  95

Gly Ile Leu Ala Arg Asn Leu Val Pro Met Val Ala Thr Val Lys Tyr
            100                 105                 110

Gln Glu Phe Phe Trp Asp Ala Asn Asp Ile Tyr Arg Ile Glu Phe Glu
            115                 120                 125

Leu Arg Arg Gln Asp Asp Lys Ala Met Ala Met Gln Ala Glu Gly Arg
    130                 135                 140

Gly Thr Gly Gly Ser Thr Gly Asp Ala Asp Gly Pro Gly Pro Gly
145                 150                 155                 160

Ile Pro Asp Gly Pro Gly Asn Ala Gly Gly Pro Gly Glu Ala Gly
            165                 170                 175

Ala Thr Gly Gly Arg Gly Pro Arg Gly Ala Gly Ala Ala Arg Ala Ser
            180                 185                 190

Gly Pro Arg Gly Ala Pro Arg Gly Pro His Gly Ala Ala Ser
    195                 200                 205

Ala Gln Asp Gly Arg Cys Pro Cys Gly Ala Arg Arg Pro Asp Ser Arg
    210                 215                 220

Leu Leu Glu Leu His Ile Thr Met Pro Phe Ser Ser Pro Met Glu Ala
225                 230                 235                 240

Glu Leu Val Arg Arg Ile Leu Ser Arg Asp Ala Ala Pro Leu Pro Arg
            245                 250                 255

Pro Gly Ala Val Leu Lys Asp Phe Thr Val Ser Gly Asn Leu Leu Phe
            260                 265                 270

Met Ser Val Arg Asp Gln Asp Arg Glu Gly Ala Gly Arg Met Arg Val
    275                 280                 285

Val Gly Trp Gly Leu Gly Ser Ala Ser Pro Glu Gly Gln Lys Ala Arg
    290                 295                 300

Asp Leu Arg Thr Pro Lys His Lys Val Ser Glu Gln Arg Pro Gly Thr
305                 310                 315                 320

Pro Gly Pro Pro Pro Glu Gly Ala Gln Gly Asp Gly Cys Arg Gly
                325                 330                 335

Val Ala Phe Asn Val Met Phe Ser Ala Pro His Ile Pro Leu Glu Gln
            340                 345                 350

Arg Ser Gln His Cys Lys Pro Glu Glu Gly Leu Glu Ala Arg Gly Glu
            355                 360                 365

Ala Leu Gly Leu Val Gly Ala Gln Ala Pro Ala Thr Glu Glu Gln Glu
    370                 375                 380

Ala Ala Ser Ser Ser Ser Thr Leu Val Glu Val Thr Leu Gly Glu Val
385                 390                 395                 400

Pro Ala Ala Glu Ser Pro Asp Pro Pro Gln Ser Pro Gln Gly Ala Ser
            405                 410                 415

Ser Leu Pro Thr Thr Met Asn Tyr Pro Leu Trp Ser Gln Ser Tyr Glu
```

-continued

```
            420                 425                 430
Asp Ser Ser Asn Gln Glu Glu Gly Pro Ser Thr Phe Pro Asp Leu
        435                 440                 445
Glu Ser Glu Phe Gln Ala Ala Leu Ser Arg Lys Val Ala Glu Leu Val
    450                 455                 460
His Phe Leu Leu Leu Lys Tyr Arg Ala Arg Glu Pro Val Thr Lys Ala
465                 470                 475                 480
Glu Met Leu Gly Ser Val Val Gly Asn Trp Gln Tyr Phe Phe Pro Val
                485                 490                 495
Ile Phe Ser Lys Ala Ser Ser Leu Gln Leu Val Phe Gly Ile Glu
            500                 505                 510
Leu Met Glu Val Asp Pro Ile Gly His Leu Tyr Ile Phe Ala Thr Cys
        515                 520                 525
Leu Gly Leu Ser Tyr Asp Gly Leu Leu Gly Asp Asn Gln Ile Met Pro
    530                 535                 540
Lys Ala Gly Leu Leu Ile Ile Val Leu Ala Ile Ile Ala Arg Glu Gly
545                 550                 555                 560
Asp Cys Ala Pro Glu Glu Lys Ile Trp Glu Glu Leu Ser Val Leu Glu
                565                 570                 575
Val Phe Glu Gly Arg Glu Asp Ser Ile Leu Gly Asp Pro Lys Lys Leu
            580                 585                 590
Leu Thr Gln His Phe Val Gln Glu Asn Tyr Leu Glu Tyr Arg Gln Val
        595                 600                 605
Pro Gly Ser Asp Pro Ala Cys Tyr Glu Phe Leu Trp Gly Pro Arg Ala
    610                 615                 620
Leu Val Glu Thr Ser Tyr Val Lys Val Leu His His Met Val Lys Ile
625                 630                 635                 640
Ser Gly Gly Pro His Ile Ser Tyr Pro Pro Leu His Glu Trp Val Leu
                645                 650                 655
Arg Glu Gly Glu Glu Ala Gln Ala Glu Gly Arg Gly Thr Gly Gly Ser
            660                 665                 670
Thr Gly Asp Ala Asp Gly Pro Gly Pro Gly Ile Pro Asp Gly Pro
        675                 680                 685
Gly Gly Asn Ala Gly Gly Pro Gly Glu Ala Gly Ala Thr Gly Gly Arg
    690                 695                 700
Gly Pro Arg Gly Ala Gly Ala Ala Arg Ala Ser Gly Pro Gly Gly Gly
705                 710                 715                 720
Ala Pro Arg Gly Pro His Gly Gly Ala Ala Ser Gly Leu Asn Gly Cys
                725                 730                 735
Cys Arg Cys Gly Ala Arg Gly Pro Glu Ser Arg Leu Leu Glu Phe Tyr
            740                 745                 750
Leu Ala Met Pro Phe Ala Thr Pro Met Glu Ala Glu Leu Ala Arg Arg
        755                 760                 765
Ser Leu Ala Gln Asp Ala Pro Pro Leu Pro Val Pro Gly Val Leu Leu
    770                 775                 780
Lys Glu Phe Thr Val Ser Gly Asn Ile Leu Thr Ile Arg Leu Thr Ala
785                 790                 795                 800
Ala Asp His Arg Gln Leu Gln Leu Ser Ile Ser Ser Cys Leu Gln Gln
                805                 810                 815
Leu Ser Leu Leu Met Trp Ile Thr Gln Cys Phe Leu Pro Val Phe Leu
            820                 825                 830
Ala Gln Pro Pro Ser Gly Gln Arg Arg Ile Lys Leu Lys Phe Gly Val
        835                 840                 845
```

```
Phe Phe Thr Val Leu Leu Ser Ser Ala Tyr Ala His Gly Thr Pro Gln
    850                 855                 860

Asn Ile Thr Asp Leu Cys Ala Glu Tyr His Asn Thr Gln Ile His Thr
865                 870                 875                 880

Leu Asn Asp Lys Ile Phe Ser Tyr Thr Glu Ser Leu Ala Gly Lys Arg
                885                 890                 895

Glu Met Ala Ile Ile Thr Phe Lys Asn Gly Ala Thr Phe Gln Val Glu
                900                 905                 910

Val Pro Gly Ser Gln His Ile Asp Ser Gln Lys Lys Ala Ile Glu Arg
            915                 920                 925

Met Lys Asp Thr Leu Arg Ile Ala Tyr Leu Thr Glu Ala Lys Val Glu
        930                 935                 940

Lys Leu Cys Val Trp Asn Asn Lys Thr Pro His Ala Ile Ala Ala Ile
945                 950                 955                 960

Ser Met Ala Asn Ala Ala Ala Leu Glu His His His His His His
                965                 970                 975
```

```
<210> SEQ ID NO 58
<211> LENGTH: 1052
<212> TYPE: PRT
<213> ORGANISM: Artificial Sequence
<220> FEATURE:
<223> OTHER INFORMATION: Synthetic

<400> SEQUENCE: 58

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
            35                  40                  45

Gly Ser Leu Leu Gln Thr Gly Ile His Val Arg Val Ser Gln Pro Ser
50                  55                  60

Leu Ile Ile Lys Pro Gly Lys Ile Ser His Ile Met Leu Asp Val Ala
65                  70                  75                  80

Glu His Pro Thr Phe Thr Ser Gln Tyr Arg Ile Gln Gly Lys Leu Ala
                85                  90                  95

Gly Ile Leu Ala Arg Asn Leu Val Pro Met Val Ala Thr Val Lys Tyr
                100                 105                 110

Gln Glu Phe Phe Trp Asp Ala Asn Asp Ile Tyr Arg Ile Glu Phe Glu
            115                 120                 125

Leu Arg Arg Gln Lys Val Tyr Leu Glu Ser Phe Cys Glu Asp Val Pro
130                 135                 140

Ser Gly Lys Thr Leu Gly Ser Asp Val Glu Glu Asp Leu Thr Met Thr
145                 150                 155                 160

Arg Asn Pro Leu Lys Met Leu Asn Ile Pro Ser Ile Asn Val His His
                165                 170                 175

Tyr Ala Cys Thr Ser Gly Val Met Thr Arg Gly Arg Leu Lys Ala Glu
                180                 185                 190

Thr Glu Arg Lys Thr Pro Arg Val Thr Gly Gly Ala Met Ala Gln
            195                 200                 205

Ala Cys Gly Arg Asp Asp Lys Ala Met Ala Met Gln Ala Glu Gly Arg
    210                 215                 220

Gly Thr Gly Gly Ser Thr Gly Asp Ala Asp Gly Pro Gly Gly Pro Gly
225                 230                 235                 240
```

```
Ile Pro Asp Gly Pro Gly Asn Ala Gly Pro Gly Glu Ala Gly
            245                 250                 255

Ala Thr Gly Gly Arg Gly Pro Arg Gly Ala Gly Ala Arg Ala Ser
            260                 265                 270

Gly Pro Arg Gly Gly Ala Pro Arg Gly Pro His Gly Gly Ala Ala Ser
            275                 280                 285

Ala Gln Asp Gly Arg Cys Pro Cys Gly Ala Arg Arg Pro Asp Ser Arg
        290                 295                 300

Leu Leu Glu Leu His Ile Thr Met Pro Phe Ser Ser Pro Met Glu Ala
305                 310                 315                 320

Glu Leu Val Arg Arg Ile Leu Ser Arg Asp Ala Ala Pro Leu Pro Arg
            325                 330                 335

Pro Gly Ala Val Leu Lys Asp Phe Thr Val Ser Gly Asn Leu Leu Phe
            340                 345                 350

Met Ser Val Arg Asp Gln Asp Arg Glu Gly Ala Gly Arg Met Arg Val
            355                 360                 365

Val Gly Trp Gly Leu Gly Ser Ala Ser Pro Glu Gly Gln Lys Ala Arg
            370                 375                 380

Asp Leu Arg Thr Pro Lys His Lys Val Ser Glu Gln Arg Pro Gly Thr
385                 390                 395                 400

Pro Gly Pro Pro Pro Glu Gly Ala Gln Gly Asp Gly Cys Arg Gly
            405                 410                 415

Val Ala Phe Asn Val Met Phe Ser Ala Pro His Ile Pro Leu Glu Gln
            420                 425                 430

Arg Ser Gln His Cys Lys Pro Glu Gly Leu Glu Ala Arg Gly Glu
            435                 440                 445

Ala Leu Gly Leu Val Gly Ala Gln Ala Pro Ala Thr Glu Glu Gln Glu
            450                 455                 460

Ala Ala Ser Ser Ser Thr Leu Val Glu Val Thr Leu Gly Glu Val
465                 470                 475                 480

Pro Ala Ala Glu Ser Pro Asp Pro Pro Gln Ser Pro Gln Gly Ala Ser
            485                 490                 495

Ser Leu Pro Thr Thr Met Asn Tyr Pro Leu Trp Ser Gln Ser Tyr Glu
            500                 505                 510

Asp Ser Ser Asn Gln Glu Glu Glu Gly Pro Ser Thr Phe Pro Asp Leu
            515                 520                 525

Glu Ser Glu Phe Gln Ala Ala Leu Ser Arg Lys Val Ala Glu Leu Val
530                 535                 540

His Phe Leu Leu Leu Lys Tyr Arg Ala Arg Glu Pro Val Thr Lys Ala
545                 550                 555                 560

Glu Met Leu Gly Ser Val Val Gly Asn Trp Gln Tyr Phe Phe Pro Val
            565                 570                 575

Ile Phe Ser Lys Ala Ser Ser Ser Leu Gln Leu Val Phe Gly Ile Glu
            580                 585                 590

Leu Met Glu Val Asp Pro Ile Gly His Leu Tyr Ile Phe Ala Thr Cys
            595                 600                 605

Leu Gly Leu Ser Tyr Asp Gly Leu Leu Gly Asp Asn Gln Ile Met Pro
            610                 615                 620

Lys Ala Gly Leu Leu Ile Ile Val Leu Ala Ile Ile Ala Arg Glu Gly
625                 630                 635                 640

Asp Cys Ala Pro Glu Glu Lys Ile Trp Glu Glu Leu Ser Val Leu Glu
            645                 650                 655
```

Val Phe Glu Gly Arg Glu Asp Ser Ile Leu Gly Asp Pro Lys Lys Leu
            660                 665                 670

Leu Thr Gln His Phe Val Gln Glu Asn Tyr Leu Glu Tyr Arg Gln Val
            675                 680                 685

Pro Gly Ser Asp Pro Ala Cys Tyr Glu Phe Leu Trp Gly Pro Arg Ala
            690                 695                 700

Leu Val Glu Thr Ser Tyr Val Lys Val Leu His His Met Val Lys Ile
705                 710                 715                 720

Ser Gly Gly Pro His Ile Ser Tyr Pro Pro Leu His Glu Trp Val Leu
                725                 730                 735

Arg Glu Gly Glu Glu Ala Gln Ala Glu Gly Arg Gly Thr Gly Gly Ser
                740                 745                 750

Thr Gly Asp Ala Asp Gly Pro Gly Pro Gly Ile Pro Asp Gly Pro
                755                 760                 765

Gly Gly Asn Ala Gly Gly Pro Gly Glu Ala Gly Ala Thr Gly Gly Arg
            770                 775                 780

Gly Pro Arg Gly Ala Gly Ala Arg Ala Ser Gly Pro Gly Gly Gly
785                 790                 795                 800

Ala Pro Arg Gly Pro His Gly Gly Ala Ala Ser Gly Leu Asn Gly Cys
                805                 810                 815

Cys Arg Cys Gly Ala Arg Gly Pro Glu Ser Arg Leu Leu Glu Phe Tyr
            820                 825                 830

Leu Ala Met Pro Phe Ala Thr Pro Met Glu Ala Glu Leu Ala Arg Arg
            835                 840                 845

Ser Leu Ala Gln Asp Ala Pro Pro Leu Pro Val Pro Gly Val Leu Leu
850                 855                 860

Lys Glu Phe Thr Val Ser Gly Asn Ile Leu Thr Ile Arg Leu Thr Ala
865                 870                 875                 880

Ala Asp His Arg Gln Leu Gln Leu Ser Ile Ser Ser Cys Leu Gln Gln
                885                 890                 895

Leu Ser Leu Leu Met Trp Ile Thr Gln Cys Phe Leu Pro Val Phe Leu
            900                 905                 910

Ala Gln Pro Pro Ser Gly Gln Arg Arg Ile Lys Leu Lys Phe Gly Val
            915                 920                 925

Phe Phe Thr Val Leu Leu Ser Ser Ala Tyr Ala His Gly Thr Pro Gln
930                 935                 940

Asn Ile Thr Asp Leu Cys Ala Glu Tyr His Asn Thr Gln Ile His Thr
945                 950                 955                 960

Leu Asn Asp Lys Ile Phe Ser Tyr Thr Glu Ser Leu Ala Gly Lys Arg
                965                 970                 975

Glu Met Ala Ile Ile Thr Phe Lys Asn Gly Ala Thr Phe Gln Val Glu
                980                 985                 990

Val Pro Gly Ser Gln His Ile Asp Ser Gln Lys Lys Ala Ile Glu Arg
            995                 1000                1005

Met Lys Asp Thr Leu Arg Ile Ala Tyr Leu Thr Glu Ala Lys Val
            1010                1015                1020

Glu Lys Leu Cys Val Trp Asn Asn Lys Thr Pro His Ala Ile Ala
            1025                1030                1035

Ala Ile Ser Met Ala Asn Leu Glu His His His His His His
            1040                1045                1050

<210> SEQ ID NO 59
<211> LENGTH: 757
<212> TYPE: PRT

<213> ORGANISM: Artificial Sequence
<220> FEATURE:
<223> OTHER INFORMATION: Synthetic

<400> SEQUENCE: 59

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Met Gln
        35                  40                  45

Ala Glu Gly Arg Gly Thr Gly Gly Ser Thr Gly Asp Ala Asp Gly Pro
50                  55                  60

Gly Gly Pro Gly Ile Pro Asp Gly Pro Gly Gly Asn Ala Gly Gly Pro
65                  70                  75                  80

Gly Glu Ala Gly Ala Thr Gly Gly Arg Gly Pro Arg Gly Ala Gly Ala
                85                  90                  95

Ala Arg Ala Ser Gly Pro Arg Gly Ala Pro Arg Gly Pro His Gly
            100                 105                 110

Gly Ala Ala Ser Ala Gln Asp Gly Arg Cys Pro Cys Gly Ala Arg Arg
            115                 120                 125

Pro Asp Ser Arg Leu Leu Glu Leu His Ile Thr Met Pro Phe Ser Ser
    130                 135                 140

Pro Met Glu Ala Glu Leu Val Arg Arg Ile Leu Ser Arg Asp Ala Ala
145                 150                 155                 160

Pro Leu Pro Arg Pro Gly Ala Val Leu Lys Asp Phe Thr Val Ser Gly
                165                 170                 175

Asn Leu Leu Phe Met Ser Val Arg Asp Gln Asp Arg Glu Gly Ala Gly
            180                 185                 190

Arg Met Arg Val Val Gly Trp Gly Leu Gly Ser Ala Ser Pro Glu Gly
        195                 200                 205

Gln Lys Ala Arg Asp Leu Arg Thr Pro Lys His Lys Val Ser Glu Gln
    210                 215                 220

Arg Pro Gly Thr Pro Gly Pro Pro Pro Glu Gly Ala Gln Gly Asp
225                 230                 235                 240

Gly Cys Arg Gly Val Ala Phe Asn Val Met Phe Ser Ala Pro His Ile
                245                 250                 255

Pro Leu Glu Gln Arg Ser Gln His Cys Lys Pro Glu Glu Gly Leu Glu
            260                 265                 270

Ala Arg Gly Glu Ala Leu Gly Leu Val Gly Ala Gln Ala Pro Ala Thr
        275                 280                 285

Glu Glu Gln Glu Ala Ala Ser Ser Ser Thr Leu Val Glu Val Thr
    290                 295                 300

Leu Gly Glu Val Pro Ala Ala Glu Ser Pro Asp Pro Gln Ser Pro
305                 310                 315                 320

Gln Gly Ala Ser Ser Leu Pro Thr Thr Met Asn Tyr Pro Leu Trp Ser
                325                 330                 335

Gln Ser Tyr Glu Asp Ser Ser Asn Gln Glu Glu Glu Gly Pro Ser Thr
            340                 345                 350

Phe Pro Asp Leu Glu Ser Glu Phe Gln Ala Ala Leu Ser Arg Lys Val
        355                 360                 365

Ala Glu Leu Val His Phe Leu Leu Leu Lys Tyr Arg Ala Arg Glu Pro
    370                 375                 380

Val Thr Lys Ala Glu Met Leu Gly Ser Val Val Gly Asn Trp Gln Tyr
```

```
                385                 390                 395                 400
        Phe Phe Pro Val Ile Phe Ser Lys Ala Ser Ser Leu Gln Leu Val
                        405                 410                 415
        Phe Gly Ile Glu Leu Met Glu Val Asp Pro Ile Gly His Leu Tyr Ile
                        420                 425                 430
        Phe Ala Thr Cys Leu Gly Leu Ser Tyr Asp Gly Leu Leu Gly Asp Asn
                        435                 440                 445
        Gln Ile Met Pro Lys Ala Gly Leu Leu Ile Ile Val Leu Ala Ile Ile
                    450                 455                 460
        Ala Arg Glu Gly Asp Cys Ala Pro Glu Glu Lys Ile Trp Glu Glu Leu
        465                 470                 475                 480
        Ser Val Leu Glu Val Phe Glu Gly Arg Glu Asp Ser Ile Leu Gly Asp
                            485                 490                 495
        Pro Lys Lys Leu Leu Thr Gln His Phe Val Gln Glu Asn Tyr Leu Glu
                        500                 505                 510
        Tyr Arg Gln Val Pro Gly Ser Asp Pro Ala Cys Tyr Glu Phe Leu Trp
                    515                 520                 525
        Gly Pro Arg Ala Leu Val Glu Thr Ser Tyr Val Lys Val Leu His His
                530                 535                 540
        Met Val Lys Ile Ser Gly Gly Pro His Ile Ser Tyr Pro Pro Leu His
        545                 550                 555                 560
        Glu Trp Val Leu Arg Glu Gly Glu Ala Gln Ala Glu Gly Arg Gly
                        565                 570                 575
        Thr Gly Gly Ser Thr Gly Asp Ala Asp Gly Pro Gly Gly Pro Gly Ile
                        580                 585                 590
        Pro Asp Gly Pro Gly Gly Asn Ala Gly Gly Pro Gly Glu Ala Gly Ala
                    595                 600                 605
        Thr Gly Gly Arg Gly Pro Arg Gly Ala Gly Ala Ala Arg Ala Ser Gly
                610                 615                 620
        Pro Gly Gly Gly Ala Pro Arg Gly Pro His Gly Gly Ala Ala Ser Gly
        625                 630                 635                 640
        Leu Asn Gly Cys Cys Arg Cys Gly Ala Arg Gly Pro Glu Ser Arg Leu
                            645                 650                 655
        Leu Glu Phe Tyr Leu Ala Met Pro Phe Ala Thr Pro Met Glu Ala Glu
                        660                 665                 670
        Leu Ala Arg Arg Ser Leu Ala Gln Asp Ala Pro Pro Leu Pro Val Pro
                    675                 680                 685
        Gly Val Leu Leu Lys Glu Phe Thr Val Ser Gly Asn Ile Leu Thr Ile
                690                 695                 700
        Arg Leu Thr Ala Ala Asp His Arg Gln Leu Gln Leu Ser Ile Ser Ser
        705                 710                 715                 720
        Cys Leu Gln Gln Leu Ser Leu Leu Met Trp Ile Thr Gln Cys Phe Leu
                            725                 730                 735
        Pro Val Phe Leu Ala Gln Pro Pro Ser Gly Gln Arg Arg Leu Glu His
                        740                 745                 750
        His His His His His
                755

<210> SEQ ID NO 60
<211> LENGTH: 234
<212> TYPE: PRT
<213> ORGANISM: Artificial Sequence
<220> FEATURE:
<223> OTHER INFORMATION: Synthetic
```

<400> SEQUENCE: 60

Asn Gln Arg Ala Leu Tyr His Thr Glu Asn Ala Tyr Val Ser Val Val
1               5                   10                  15

Ser Ser Asp Met Arg Ala Glu Ile Ile Lys Met Met Glu Ser Ala Arg
            20                  25                  30

Pro Glu Ala Leu Ala Ser Arg Tyr Leu Thr Asp Met Thr Ile Glu Glu
        35                  40                  45

Met Ser Arg Leu Ala Ser Thr Thr Ala Lys Ala Met Glu Gln Met Ala
    50                  55                  60

Gly Ser Ser Glu Ser Gly Tyr Ala Ala Asp Gln Lys Ser Thr Gln Asn
65                  70                  75                  80

Ala Ile Asn Gly Ile Thr Asn Lys Val Asn Glu Ile Arg Ala Ser Val
                85                  90                  95

Gly Lys Met Ile Asp Gly Ile Gly Arg Phe Tyr Ile Pro Ile Tyr Arg
            100                 105                 110

Arg Val Asp Gly Lys Trp Met Arg Glu Leu Val Leu Tyr Arg Met Cys
        115                 120                 125

Asn Ile Leu Lys Gly Lys Phe Gln Thr Ala Ala Gln Arg Ala Met Ile
    130                 135                 140

Trp Thr Tyr Asn Ala Glu Leu Leu Val Leu Leu Glu Asn Glu Arg Thr
145                 150                 155                 160

Glu Leu Leu Val Leu Leu Glu Asn Glu Arg Thr Leu Asp Phe His Asp
                165                 170                 175

Ser His Lys Ser Gln Leu Val Trp Met Ala Cys Asn Ser Ala Ala Phe
            180                 185                 190

Glu Asp Cys Met Gly Leu Ile Tyr Asn Arg Met Gly Ala Val Thr Thr
        195                 200                 205

Glu Ser Ala Arg Gln Met Val Gln Ala Met Arg Ala Ile Gly Thr His
    210                 215                 220

Pro Ser Ser Ser Thr Gly Leu Lys Asn Asp
225                 230

<210> SEQ ID NO 61
<211> LENGTH: 702
<212> TYPE: DNA
<213> ORGANISM: Artificial Sequence
<220> FEATURE:
<223> OTHER INFORMATION: Synthetic

<400> SEQUENCE: 61
aaccagcgcg ccctgtacca caccgagaac gcctacgtga gcgtggtgag cagcgacatg         60
cgcgccgaga tcatcaagat gatggagagc gcccgccccg aggccctggc cagccgctac        120
ctgaccgaca tgaccatcga ggagatgagc cgcctggcca gcaccaccgc caaggcgatg        180
gagcagatgg ccggcagcag cgagagcggc tacgccgccg accagaagag cacccagaac        240
gccatcaacg gcatcaccaa caaggtgaac gagatccgcg ccagcgtggg caagatgatc        300
gacggcatcg gccgcttcta catccccatc taccgccgcg tggacggcaa gtggatgcgc        360
gagctggtgc tgtaccgcat gtgcaacatc ctgaagggca agttccagac cgccgcccag        420
cgcgccatga tctggaccta caacgccgag ctgctggtgc tgctggagaa cgagcgcacc        480
gagctgctgg tgctgctgga gaacgagcgc accctggact ccacgacag ccacaagagc        540 cagctggtgt ggatggcctg caacagcgcc gccttcgagg actgcatggg cctgatctac        600
aaccgcatgg gcgccgtgac caccgagagc gcccgccaga tggtgcaggc catgcgcgcc        660
atcggcaccc accccagcag cagcaccggc ctgaagaacg ac    702

<210> SEQ ID NO 62
<211> LENGTH: 1062
<212> TYPE: PRT
<213> ORGANISM: Artificial Sequence
<220> FEATURE:
<223> OTHER INFORMATION: Synthetic

<400> SEQUENCE: 62

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Glu Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Met Ser Val Arg Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln Gln
            180                 185                 190

Gly Asp Gly Cys Arg Gly Val Ala Phe Asn Val Met Phe Ser Ala Pro
        195                 200                 205

His Ile Pro Leu Glu Gln Arg Ser Gln His Cys Lys Pro Glu Glu Gly
    210                 215                 220

Leu Glu Ala Arg Gly Glu Ala Leu Gly Leu Val Gly Ala Gln Ala Pro
225                 230                 235                 240

Ala Thr Glu Glu Gln Glu Ala Ala Ser Ser Ser Thr Leu Val Glu
                245                 250                 255

Val Thr Leu Gly Glu Val Pro Ala Ala Glu Ser Pro Asp Pro Pro Gln
            260                 265                 270

Ser Pro Gln Gly Ala Ser Ser Leu Pro Thr Thr Met Asn Tyr Pro Leu
        275                 280                 285

Trp Ser Gln Ser Tyr Glu Asp Ser Ser Asn Gln Glu Glu Glu Gly Pro
    290                 295                 300

Ser Thr Phe Pro Asp Leu Glu Ser Glu Phe Gln Ala Ala Leu Ser Arg
305                 310                 315                 320

Lys Val Ala Glu Leu Val His Phe Leu Leu Leu Lys Tyr Arg Ala Arg
                325                 330                 335

Glu Pro Val Thr Lys Ala Glu Met Leu Gly Ser Val Val Gly Asn Trp
            340                 345                 350

Gln Tyr Phe Phe Pro Val Ile Phe Ser Lys Ala Ser Ser Ser Leu Gln

```
              355                 360                 365
Leu Val Phe Gly Ile Glu Leu Met Glu Val Asp Pro Ile Gly His Leu
    370                 375                 380
Tyr Ile Phe Ala Thr Cys Leu Gly Leu Ser Tyr Asp Gly Leu Leu Gly
385                 390                 395                 400
Asp Asn Gln Ile Met Pro Lys Ala Gly Leu Ile Ile Val Leu Ala
                405                 410                 415
Ile Ile Ala Arg Glu Gly Asp Cys Ala Pro Glu Glu Lys Ile Trp Glu
            420                 425                 430
Glu Leu Ser Val Leu Glu Val Phe Glu Gly Arg Glu Asp Ser Ile Leu
            435                 440                 445
Gly Asp Pro Lys Lys Leu Leu Thr Gln His Phe Val Gln Glu Asn Tyr
        450                 455                 460
Leu Glu Tyr Arg Gln Val Pro Gly Ser Asp Pro Ala Cys Tyr Glu Phe
465                 470                 475                 480
Leu Trp Gly Pro Arg Ala Leu Val Glu Thr Ser Tyr Val Lys Val Leu
                485                 490                 495
His His Met Val Lys Ile Ser Gly Gly Pro His Ile Ser Tyr Pro Pro
            500                 505                 510
Leu His Glu Trp Val Leu Arg Glu Gly Glu Glu Gln Ala Glu Gly Arg
        515                 520                 525
Gly Thr Gly Gly Ser Thr Gly Asp Ala Asp Gly Pro Gly Gly Pro Gly
530                 535                 540
Ile Pro Asp Gly Pro Gly Gly Asn Ala Gly Gly Pro Gly Glu Ala Gly
545                 550                 555                 560
Ala Thr Gly Gly Arg Gly Pro Arg Gly Ala Gly Ala Ala Arg Ala Ser
                565                 570                 575
Gly Pro Gly Gly Gly Ala Pro Arg Gly Pro His Gly Gly Ala Ala Ser
            580                 585                 590
Gly Leu Asn Gly Cys Cys Arg Cys Gly Ala Arg Gly Pro Glu Ser Arg
        595                 600                 605
Leu Leu Glu Phe Tyr Leu Ala Met Pro Phe Ala Thr Pro Met Glu Ala
        610                 615                 620
Glu Leu Ala Arg Arg Ser Leu Ala Gln Asp Ala Pro Pro Leu Pro Val
625                 630                 635                 640
Pro Gly Val Leu Leu Lys Glu Phe Thr Val Ser Gly Asn Ile Leu Thr
                645                 650                 655
Ile Arg Leu Thr Ala Ala Asp His Arg Gln Leu Gln Leu Ser Ile Ser
            660                 665                 670
Ser Cys Leu Gln Gln Leu Ser Leu Leu Met Trp Ile Thr Gln Cys Phe
        675                 680                 685
Leu Pro Val Phe Leu Ala Gln Pro Pro Ser Gly Gln Arg Arg Ile Lys
        690                 695                 700
Leu Lys Phe Gly Val Phe Phe Thr Val Leu Leu Ser Ser Ala Tyr Ala
705                 710                 715                 720
His Gly Thr Pro Gln Asn Ile Thr Asp Leu Cys Ala Glu Tyr His Asn
                725                 730                 735
Thr Gln Ile His Thr Leu Asn Asp Lys Ile Phe Ser Tyr Thr Glu Ser
            740                 745                 750
Leu Ala Gly Lys Arg Glu Met Ala Ile Ile Thr Phe Lys Asn Gly Ala
        755                 760                 765
Thr Phe Gln Val Glu Val Pro Gly Ser Gln His Ile Asp Ser Gln Lys
        770                 775                 780
```

| Lys | Ala | Ile | Glu | Arg | Met | Lys | Asp | Thr | Leu | Arg | Ile | Ala | Tyr | Leu | Thr |
|---|---|---|---|---|---|---|---|---|---|---|---|---|---|---|---|
| 785 | | | | 790 | | | | | 795 | | | | | 800 | |

| Glu | Ala | Lys | Val | Glu | Lys | Leu | Cys | Val | Trp | Asn | Asn | Lys | Thr | Pro | His |
|---|---|---|---|---|---|---|---|---|---|---|---|---|---|---|---|
| | | | | 805 | | | | | 810 | | | | | 815 | |

| Ala | Ile | Ala | Ala | Ile | Ser | Met | Ala | Asn | Gly | Gly | Arg | Asn | Gln | Arg | Ala |
|---|---|---|---|---|---|---|---|---|---|---|---|---|---|---|---|
| | | | 820 | | | | | 825 | | | | | 830 | | |

| Leu | Tyr | His | Thr | Glu | Asn | Ala | Tyr | Val | Ser | Val | Ser | Ser | Asp | Met |
|---|---|---|---|---|---|---|---|---|---|---|---|---|---|---|
| | | 835 | | | | | 840 | | | | | 845 | | |

| Arg | Ala | Glu | Ile | Ile | Lys | Met | Met | Glu | Ser | Ala | Arg | Pro | Glu | Ala | Leu |
|---|---|---|---|---|---|---|---|---|---|---|---|---|---|---|---|
| 850 | | | | | 855 | | | | | 860 | | | | | |

| Ala | Ser | Arg | Tyr | Leu | Thr | Asp | Met | Thr | Ile | Glu | Met | Ser | Arg | Leu |
|---|---|---|---|---|---|---|---|---|---|---|---|---|---|---|
| 865 | | | | 870 | | | | | 875 | | | | | 880 |

| Ala | Ser | Thr | Thr | Ala | Lys | Ala | Met | Glu | Gln | Met | Ala | Gly | Ser | Ser | Glu |
|---|---|---|---|---|---|---|---|---|---|---|---|---|---|---|---|
| | | | | 885 | | | | | 890 | | | | | 895 | |

| Ser | Gly | Tyr | Ala | Ala | Asp | Gln | Lys | Ser | Thr | Gln | Asn | Ala | Ile | Asn | Gly |
|---|---|---|---|---|---|---|---|---|---|---|---|---|---|---|---|
| | | | 900 | | | | | 905 | | | | | 910 | | |

| Ile | Thr | Asn | Lys | Val | Asn | Glu | Ile | Arg | Ala | Ser | Val | Gly | Lys | Met | Ile |
|---|---|---|---|---|---|---|---|---|---|---|---|---|---|---|---|
| | | 915 | | | | | 920 | | | | | 925 | | | |

| Asp | Gly | Ile | Gly | Arg | Phe | Tyr | Ile | Pro | Ile | Tyr | Arg | Arg | Val | Asp | Gly |
|---|---|---|---|---|---|---|---|---|---|---|---|---|---|---|---|
| 930 | | | | | 935 | | | | | 940 | | | | | |

| Lys | Trp | Met | Arg | Glu | Leu | Val | Leu | Tyr | Arg | Met | Cys | Asn | Ile | Leu | Lys |
|---|---|---|---|---|---|---|---|---|---|---|---|---|---|---|---|
| 945 | | | | 950 | | | | | 955 | | | | | 960 | |

| Gly | Lys | Phe | Gln | Thr | Ala | Ala | Gln | Arg | Ala | Met | Ile | Trp | Thr | Tyr | Asn |
|---|---|---|---|---|---|---|---|---|---|---|---|---|---|---|---|
| | | | 965 | | | | | 970 | | | | | 975 | | |

| Ala | Glu | Leu | Leu | Val | Leu | Leu | Glu | Asn | Glu | Arg | Thr | Glu | Leu | Leu | Val |
|---|---|---|---|---|---|---|---|---|---|---|---|---|---|---|---|
| | | | 980 | | | | | 985 | | | | | 990 | | |

| Leu | Leu | Glu | Asn | Glu | Arg | Thr | Leu | Asp | Phe | His | Asp | Ser | His | Lys | Ser |
|---|---|---|---|---|---|---|---|---|---|---|---|---|---|---|---|
| | | 995 | | | | | 1000 | | | | | 1005 | | | |

| Gln | Leu | Val | Trp | Met | Ala | Cys | Asn | Ser | Ala | Ala | Phe | Glu | Asp | Cys |
|---|---|---|---|---|---|---|---|---|---|---|---|---|---|---|
| | 1010 | | | | | 1015 | | | | | 1020 | | | |

| Met | Gly | Leu | Ile | Tyr | Asn | Arg | Met | Gly | Ala | Val | Thr | Thr | Glu | Ser |
|---|---|---|---|---|---|---|---|---|---|---|---|---|---|---|
| | 1025 | | | | | 1030 | | | | | 1035 | | | |

| Ala | Arg | Gln | Met | Val | Gln | Ala | Met | Arg | Ala | Ile | Gly | Thr | His | Pro |
|---|---|---|---|---|---|---|---|---|---|---|---|---|---|---|
| | 1040 | | | | | 1045 | | | | | 1050 | | | |

| Ser | Ser | Ser | Thr | Gly | Leu | Lys | Asn | Asp |
|---|---|---|---|---|---|---|---|---|
| | 1055 | | | | | 1060 | | |

<210> SEQ ID NO 63
<211> LENGTH: 3186
<212> TYPE: DNA
<213> ORGANISM: Artificial Sequence
<220> FEATURE:
<223> OTHER INFORMATION: Synthetic

<400> SEQUENCE: 63

```
atgcaggccg aaggccgggg cacagggggt tcgacgggcg atgctgatgg cccaggaggc    60
cctggcattc ctgatggccc aggggggcaat gctggcggcc caggagaggc gggtgccacg   120
ggcggcagag gtccccgggg cgcaggggca gcaagggcct cggggccgag aggaggcgcc   180
ccgcggggtc cgcatggcgg tgccgcttct gcgcaggatg aaggtgccc ctgcggggcc     240 aggaggccgg acagccgcct gcttgagttg cacatcacga tgcctttctc gtcgccaatg   300
gaagcggagc tggtccgcag aatcctgtcc cggatgccg accgctccc ccgaccaggg     360 gcggttctga aggacttcac cgtgtccggc aacctactgt ttatgtcagt tcgggaccag   420
```

```
gacagggaag gcgctgggcg gatgagggtg gtgggttggg ggctgggatc agcctccccg    480
gaggggcaga aagctagaga tctcagaaca cccaaacaca aggtctcaga acagagacct    540
ggtacaccag gcccgccgcc acccgaggga gcccaggag atgggtgcag aggtgtcgcc     600
tttaatgtga tgttctctgc ccctcacatt cccctggagc agcgcagcca gcactgcaag    660
cccgaggagg gcctggaggc ccgcggcgag gccctgggcc tggtgggcgc ccaggccccc    720
gccaccgagg agcaggaggc cgccagcagc agcagcaccc tggtggaggt gaccctgggc    780
gaggtgcccg ccgccgagag ccccgacccc cccagagcc cccagggcgc cagcagcctg     840
cccaccacca tgaactaccc cctgtggagc cagagctacg aggacagcag caaccaggag    900
gaggagggcc ccagcacctt ccccgacctg gagagcgagt tccaggccgc cctgagccgc    960
aaggtggccg agctggtgca cttcctgctg ctgaagtacc gcgcccgcga gcccgtgacc   1020
aaggccgaga tgctgggcag cgtggtgggc aactggcagt acttcttccc cgtgatcttc   1080
agcaaggcca gcagcagcct gcagctggtg ttcggcatcg agctgatgga ggtggacccc   1140
atcggccacc tgtacatctt cgccacctgc ctggcctga gctacgacgg cctgctgggc    1200
gacaaccaga tcatgcccaa ggccggcctg ctgatcatcg tgctggccat catcgcccgc   1260
gagggcgact gcgcccccga ggagaagatc tgggaggagc tgagcgtgct ggaggtgttc   1320
gagggccgcg aggacagcat cctgggcgac cccaagaagc tgctgaccca gcacttcgtg   1380
caggagaact acctggagta ccgccaggtg cccggcagcg accccgcctg ctacgagttc   1440
ctgtggggcc cccgcgccct ggtggagacc agctacgtga aggtgctgca ccacatggtg   1500
aagatcagcg gcgcccccca catcagctac ccccccctgc acgagtgggt gctgcgcgag   1560
ggcgaggagc aggccgaagg ccggggcaca gggggttcga cgggcgatgc tgatggccca   1620
ggaggccctg gcattcctga tggcccaggg ggcaatgctg gcggcccagg agaggcgggt   1680
gccacgggcg gcagaggtcc ccggggcgca ggggcagcaa gggcctcggg gccgggagga   1740
ggcgccccgc ggggtccgca tggcggcgcg gcttcagggc tgaatggatg ctgcagatgc   1800
ggggccaggg ggccggagag ccgcctgctt gagttctacc tcgccatgcc tttcgcgaca   1860
cccatggaag cagagctggc ccgcaggagc ctggcccagg atgccccacc gcttcccgtg   1920
ccaggggtgc ttctgaagga gttcactgtg tccggcaaca tactgactat ccgactgact   1980
gctgcagacc accgccaact gcagctctcc atcagtcct gtctccagca gctttccctg    2040
ttgatgtgga tcacgcagtg ctttctgccc gtgttttttgg ctcagcctcc ctcagggcag   2100
aggcgcatca gctgaagtt cggcgtgttc ttcaccgtgc tgctgagcag cgcctacgcc    2160
cacggcaccc cccagaacat caccgacctg tgcgccgagt accacaacac ccagatccac   2220
accctgaacg acaagatctt cagctacacc gagagcctgg ccggcaagcg cgagatggcc   2280
atcatcacct tcaagaacgg cgccaccttc caggtggagg tgcccggcag ccagcacatc   2340
gacagccaga agaaggccat cgagcgcatg aaggacaccc tgcgcatcgc ctacctgacc   2400
gaggccaagg tggagaagct gtgcgtgtgg aacaacaaga cccccacgc catcgccgcc    2460 atcagcatgg ccaacggcgg ccgcaaccag cgcgccctgt accacaccga gaacgcctac   2520
gtgagcgtgg tgagcagcga catgcgcgcc gagatcatca gatgatgga gagcgcccgc   2580 cccgaggccc tggccagccg ctacctgacc gacatgacca tcgaggagat gagccgcctg   2640
gccagcacca ccgccaaggc gatggagcag atggccggca gcagcgagag cggctacgcc   2700
gccgaccaga gagcaccca gaacgccatc aacggcatca ccaacaaggt gaacgagatc    2760
cgcgccagcg tgggcaagat gatcgacggc atcgccgct tctacatccc catctaccgc    2820
```

-continued

| | |
|---|---|
| cgcgtggacg gcaagtggat gcgcgagctg gtgctgtacc gcatgtgcaa catcctgaag | 2880 |
| ggcaagttcc agaccgccgc ccagcgcgcc atgatctgga cctacaacgc cgagctgctg | 2940 |
| gtgctgctgg agaacgagcg caccgagctg ctggtgctgc tggagaacga gcgcaccctg | 3000 |
| gacttccacg acagccacaa gagccagctg gtgtggatgg cctgcaacag cgccgccttc | 3060 |
| gaggactgca tgggcctgat ctacaaccgc atgggcgccg tgaccaccga gagcgcccgc | 3120 |
| cagatggtgc aggccatgcg cgccatcggc acccacccca gcagcagcac cggcctgaag | 3180 |
| aacgac | 3186 |

UNITED STATES PATENT AND TRADEMARK OFFICE
CERTIFICATE OF CORRECTION

PATENT NO. : 12,195,517 B2
APPLICATION NO. : 17/280803
DATED : January 14, 2025
INVENTOR(S) : Jianqing Xu et al.

Page 1 of 1

It is certified that error appears in the above-identified patent and that said Letters Patent is hereby corrected as shown below:

On the Title Page

<u>Column</u>
1   Below item (65), insert -- (30) Foreign Application Priority Data
    September 28, 2018 (CN) ...................................... 108331 --

Signed and Sealed this
Tenth Day of February, 2026

John A. Squires
*Director of the United States Patent and Trademark Office*